(12) United States Patent
Tu et al.

(10) Patent No.: US 11,674,146 B2
(45) Date of Patent: Jun. 13, 2023

(54) GENE COMBINATION AND USE THEREOF

(71) Applicants: ZHEJIANG UNIVERSITY, Zhejiang Province (CN); CHINA NATIONAL RICE RESEARCH INSTITUTE, Zhejiang Province (CN)

(72) Inventors: Jumin Tu, Zhejiang Province (CN); Hao Chen, Zhejiang Province (CN); Peisong Hu, Zhejiang Province (CN); Ju Luo, Zhejiang (CN); Xiaobo Zhang, Zhejiang (CN); Yujun Liu, Zhejiang (CN)

(73) Assignees: Zhejiang University, Hangzhou (CN); China National Rice Research Institute, Hangzhou (CN)

( * ) Notice: Subject to any disclaimer, the term of this patent is extended or adjusted under 35 U.S.C. 154(b) by 431 days.

(21) Appl. No.: 16/073,177

(22) PCT Filed: Oct. 31, 2016

(86) PCT No.: PCT/CN2016/103934
§ 371 (c)(1),
(2) Date: Dec. 3, 2018

(87) PCT Pub. No.: WO2017/128791
PCT Pub. Date: Aug. 3, 2017

(65) Prior Publication Data
US 2019/0093118 A1 Mar. 28, 2019

(30) Foreign Application Priority Data

Jan. 26, 2016 (CN) .................. PCT/CN2016/072148

(51) Int. Cl.
| | |
|---|---|
| *C12N 15/82* | (2006.01) |
| *C12N 15/63* | (2006.01) |
| *C07K 14/37* | (2006.01) |
| *C07K 14/32* | (2006.01) |
| *C07K 14/325* | (2006.01) |
| *C07K 14/24* | (2006.01) |
| *C07K 14/33* | (2006.01) |
| *C07K 14/195* | (2006.01) |

(52) U.S. Cl.
CPC ........ *C12N 15/8222* (2013.01); *C07K 14/195* (2013.01); *C07K 14/24* (2013.01); *C07K 14/32* (2013.01); *C07K 14/325* (2013.01); *C07K 14/33* (2013.01); *C07K 14/37* (2013.01); *C12N 15/63* (2013.01); *C12N 15/8201* (2013.01); *C12N 15/8216* (2013.01); *C12N 15/8217* (2013.01); *C12N 15/8275* (2013.01); *C12N 15/8285* (2013.01); *C12N 15/8286* (2013.01)

(58) Field of Classification Search
CPC ................................................. C12N 15/8222
USPC ...................................................... 800/278
See application file for complete search history.

(56) References Cited

U.S. PATENT DOCUMENTS

| | | | | |
|---|---|---|---|---|
| 4,959,317 A | * | 9/1990 | Sauer ..................... | C12N 15/00 435/254.2 |
| 5,723,765 A | | 3/1998 | Oliver et al. | |
| 7,615,624 B2 | * | 11/2009 | Budworth ............ | C07K 14/415 435/419 |
| 2004/0143874 A1 | * | 7/2004 | Moller ............... | C12N 15/8237 800/288 |
| 2004/0268443 A1 | * | 12/2004 | Wu ..................... | C12N 15/8261 800/290 |
| 2007/0006347 A1 | * | 1/2007 | Plesch ................. | C12N 15/8216 800/288 |
| 2011/0173717 A1 | | 7/2011 | Hill et al. | |
| 2015/0020235 A1 | * | 1/2015 | Los ........................ | C12N 15/80 800/278 |

FOREIGN PATENT DOCUMENTS

| | | |
|---|---|---|
| CN | 1531394 A | 9/2004 |
| CN | 1840655 A | 10/2006 |
| CN | 101624594 A | 1/2010 |
| CN | 102181436 A | 9/2011 |
| CN | 102181463 A | 9/2011 |
| CN | 102392038 A | 3/2012 |
| CN | 102443574 A | 5/2012 |
| CN | 103966249 A | 8/2014 |
| CN | 109804066 A | 5/2019 |
| CN | 109952310 A | 6/2019 |
| CN | 112646835 A | 4/2021 |
| WO | 2000066747 A1 | 11/2000 |
| WO | 2003012035 A2 | 2/2003 |
| WO | 2014145346 A2 | 9/2014 |
| WO | 2015191374 A1 | 12/2015 |

OTHER PUBLICATIONS

Brent et al (Nature, 1984, 312(13): 612-615) (Year: 1984).*
GenBank EU864235.1 (published online 2008) (Year: 2008).*
GenBank AF330636.1 (published online 2001) (Year: 2001).*
Corrado et al (Biotechnology Advances, 2009, 27(6): 733-743) (Year: 2009).*
Cao et al. (Plant Cell Reports, 2006, 25: 554-560) (Year: 2006).*
International Search Report and Written Opinion for Application No. PCT/CN2016/103934 dated Jan. 13, 2017 (12 pages).
Qiu, Shuping, The Preliminary Study on the Local Deletion of Exogenous Gene in the Endosperm Using Cre / Ioxp System in Transgenic Rice, Agriculture, China Master's Theses Full-Text Database, No. 12, Dec. 15, 2008 (Dec. 15, 2008), ISSN: 1674-0246, see the whole document.

(Continued)

*Primary Examiner* — Li Zheng
(74) *Attorney, Agent, or Firm* — Michael Best & Friedrich LLP

(57) ABSTRACT

Provided are a gene combination used for controlling foreign gene expression in a specific plant tissue, and a method applying the gene combination to cultivate a transgenic plant. The method is used to cultivate, for example, an endosperm zero expression-type transgenic rice, i.e., rice grain endosperm produced by the rice does not contain any transgenic product protein synthesis and accumulation.

24 Claims, 20 Drawing Sheets

Specification includes a Sequence Listing.

(56) References Cited

OTHER PUBLICATIONS

Feng, Qingling, The Tentative Establishment of a New Foreign Gene Elimination System in Rice Endosperm, Agriculture, China Master's Theses Full-Text Database, No. 12, Dec. 15, 2012 (Dec. 15, 2012), ISSN: 1674-0246, see the whole document.
Moore, S.K. et al., "Efficient Deletion of Transgenic DNA from Complex Integration Locus of Rice Mediated by Cre/lox Recombination System", Crop Science, vol. 46, No. 2, Dec. 31, 2005 (Dec. 31, 2005), ISSN: 0011-183X, pp. 700-705, see the whole document.
Zhao, Yan et al., "Application of Cre / lox Site-Specific Recombination System in Transgenic Plants", Chinese Journal of Biochemistry and Molecular Biology, vol. 26, No. 2, Feb. 28, 2010 (Feb. 28, 2010), ISSN 1007-7626, pp. 95-103, see the whole document.
Parkhi, V. et al., "Molecular characterization of marker-free transgenic lines of indica rice that accumulate carotenoids in seed endosperm", Mol Gen Genomics, vol. 274, Sep. 23, 2005 (Sep. 23, 2005), ISSN 1617-4615, pp. 325-336, see the whole document.
Bock, R., 2001, "Transgenic plastids in basic research and plant biotechnology", J. Mol. BioL., 312:425-438.
Cai, M. et al., 2007, "A rice promoter containing both novel positive and negative cis-elements for regulation of green tissue-specific gene expression in transgenic plants", Plant Biotechnol J, 5:664-674.
Chu, C. et al., 1975, "Establishment of an efficient medium for anther culture of rice through comparative experiments on the nitrogen sources", Sci Sin., 18:659-668.
Daniell, H., 2002, "Molecular strategies for gene containment in transgenic crops", Nat. Biotechnol., 20(6):581-586.
Hiei, Y. et al., 1994, "Efficient transformation of rice (*Oryza sativa* L.) mediated by Agrobacterium and sequence analysis of the boundaries of T-DNA", Plant J., 6:271-282.
James, C., 2014, "Global Status of Commercialized Biotech/GM Crops: 2014", ISAAA Brief No. 49. ISAAA: Ithaca, NY.
Jang, I. C. et al., 1999, "Subcellular targeting of green fluorescent protein to plastids in transgenic rice plants provides a high-level expression system", Mo! Breeding, 5:453-461.
Kyozuka, J. et al., 1993, "Light-regulated and cell-specific expression of tomato rbcS-gusA and rice rbcS-gusA fusion genes in transgenic rice", Plant Physiol, 102:991-1000.
Liu, Q.Q. et al., 1998, "A highly efficient transformation system mediated by Agrobacterium tumfaciens in rice", Acta Phytophysiol 25 Sin., 24:259-271.
Luo, K. et al., 2007, "GM-gene-deletor": fused loxP-FRT recognition sequences dramatically improve the efficiency of FLP or CRE recombinase on trans gene excision from pollen and seeds of tobacco plants, Plant Bio tech J., 5 (2):263-274.
Paoletti, M.G. et al., 1996, "Genetic engineering in agriculture and the environment", Bioscience, 46(9):665-673.
Thilmony, R. et al., 2009, "The LP2 leueine-rich repeat receptor kinase gene promoter directs organ-specific,light-responsive expression in transgenic rice", Plant Bioteclmol J., 7:867-882.
Toriyama, K. et al., 1985, "Cell suspension and protoplast culture in rice", Plant Sci., 41:179-183.
Tu, J. et al., 2000, "Field performance of transgenic elite commercial hybrid rice expressing Bacillus thuringiensis 8-endotoxin". Nature Biotech, 18:1101-1104.
Yanagisawa, S. et al., 1989, "Maize Phosphoenol pyruvate Carboxylase Involved in C4 Photosynthesis: Nucleotide Sequence Analysis of the 5' Flanking Region 15 of the Gene", J Biochem., 106:982-987.
Ye, R.J. et al., 2012, "Two novel positive cis-regulatory elements involved in green tissue-specific promoter activity in rice (*Oryza sativa* L ssp.)", Plant Cell Rep, 31:1159-1172.
Koshida, S. et al., 1976, "Routine procedures for growing rice plants in culture solution", In Laboratory Manual for Physiological Studies of 25 Rice pp. 61-66. Philippines, IRRI, Manila.
Zhao, D. et al., 2008, "The gene-deletor technology: principle and potential application in genetically engineered agriculture", Molecular Plant Breeding, 2008, 6(3): 413-418.
GenBank Database, Accession No. NM 114923.3, *Arabidopsis thaliana* cyclin-dependent kinase inhibitor 2 mRNA complete cds, 2014, 2 pages.
GenBank Database, Accession No. AB449974.1, Enterobacteria phage P1 cre gene for Cre recombinase complete cds, 2008, 1 page.
Hao, "Development of a 'Gene-Switch' system and its application in producing 'Green' insect-resistance rice with null expression in the endosperm", China dissertation database doctral thesis, abstract, Zhejiang University, 2016, 7 pages.
Xu, "Effect of Several NLS on Deletion Efficiency of Site-Specific Recombinase", China Master's Thesis, vol. 10, abstract, 2009, 3 pages.
National Intellectual Property Administration People's Republic China Search Report for Application No. 201680080151 X dated Aug. 4, 2021 (3 pages).
Intellectual Property Office India Examination Report for Application No. 201847028088 dated Feb. 7, 2022 (7 pages with English translation).
National Intellectual Property Administration, P.R. China, Second Office Action for Application No. 201680080151.X dated Jul. 25, 2022 (11 pages including English translation).
Bird et al., "*Arabidopsis* cyclin-dependent kinase inhibitors are nuclear-localized and show different localization patterns within the nucleoplasm", Plant Cell Rep, 2007, vol. 26, pp. 861-872.

* cited by examiner

GENE COMBINATION AND USE THEREOF

TECHNICAL FIELD

The present invention relates to the field of transgenic plants. In particular, the present invention relates to a gene combination for controlling the expression of an exogenous target gene in a plant, and a method of breeding a transgenic plant using the gene combination.

BACKGROUND ART

Since its appearance in the 1980s, transgenic technology has achieved remarkable achievements. The cultivated transgenic crops have been grown in 28 countries around the world, with a production area of 181.5 million hectares in 2014 (James, et al., 2014). According to the latest real-time information provided by Brooks and Buffett of PG Economics, UK, transgenic crops increased crop production value by $133 billion and saved active pesticide agents by 500 million kg in 17 years from 1996 to 2013. Only in 2013, carbon dioxide emission thus reduced achieved 2.8 billion kg, equaling to the emissions of 12.4 million cars in one year. Transgene also made contribution to 1.65 million small farms and their families, totaling 65 million people in the some world's poorest countries to alleviate their poverty (James, et al., 2014). They therefore concluded that transgenic crops continue to have a significant positive impact on food safety, sustainable development and climate change. Currently, more than 10 food and fiber crops have been approved for commercial cultivation, ranging from large-scale food and commercial crops such as corn, soybean and cotton to small-scale fruit and vegetable crops such as papaya, eggplant and pumpkin.

Rice is the main food crop of 50% of the world's population. Transgenic rice lines, such as the elite transgenic restorer line Minghui 63/Bt (Huahui 1) and its derivative hybrid Shanyou 63/Bt, were announced to be successfully developed in 2000 (Tu, et al., 2000). The biosafety certificate has also been issued by the Ministry of Agriculture of China in November 2009 upon the repeated verification of no biosafety risk by the developer and third parties. However, since these traditional insect-resistant rice lines express *Bacillus thuringiensis* (Bt) transgene in its endosperm (that is, the expression product of Bt gene is accumulated in the transgenic rice produced), it is still difficult for the public to recognize its food safety, and its commercial planting has not been approved yet. This situation is true not only in China, but also in other regions and countries of the world such as Europe and Japan. 58% of the people surveyed in Europe in 2006 thought that transgenic foods "should not be encouraged".

In order to address people's fears and concerns about the ecological safety and food safety of transgenic plants, many safe biotechnologies have been developed, such as transgenic pollen sterility technology (Paoletti and Pimentel. 1996), seed sterility or seedless technology (Daniell, 2002; Li, 1998), chloroplast transgenic technology (Bock, 2001), the "Terminator" seed technology (Oliver, et al., 1998) and exogenous gene deletion technology (Luo, et al., 2007). Among these technologies, the most influential one is the exogenous gene deletion technology developed by Professor Yi LI and his student Keming LUO of the University of Connecticut. With this technology, the transgenic plant automatically removes exogenous genes from pollens and seeds around the flowering stage, as the computer "unloads" application software, so that the exogenous genes in the transgenic plant are automatically cleared before diffusion and before use by the people (Zhao Degang et al., 2008). This technology can be applied directly to asexually propagated crops, but still needs to be modified before applying to sexually propagated crops. The main problem is that upon the removal, the exogenous target gene will no longer retain in the seeds of sexually propagated crops, thereby rendering the next generation propagated through the seeds lose the transgenic trait.

Therefore, for the crops such as transgenic foods, vegetables, and fruits, there is an urgent need for a novel biotechnology system that can shut down the expression of a target gene in an edible tissue or organ without losing the transgenic trait in the next generation that is propagated through the seeds.

SUMMARY OF THE INVENTION

For the above purposes, the inventors have developed a gene combination capable of switching off the expression of a target gene in a particular tissue/organ (e.g., endosperm). The technique consists essentially of a lock element capable of blocking (i.e., switching off) the expression of an exogenous target gene, and a key gene capable of switching on the expression of the exogenous target gene. When existing separately, the lock element permanently blocks the expression of the exogenous target gene that is carried by the lock element, while the key gene, which is capable of switching on the blocked expression of the exogenous target gene, is expressed only in a specific tissue/organ. The two components are separately transformed and integrated into the parental genome of such as rice, and then they can be combined together by the hybrid production. The transgenic plants, having the exogenous target gene expressed in specific tissues/organs to exhibit the desired phenotype, while having no expression of the exogenous target gene in other specific tissues/organs (e.g., an edible organ, such as a rice endosperm) and thus no transgenic component in the portion for consumption, are thus produced. Similarly, the same effect can be obtained by introducing and combining these two components in the genome of the same recipient plant. Meanwhile, the present invention does not concern the problem of incapable of passing the DNA of target gene due to gene deletion in the propagation process, and therefore has a wide applicability.

Specifically, in a first aspect, the present invention provides a gene combination for controlling expression of an exogenous target gene in a plant, which consists of a lock element and a key gene, wherein the lock element comprises the nucleotide sequence shown in SEQ ID NO: 5 or 8, or comprises a nucleotide sequence having at least 80% homology to the nucleotide sequence shown in SEQ ID NO: 5 or 8 and capable of blocking the expression of an exogenous target gene operably linked thereto; and the key gene comprises the nucleotide sequence shown in SEQ ID NO: 3 or 6, or comprises a nucleotide sequence having at least 40% homology to the nucleotide sequence shown in SEQ ID NO: 3 or 6 and capable of switching on the expression of the exogenous target gene blocked by the lock element.

In one aspect, the present invention provides a lock element for blocking the expression of an exogenous target gene operably linked thereto in a plant, which comprises the nucleotide sequence shown in SEQ ID NO: 5 or 8, or comprises a nucleotide sequence having at least 80% homology to the nucleotide sequence shown in SEQ ID NO: 5 or 8 and capable of blocking the expression of an exogenous target gene operably linked thereto.

Accordingly, in one aspect, the present invention provides a key gene for switching on the expression of the exogenous target gene blocked by the lock element in a specific plant tissue, which comprises the nucleotide sequence shown in SEQ ID NO: 3 or 6, or comprises a nucleotide sequence having at least 40% homology to the nucleotide sequence shown in SEQ ID NO: 3 or 6 and capable of switching on the expression of the exogenous target gene blocked by the lock element.

In a second aspect, the invention provides a method for controlling the expression of an exogenous target gene in a plant, the method comprising introducing a lock element and a key gene into a recipient plant, wherein the lock element comprises the nucleotide sequence shown in SEQ ID NO: 5 or 8, or comprises a nucleotide sequence having at least 80% homology to the nucleotide sequence shown in SEQ ID NO: 5 or 8 and capable of blocking the expression of an exogenous target gene operably linked thereto; and the key gene comprises the nucleotide sequence shown in SEQ ID NO: 3 or 6, or comprises a nucleotide sequence having at least 40% homology to the nucleotide sequence shown in SEQ ID NO: 3 or 6 and capable of switching on the expression of the exogenous target gene blocked by the lock element.

In one aspect, the present invention provides a method for controlling the expression of an exogenous target gene in a plant, the method comprising operably linking the exogenous target gene to a lock element, the lock element comprising the nucleotide sequence shown in SEQ ID NO: 5 or 8, or comprising a nucleotide sequence having at least 80% homology to the nucleotide sequence shown in SEQ ID NO: 5 or 8, and capable of blocking the expression of an exogenous target gene operably linked thereto.

Accordingly, in one aspect, the present invention provides a method for switching on the expression of the exogenous target gene blocked by the lock element in a plant, the method comprising introducing the key gene into the plant, the key gene comprises the nucleotide sequence shown in SEQ ID NO: 3 or 6, or comprises a nucleotide sequence having at least 40% homology to the nucleotide sequence shown in SEQ ID NO: 3 or 6 and capable of switching on the expression of the exogenous target gene blocked by the lock element.

In a third aspect, the invention provides a method of breeding a transgenic plant, the method comprising crossing a first parent plant comprising a lock element with a second parent plant comprising a key gene, thereby obtaining the transgenic plant, wherein the lock element comprises the nucleotide sequence shown in SEQ ID NO: 5 or 8, or comprises a nucleotide sequence having at least 80% homology to the nucleotide sequence shown in SEQ ID NO: 5 or 8 and capable of blocking the expression of an exogenous target gene operably linked thereto; and the key gene comprises the nucleotide sequence shown in SEQ ID NO: 3 or 6, or comprises a nucleotide sequence having at least 40% homology to the nucleotide sequence shown in SEQ ID NO: 3 or 6 and capable of switching on the expression of the exogenous target gene blocked by the lock element.

In a specific embodiment, the method further comprises, prior to the crossing step, introducing and/or integrating the lock element into the genome of the first parent plant, and introducing and/or integrating the key gene into the genome of the second parent plant.

In an alternative embodiment, the invention provides a method of breeding a transgenic plant, the method comprising introducing and/or integrating a lock element and a key gene into the genome of the same plant, thereby obtaining a transgenic plant comprising both the lock element and the key gene, wherein the lock element comprises the nucleotide sequence shown in SEQ ID NO: 5 or 8, or comprises a nucleotide sequence having at least 80% homology to the nucleotide sequence shown in SEQ ID NO: 5 or 8 and capable of blocking the expression of an exogenous target gene operably linked thereto; and the key gene comprises the nucleotide sequence shown in SEQ ID NO: 3 or 6, or comprises a nucleotide sequence having at least 40% homology to the nucleotide sequence shown in SEQ ID NO: 3 or 6 and capable of switching on the blocked expression of the exogenous target gene by the lock element.

In a fourth aspect, the invention provides use of a combination of a lock element and a key gene for regulating the expression of an exogenous target gene in a plant, wherein the lock element is capable of blocking the expression of an exogenous target gene operably linked thereto; the key gene is capable of switching on the expression of the exogenous target gene blocked by the lock element.

In a specific embodiment of this aspect, the lock element comprising the nucleotide sequence shown in SEQ ID NO: 5 or 8, or comprising a nucleotide sequence having at least 80% homology to the nucleotide sequence shown in SEQ ID NO: 5 or 8, and capable of blocking the expression of an exogenous target gene operably linked thereto; and the key gene comprises the nucleotide sequence shown in SEQ ID NO: 3 or 6, or comprises a nucleotide sequence having at least 40% homology to the nucleotide sequence shown in SEQ ID NO: 3 or 6 and capable of switching on the expression of the exogenous target gene blocked by the lock element.

According to some specific embodiments of the invention, the gene combination is a lock element comprising a nucleotide sequence of SEQ ID NO: 5 or having at least 80% homology to SEQ ID NO: 5, and a key gene comprising a nucleotide sequence of SEQ ID NO: 3 or having at least 40% homology to SEQ ID NO: 3.

According to further specific embodiments of the invention, the gene combination is a lock element comprising a nucleotide sequence of SEQ ID NO: 8 or having at least 80% homology to SEQ ID NO: 8, and a key gene comprising a nucleotide sequence of SEQ ID NO: 6 or having at least 40% homology to SEQ ID NO: 6.

According to various aspects of the invention, the lock element is located between a constitutive promoter and the exogenous target gene, and is operably linked to the constitutive promoter and the exogenous target gene.

According to various aspects of the invention, the key gene is operably linked to a tissue-specific promoter.

According to various aspects of the invention, the constitutive promoter is selected from the group consisting of the cauliflower mosaic virus (CaMV) 35S promoter, the nopaline synthase gene Ocs promoter from the T-DNA region of the *Agrobacterium tumefaciens* Ti plasmid, the rice actin promoter Actin I, the maize ubiquitin gene promoter Ubi; preferably, the constitutive promoter is the rice actin promoter Actin I.

According to various aspects of the invention, the tissue-specific promoter is selected from the group consisting of the rice green tissue-specific promoter ribulose-1,5-bisphosphate carboxylase small subunit rbcS promoter (Kyozuka et al, 1993; Nomura et al, 2000), the maize phosphoenolpyruvate carboxylase PEPC promoter (Yanagisawa et al, 1989), the rice green tissue-specific expression DX1 promoter (Ye et al, 2012), the rice photosystem II 10 kDa polypeptide D540 promoter (Cai et al. 2007), the rice leucine-rich repeat-like receptor protein kinase LP2 promoter (Thilmony et al, 2009), and the maize chloroplast C4 Pdk promoter (Jang et al, 1999); preferably, the tissue-specific promoter is the rice green tissue-specific promoter rbcS promoter.

According to various aspects of the invention, the exogenous target gene may be an insect resistant gene or a herbicide resistant gene. The insect resistant gene includes the cry1Ab, cry1Ac, cry1Ab/Ac, cry1C, cry2A and Vip3 insect resistant genes from *Bacillus thuringiensis*, the anf, sep genes from *Serratia entomophila*, cmb gene of *Clostridium bifermentans*, the mtx gene from *Bacillus sphaericus*, the insecticidal protein gene from *Xenorhabdus nematophilus*, the tca, tcb genes from *Photorhabdus luminescens*, and the pr1 gene from *Metarhizium anisopliae*, but is not limited thereto.

According to the present invention, the nucleotide coding sequence and amino acid sequence of the *Bacillus thuringiensis* (Bt) insect resistant gene are shown in SEQ ID NO: 1 and SEQ ID NO: 2, respectively.

According to various aspects of the invention, the herbicide resistant gene includes the EPSP synthase gene for glyphosate resistance, the *Salmonella typhimurium* EPSP mutant gene aroA, the bar gene for glufosinate resistance, the ALS mutant gene Ilv G for imidazolone resistance, the AccL-s2 gene for sethoxydim resistance, the bxn gene for bromoxynil resistance, and the csrl gene for chlorsulfuron resistance, but is not limited thereto.

According to various aspects of the invention, the plant is selected from the group consisting of rice, wheat, barley, oat, maize, millet, sorghum, pearl barley, sweet potato, potato, lotus seed, soybean, and peanut. Preferably, the plant is rice.

The following definitions are used herein to further define and describe the present disclosure. These definitions apply to the terms used throughout this specification unless otherwise defined in the specific context.

Unless defined otherwise, all technical and scientific terms used herein have the same meaning as commonly understood by one of ordinary skill in the art to which the present invention pertains. In the event of a conflict, the present specification, including the definitions given herein, will control.

Lock Element (LOCK) and Key Gene (KEY)

The present inventors provide via DNA recombination a combination of a regulatory element and a gene sequence having functions of regulating gene expression, and named them as a lock element (LOCK) and a key gene (KEY) according to their respective functions.

The lock element can block (i.e., switch off) the expression of an exogenous target gene linked thereto. Specifically, the lock element comprises the nucleotide sequence shown in SEQ ID NO: 5 or 8, or comprises a nucleotide sequence having at least 80% homology to the nucleotide sequence shown in SEQ ID NO: 5 or 8, and capable of blocking the expression of an exogenous target gene operably linked thereto. Preferably, the lock element comprises the nucleotide sequence shown in SEQ ID NO: 5 or 8, or consists of the nucleotide sequence shown in SEQ ID NO: 5 or 8.

The key gene can switch on the expression of the exogenous target gene blocked by the lock element. Specifically, the key gene comprises the nucleotide sequence shown in SEQ ID NO: 3 or 6, or comprises a nucleotide sequence having at least 40% homology to the nucleotide sequence shown in SEQ ID NO: 3 or 6 and capable of switching on the expression of the exogenous target gene blocked by the lock element. Preferably, the key gene comprises the nucleotide sequence shown in SEQ ID NO: 3, or consists of the nucleotide sequence shown in SEQ ID NO: 3.

The degree of homology between two nucleotide sequences can be determined by the algorithms known in the art. The optimal alignment of the sequences used for comparison can be performed by: local homology algorithm [Smith and Waterman Add. APL. Math. 2:482 (1981)]; homology alignment algorithm [Needleman and Wunsch J. Mol. Biol. 48:443 (1970); searching similarity algorithms [Pearson and Lipman Proc. Natl. Acad Sci. (USA) 85: 2444 (1988)]; the computer programs for these algorithms and their default parameters [GAP, BESTFIT, BLAST, PASTA, and TFASTA in Wisconsin Genetics software package, Genetics Computer Group (GCG), 575 Science Dr., Madison, Wis.]; or by visual inspection.

According to the present invention, the lock element may comprise a nucleotide sequence having at least 80%, for example at least 91%, 92%, 93%, 94%, 95%, 96%, 97%, 98%, 99%, 99.5%, 99.8% or 100% homology to the nucleotide sequence shown in SEQ ID NO: 5 or 8, and capable of blocking the expression of an exogenous target gene operably linked thereto. The homology may be calculated using BLAST and its default parameters.

According to the present invention, the key gene may comprise a nucleotide sequence having at least 40%, for example at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.8% or 100% homology to the nucleotide sequence shown in SEQ ID NO: 3 or 6 and capable of switching on the expression of the exogenous target gene blocked by the lock element. The homology may be calculated using BLAST and its default parameters.

In a specific embodiment, the gene combination of the present invention is a lock element comprising SEQ ID NO: 5 or a nucleotide sequence having at least 80% homology to SEQ ID NO: 5, in combination with a key gene comprising SEQ ID NO: 3 or a nucleotide sequence having at least 40% homology to SEQ ID NO: 3.

In another specific embodiment, the gene combination of the present invention is a lock element comprising SEQ ID NO: 8 or a nucleotide sequence having at least 80% homology to SEQ ID NO: 8, in combination with a key gene comprising SEQ ID NO: 6 or a nucleotide sequence having at least 40% homology to SEQ ID NO: 6.

According to the present invention, the lock element may: 1) comprise the nucleotide sequence shown in SEQ ID NO: 5 or 8, or 2) comprise a nucleotide sequence derived from the nucleotide sequence shown in SEQ ID NO: 5 or 8 by substitution, deletion or addition of one or more nucleotides and capable of blocking the expression of an exogenous target gene operably linked thereto.

According to the present invention, the key gene may: 1) comprise the nucleotide sequence shown in SEQ ID NO: 3 or 6, or 2) comprise a nucleotide sequence derived from the nucleotide sequence shown in SEQ ID NO: 3 or 6 by substitution, deletion or addition of one or more nucleotides and capable of switching on the expression of the exogenous target gene blocked by the lock element.

According to the present invention, the key gene may: 1) encode the amino acid sequence shown in SEQ ID NO: 4 or 7, or 2) encode an amino acid sequence derived from the amino acid sequence shown in SEQ ID NO: 4 or 7 by substitution, deletion or addition of one or more amino acids and capable of switching on the expression of the exogenous target gene blocked by the lock element.

According to the present invention, the lock element may: 1) comprise the nucleotide sequence shown in SEQ ID NO:

5 or 8, or 2) hybridize to a sequence complementary to the nucleotide sequence shown in SEQ ID NO: 5 or 8 under stringent conditions, and be capable of blocking the expression of an exogenous target gene operably linked thereto.

According to the present invention, the key gene may: 1) comprise the nucleotide sequence shown in SEQ ID NO: 3 or 6, or 2) hybridize to a sequence complementary to the nucleotide sequence shown in SEQ ID NO: 3 or 6 under stringent conditions, and be capable of switching on the expression of the exogenous target gene blocked by the lock element.

"Stringent condition" is used herein to describe the hybridization between nucleotide sequences in 6× sodium chloride/sodium citrate (SSC) at about 45° C., followed by one or more washes in 0.2×SSC/0.1% SDS at about 50-65° C. Preferably, the stringent condition is "highly stringent condition". The term "highly stringent conditions" refers to, for example, the hybridization between nucleotide sequences in 6×SSC at about 45° C. followed by one or more washes in 0.1×SSC/0.2% SDS at about 68° C.

According to the present invention, the regulatory gene combination composed of the lock element and the key gene can control the expression of the exogenous target gene in a plant, thereby blocking the expression of the exogenous target gene in the storage tissue or organ such as endosperm, root, tuber, and pulp while achieving the gene function of the exogenous target gene, thereby resulting in the endosperm, root, tuber, and pulp free of the transgenic expression product, while not affecting the passage of the exogenous target gene to the next generation through sexual propagation.

In a specific embodiment, the lock element is placed between the constitutive promoter and the exogenous target gene, thereby blocking expression of the exogenous target gene in the whole transgenic plant comprising the lock element; meanwhile, the key gene is operably linked to a tissue-specific promoter, thereby switching on the expression of the exogenous target gene blocked by the lock element in the specific tissue to achieve the function of the exogenous target gene.

Promoter

According to the present invention, the "promoter" refers to a genetic element that initiates the transcription. The promoters can be classified into the constitutive promoter, the tissue-specific promoter, and the inducible promoter according to their modes of action.

According to the present invention, a "constitutive promoter" refers to a promoter that maintains sustained activity in most or all tissues. Under the regulation of a constitutive promoter, there is no significant difference in gene expressions among different tissues and developmental stages. Preferably, the constitutive promoter for use in the present invention is a promoter derived from a plant or having the constitutive activity in a plant.

Examples of the constitutive promoters useful in the present invention include, but are not limited to, the cauliflower mosaic virus (CaMV) 35S promoter, the nopaline synthase gene Ocs promoter from the T-DNA region of the *A. tumefaciens* Ti plasmid, the rice actin promoter Actin I, the maize ubiquitin gene promoter Ubi, etc. Preferably, the constitutive promoter of the present invention is the rice actin promoter Actin I.

According to the present invention, the tissue-specific promoter refers to a promoter that is active in a particular type of cell or tissue. Under the regulation of the tissue-specific promoter, a gene is expressed only in certain specific organs or tissues. Preferably, the tissue-specific promoter for use in the present invention is a promoter derived from a plant or having tissue-specific activity in a plant. One skilled in the art can select the tissue-specific promoter according to the plant species and the organ/tissue wherein the expression of the exogenous target gene is desired/undesired (e.g., plant tissues/organs for consumption).

The tissue-specific promoters useful in the present invention include: a root-specific promoter, a stalk-specific promoter, and a leaf-specific promoter. Preferably, the tissue-specific promoter of the invention is a green tissue-specific promoter of a plant, e.g., a stalk and/or leaf-specific promoter. Specifically, examples of the tissue-specific promoter according to the present invention include the rice green tissue-specific promoter ribulose-1,5-bisphosphate carboxylase small subunit rbcS promoter, the maize phosphoenolpyruvate carboxylase PEPC promoter, the rice green tissue-specific expression DX1 promoter, the rice photosystem II 10 kDa polypeptide D540 promoter, the rice leucine-rich repeat-like receptor protein kinase LP2 promoter, and the maize chloroplast C4 Pdk promoter, but are not limited thereto. Preferably, the tissue-specific promoter of the present invention is the rice green tissue-specific promoter rbcS promoter.

According to the present invention, the promoter is "operably linked" to the lock element or key gene. The "operably linked" refers to an arrangement of elements wherein the elements are configured to perform their normal function. For example, if a promoter affects the transcription of a coding sequence, then it is operably linked to the coding sequence.

Exogenous Target Gene

According to the present invention, the "exogenous target gene" refers to a foreign gene which is not found in a recipient plant in a natural state. A number of exogenous target genes have been introduced into recipient plants for various purposes, so as to increase plants' resistance to pests, herbicides, etc., and to increase and stabilize crop yields, etc.

According to the present invention, the exogenous target gene may be an insect resistant gene or a herbicide resistant gene. The insect resistant gene includes the cry1Ab, cry1Ac, cry1Ab/1Ac, cry1C, cry2A and Vip3 like insect resistant genes from *Bacillus thuringiensis*, the anf, sep genes from *Serratia entomophila*, cmb gene of *Clostridium bifermentans*, the mtx gene from *Bacillus sphaericus*, the insecticidal protein gene from *Xenorhabdus nematophilus*, the tca, tcb genes from *Photorhabdus luminescens*, and the pr1 gene from *Metarhizium anisopliae*, but is not limited thereto.

According to the present invention, the nucleotide coding sequence and amino acid sequence of the Bt insect resistant gene are shown in SEQ ID NO: 1 and SEQ ID NO: 2, respectively.

According to the present invention, the herbicide resistant gene includes the EPSP synthase gene for glyphosate resistance, the *Salmonella typhimurium* EPSP mutant gene aroA, the bar gene for glufosinate resistance, the ALS mutant gene Ilv G for imidazolone resistance, the AccL-s2 gene for sethoxydim resistance, the bxn gene for bromoxynil resistance, and the csrl gene for chlorsulfuron resistance, but is not limited thereto.

According to the present invention, the expression of the exogenous target gene is controlled by the lock element and the key gene of the present invention. In a specific embodiment, the exogenous gene is operably linked to the lock element of the invention.

If desired, the sequence encoding the exogenous target gene is also operably linked to an appropriate regulatory factor, including a promoter, an enhancer, a terminator, and a signal peptide sequence.

Transgenic Plant

The invention provides a method of breeding a transgenic plant, the method comprising crossing a first parent plant comprising the lock element of the present invention with a second parent plant comprising the key gene of the present invention, thereby obtaining the transgenic plant.

In a specific embodiment, the method of breeding a transgenic plant of the present invention further comprises, prior to the crossing step, introducing and integrating the lock element and a target gene linked thereto into the genome of the first parent plant, and introducing and integrating the key gene into the genome of the second parent plant.

In an alternative embodiment, the invention provides a method of breeding a transgenic plant, the method comprising introducing and integrating the lock element and the key gene of the present invention into the genome of the same plant, thereby obtaining the transgenic plant.

The methods for introducing a gene into a recipient plant are known in the art and include, for example, *Agrobacterium*-mediated gene transformation, gene gun transformation, pollen tube pathway method, etc., wherein the *Agrobacterium*-mediated gene transformation is widely used in the plant transformation. The specific steps can be found in the following attached examples.

In a further contemplated embodiment of the invention, specific exogenous genes, e.g., marker genes for screening, can be isolated and knocked from the transgenic plants by the way of integration. However, these transgenic plants after the knock out of the marker gene are still included in the scope of the transgenic plants of the present invention.

Advantages of the Invention

The invention provides a gene combination for preventing an exogenous gene from expressing in a specific tissue of a plant, and a method of breeding a transgenic plant using the gene combination. Taking rice and Bt insect-resistant genes as examples, the method can be used to breed borer-resistant transgenic rice with no expression of the transgene in endosperm, that is, there is no synthesis and accumulation of any transgenic product protein in the rice endosperm produced by the borer-resistant rice. Therefore, the public concerns about the safety for consumption of the transgenic food crops can be addressed.

The results of the experiments show that the target insect-resistant Bt gene is not expressed in the endosperm of the resulting Nipponbare heterozygous hybrid rice with the lock element and key gene, and the result of the Bt protein detection is not significantly different from the wild-type Nipponbare control (that is zero expression), while high expressions are detected in the stalk and leaf tissues that are designed for expression. Since the expression product of target gene is not detected in the rice endosperm, the inventors refer to it as Bt transgenic insect-resistant rice with no expression of the transgene in endosperm, so as to distinguish it from the traditional Bt transgenic insect-resistant rice expressing transgene in endosperm. Further insecticidal identification demonstrates the insect resistance of the Nipponbare heterozygous hybrids carrying the lock element and the key gene of the present invention (30 plants), with almost no damage in the natural *Cnaphalocrocis medinalis* outbreak. This is significantly different from the 100% damage rate for the non-transgenic controls (30 plants). The insecticidal efficiency of the plants of the present invention on the artificially inoculated (1 egg mass per plant) first instar larvae of *Chilo suppressalis* also reached the level of resistance to high resistance. Therefore, the gene combination of the present invention and the successful breeding of the transgenic insect-resistant rice with no expression of the transgene in endosperm will not only reverse the public's opposition to traditional transgenic plants expressing transgene in endosperm, but also strongly promote the industrialization process of the transgenic food crops.

The invention has a broad applicability, that is, it is suitable for the majority of crops for the purpose of fruit, seed, root and tuber, such as rice, wheat, barley, oat, maize, millet, sorghum, pearl barley, sweet potato, potato, lotus seed, soybean, and peanut and so on. These and other aspects of the invention will be better understood from the following description and appended claims.

DESCRIPTION OF DRAWINGS

FIG. 2: a flow diagram of the construction of the expression vector pKey1 of the gene key (Key1; SEQ ID NO: 5) according to one embodiment of the present invention, wherein

FIG. 3: a flow diagram of the construction of the expression vector pLY1 of the lock element (Lock1; SEQ ID NO: 8) and its linked reporter gene (eYFP) according to one embodiment of the present invention, wherein

FIG. 4: a flow diagram of the construction of the expression vector pKey2 of the key gene (Key2; SEQ ID NO: 3)

according to another embodiment of the present invention, wherein

FIG. 5: a flow diagram of the construction of the expression vector pLY2 of the lock element (Lock2; SEQ ID NO: 6) and its linked reporter gene (eYFP) according to another embodiment of the present invention, wherein

FIG. 6: a flow diagram of the construction of the expression vector pLB of the lock element (Lock1; SEQ ID NO: 8) and the target gene (cry1Ab/1Ac) according to one embodiment of the present invention, wherein

FIG. 9: the copy number analysis of the Nipponbare lines with pKey1 and pLB positive transformation, wherein.

Figure 14:
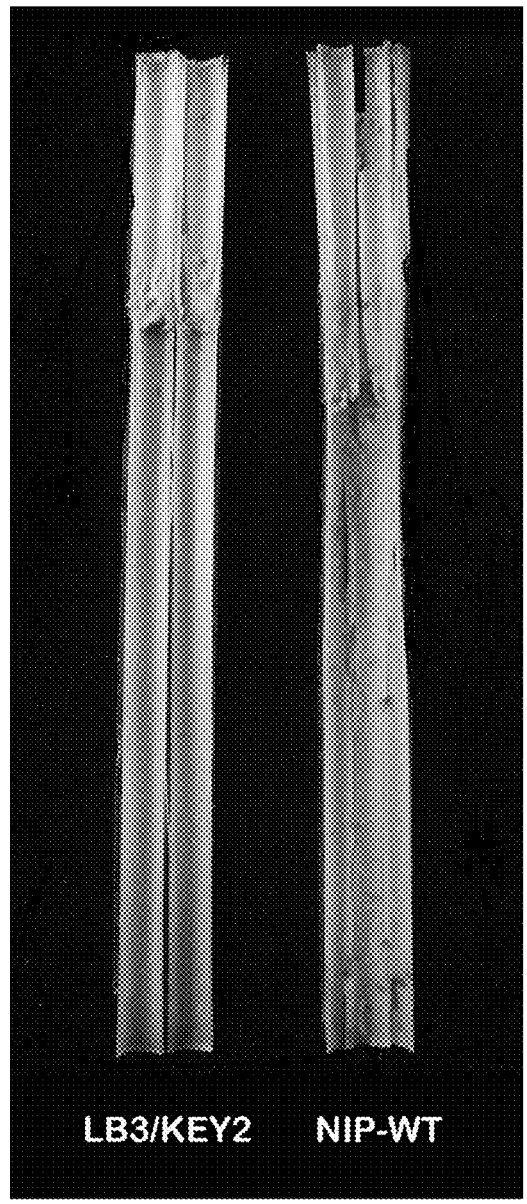

FIG. 14: the resistance of the isolated stalks of the lock element and key gene LB3/KEY2 heterozygous hybrids and wild-type Nipponbare negative control (Nip-CK) to the indoor artificially inoculated first instar larvae of Chilo suppressalis. The picture shows that no signs of infestation of Chilo suppressalis to the isolated stalks of the transgenic LB3/KEY2 heterozygous hybrids are observed, and almost all of the inoculated Chilo suppressalis are killed; while the wormholes, the chomping marks and the excretes caused by Chilo suppressalis are observed on the control stalks, and there are some alive larvae.

The invention may be better understood by reference to the following non-limiting examples, which are provided as the examples of the invention. The following examples are presented to more fully illustrate the embodiments of the invention and should not be construed as limiting the broad scope of the invention.

EXAMPLES

Example 1: Design of the Gene Combination of the Present Invention and its Feasibility Study and Verification 1. Design of the Gene Combination As mentioned above, the complete gene combination is designed to consist of two components, i.e., a lock element (Lock) capable of blocking the expression of the target gene and a key gene (Key) capable of tissue-specifically switching on the expression. For the convenience of use, two sets of such components have been designed, wherein the DNA sequences of the first set of components are SEQ ID NO: 5 (Lock1) and SEQ ID NO: 3 (Key1) respectively, and the DNA sequences of the second set of components are SEQ ID NO: 8 (Lock2) and SEQ ID NO: 6 (Key2) respectively. The lock element is designed to be placed between a constitutive expression promoter such as Actin I and the start codon of the target gene, and its function is to switch off the expression of the target gene; while the key gene is designed to be placed under the control of a green tissue-specific expression promoter such as rbcS, and its function is to switch on the expression of the target gene blocked by the lock element in a specific tissue (such as a green tissue).

In order to verify whether the above-mentioned design of gene combinations has the expected switching function, we first tested each of the components with the enhanced yellow fluorescent protein gene eYFP. Then, upon the positive results obtained, we further performed the application study using the insect-resistant Bt hybrid protein gene cry1Ab/1Ac.

Figure 1:
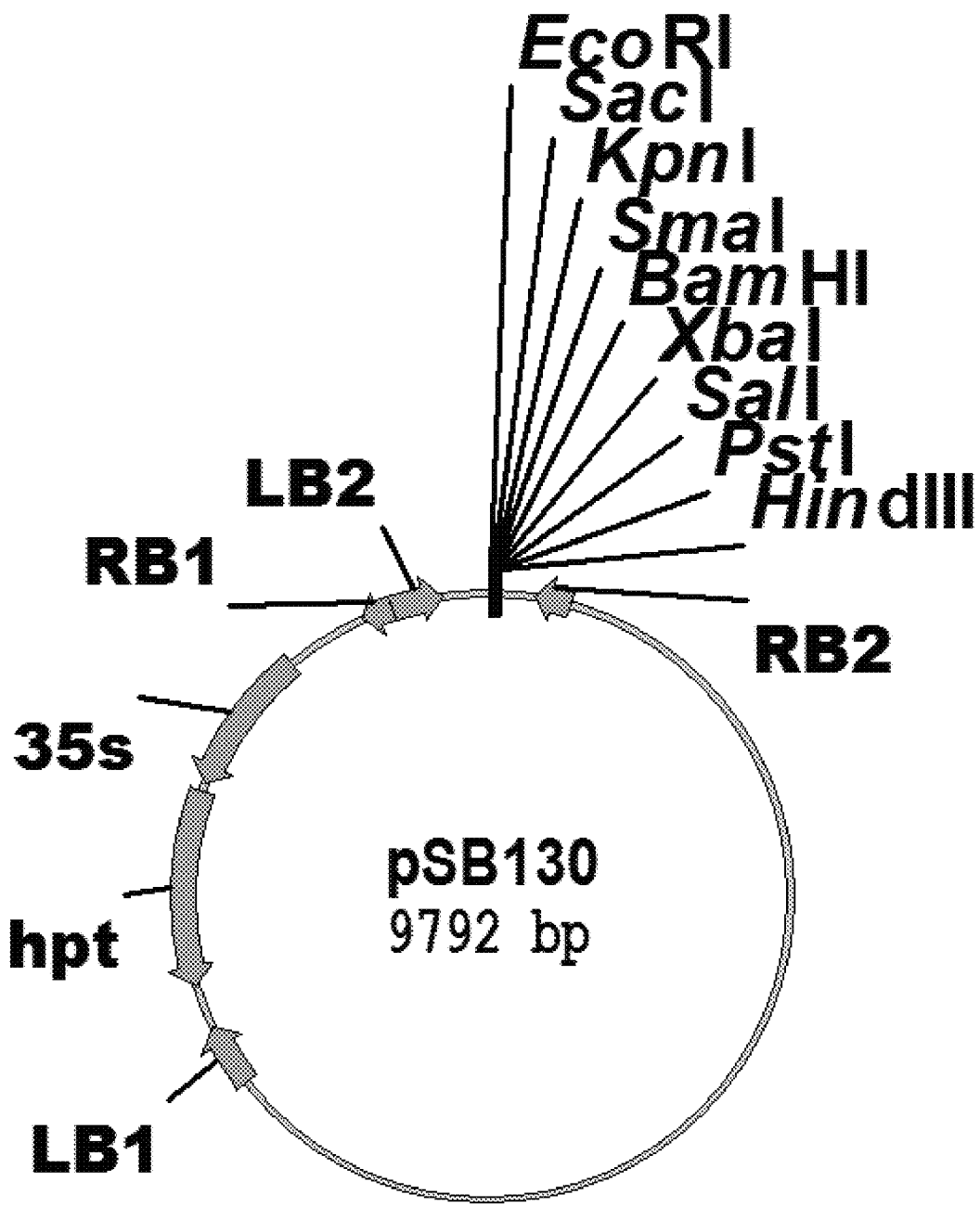
FIG. 1: Map of pSB130 plasmid vector. The plasmid vector has two T-DNA regions, wherein one carries a hygromycin B-resistant marker gene (hpt) and the other carries a multiple cloning site (MCS) for inserting a key gene or a lock element sequence linked to a target gene.
Figure 2A:
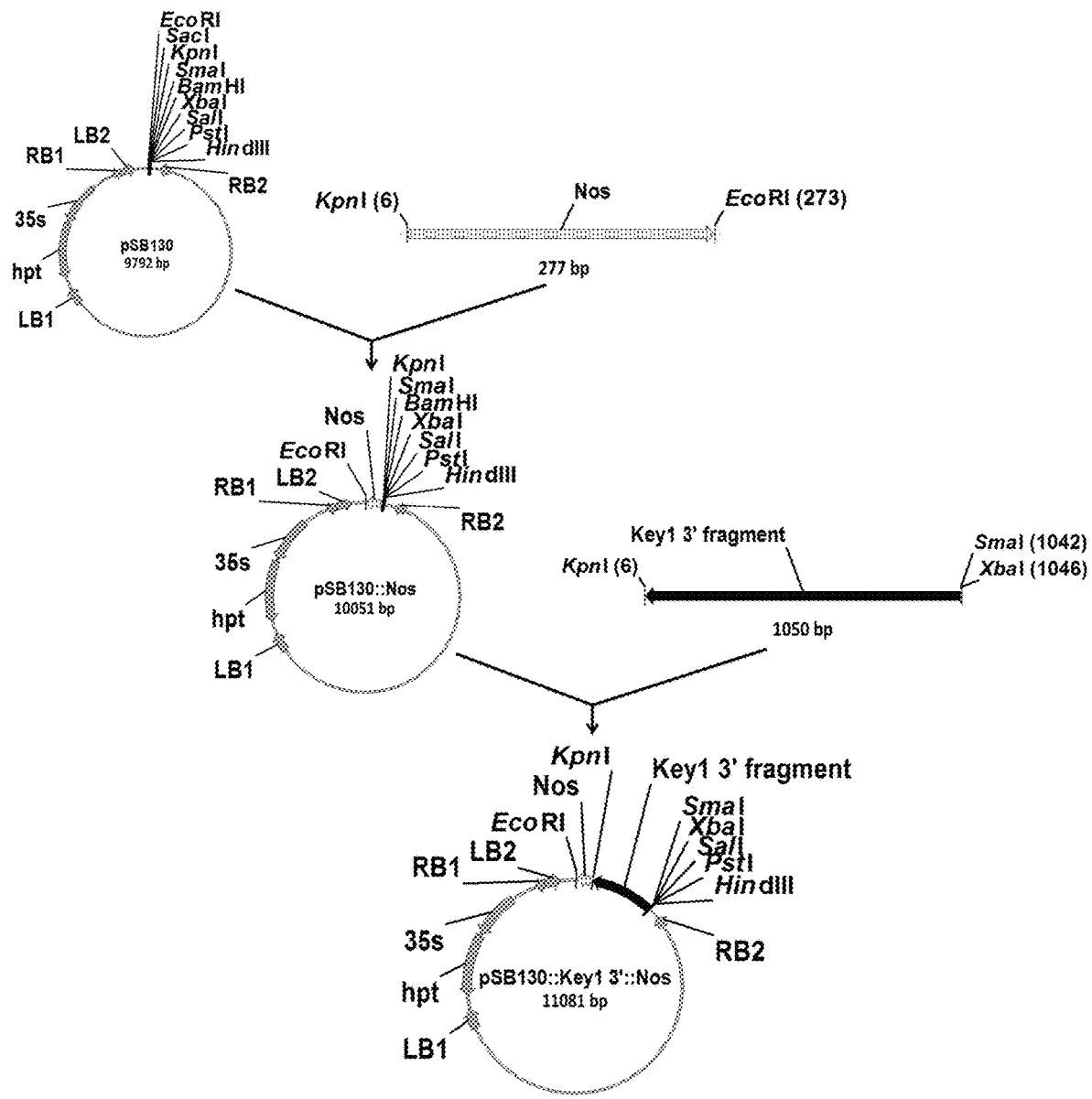
FIG. 2A shows: the first step of obtaining an NosT fragment by amplifying with the specific primers introduced with KpnI and EcoRI recognition sites and ligating it into the corresponding multiple cloning site of pSB130; and the second step of obtaining a Key1 3' fragment by amplifying with the specific primers introduced with XbaI/SmaI and KpnI recognition sites and ligating it into the corresponding multiple cloning site of pSB130.
Figure 2B:
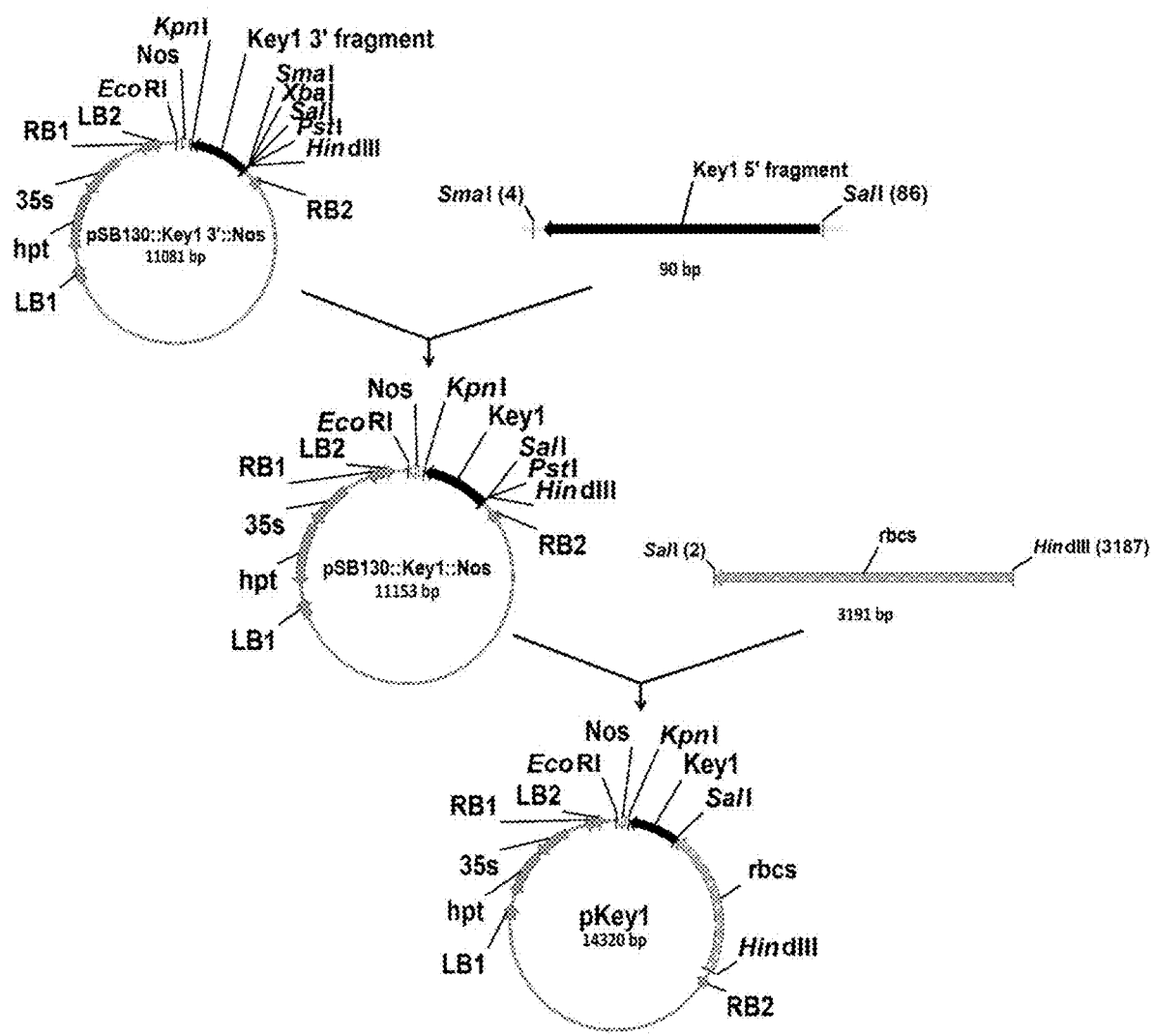
FIG. 2B shows: the third step of obtaining a Key1 5' fragment by amplifying with the specific primers with SalI and SmaI recognition sites introduced and ligating it into the corresponding multiple cloning site of pSB130; and the last step of obtaining a rbcS fragment by amplifying with the specific primers introduced with HindIII and SalI recognition sites and ligating it into the corresponding multiple cloning site of pSB130 to construct a pKey1 expression vector.
Figure 3A:
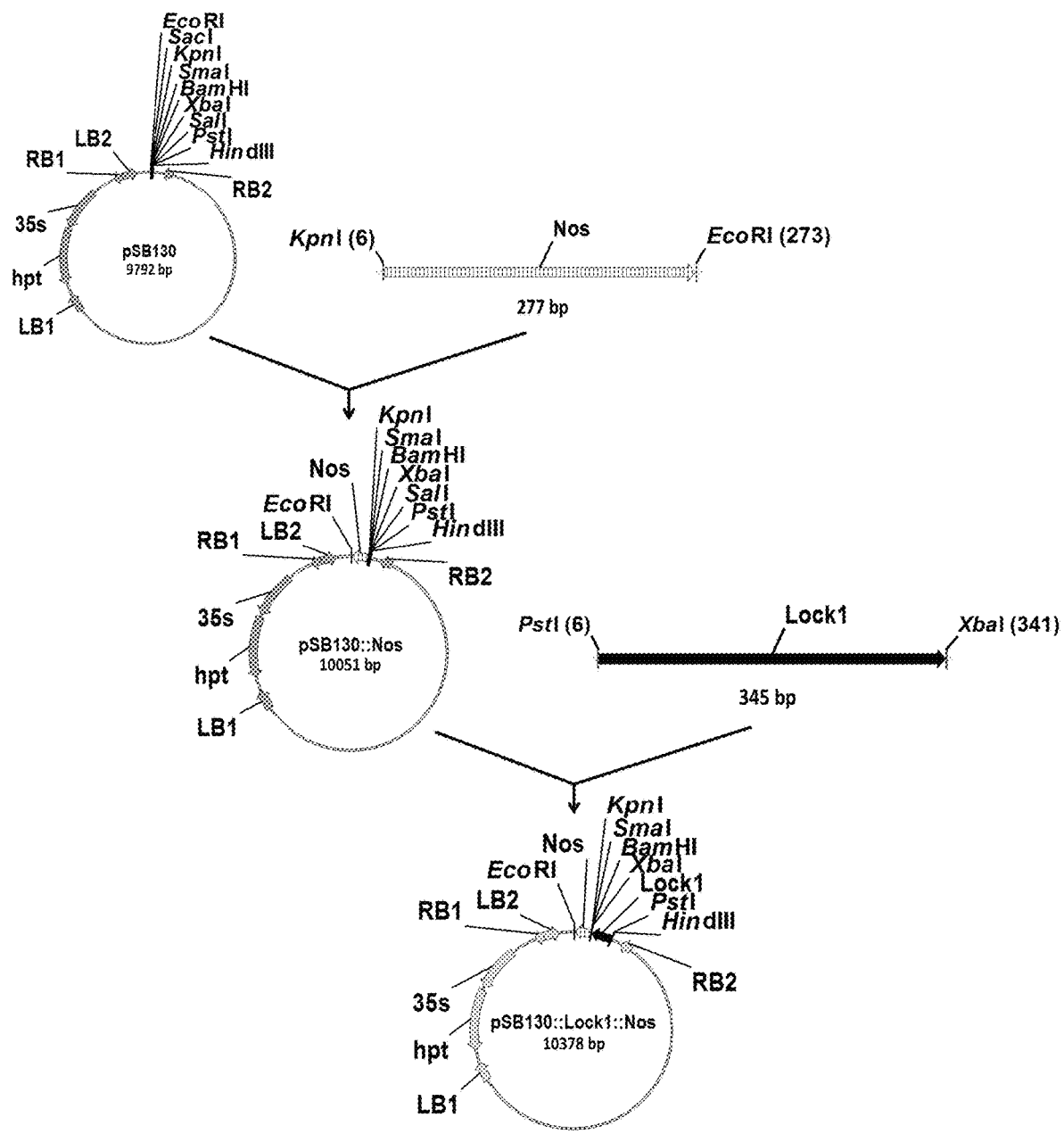
FIG. 3A shows: the first step of amplifying and cloning the NosT fragment as described for pKey1; and the second step of obtaining the Lock1 fragment by amplifying with the specific primers introduced with PstI/XbaI recognition sites and ligating it into the corresponding multiple cloning site of pSB130.
Figure 3B:
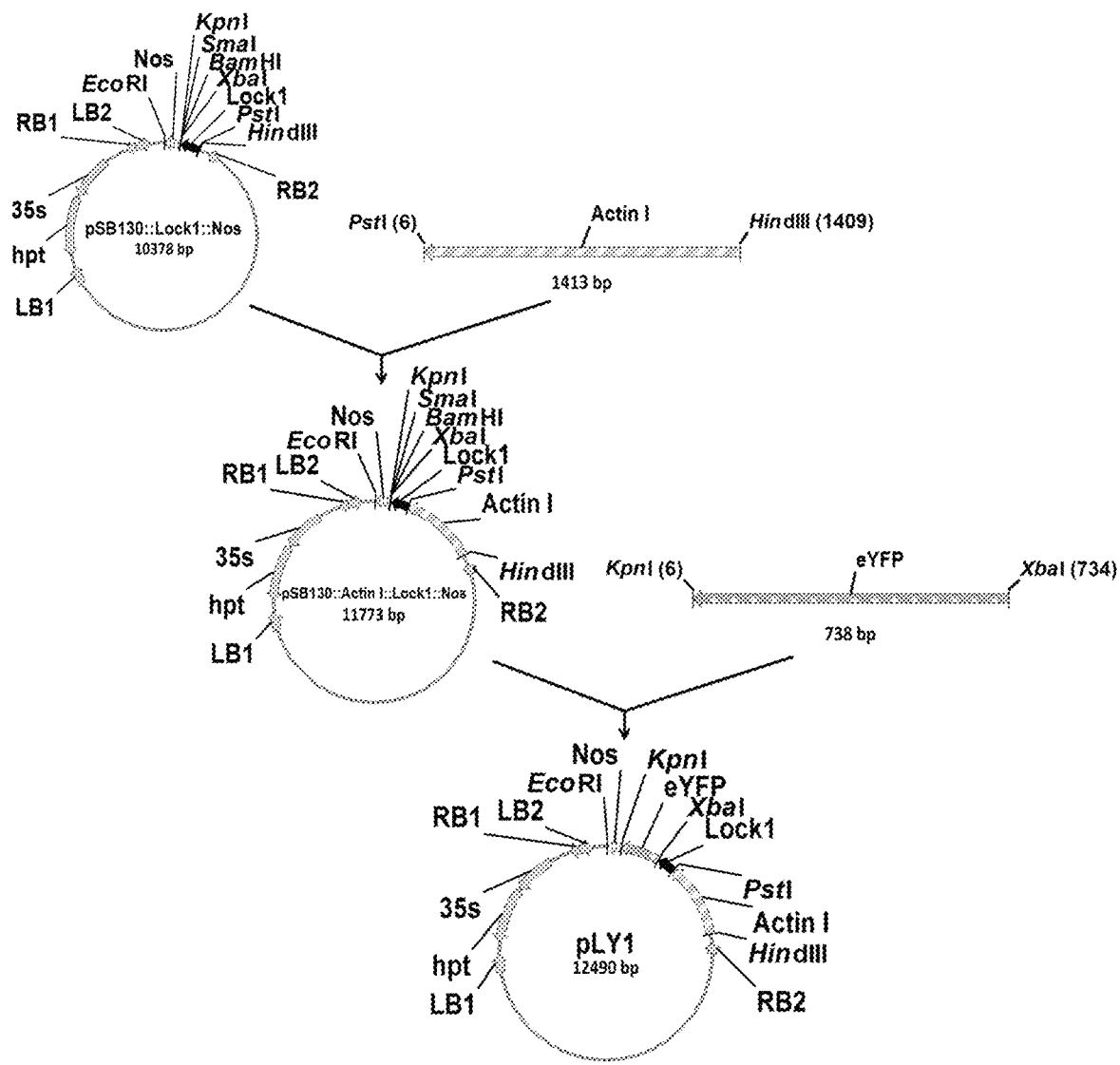
FIG. 3B shows: the third step of obtaining an ActinI fragment by amplifying with the specific primers introduced with HindIII and PstI recognition sites and ligating it into the corresponding multiple cloning site of pSB130; and the last step of obtaining an eYFP fragment by amplifying with the specific primers introduced with XbaI and KpnI recognition sites and ligating it into the corresponding multiple cloning site of pSB30 to construct a pLY1 expression vector.

2. Construction of the Validating Expression Vectors for Verifying the Switching Functions To construct the first set of expression vectors for the lock element and the key gene, all functional fragments were amplified using specific primers introduced with restriction endonuclease recognition sites (Table 1), and high-fidelity PCR technology, and these functional fragments were then ligated into the pSB130 plasmid vector according to the designed arrangement (FIG. 1), thereby obtaining the corresponding gene key expression vector pSB130::rbcS::Key1::NosT (abbreviated as pKey1) and the lock element expression vector pSB130::ActinI::Lock1::eYFP::NosT (abbreviated as pLY1). The specific construction processes are shown in FIG. 2 and FIG. 3, respectively.

Figure 4A:
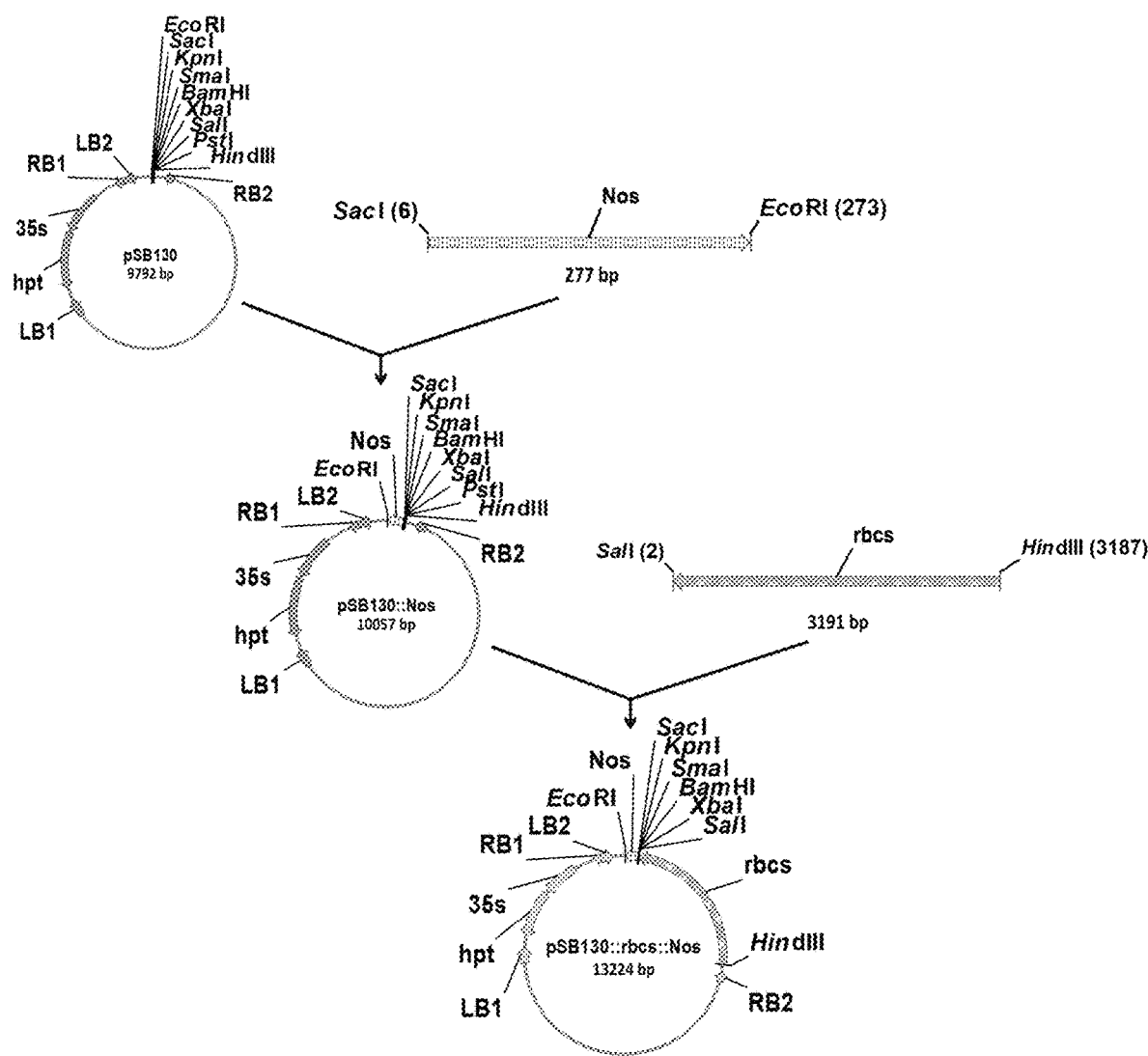
FIG. 4A shows: the first step of obtaining the NosT fragment by amplifying with the specific primers introduced with SacI and EcoRI recognition sites and ligating it into the corresponding multiple cloning site of pSB130: and the second step of obtaining the rbcS fragment by enzymatic cleavage of the pKey1 expression vector with SalI and HindIII and ligating it into the corresponding multiple cloning site of pSB130.
Figure 4B:
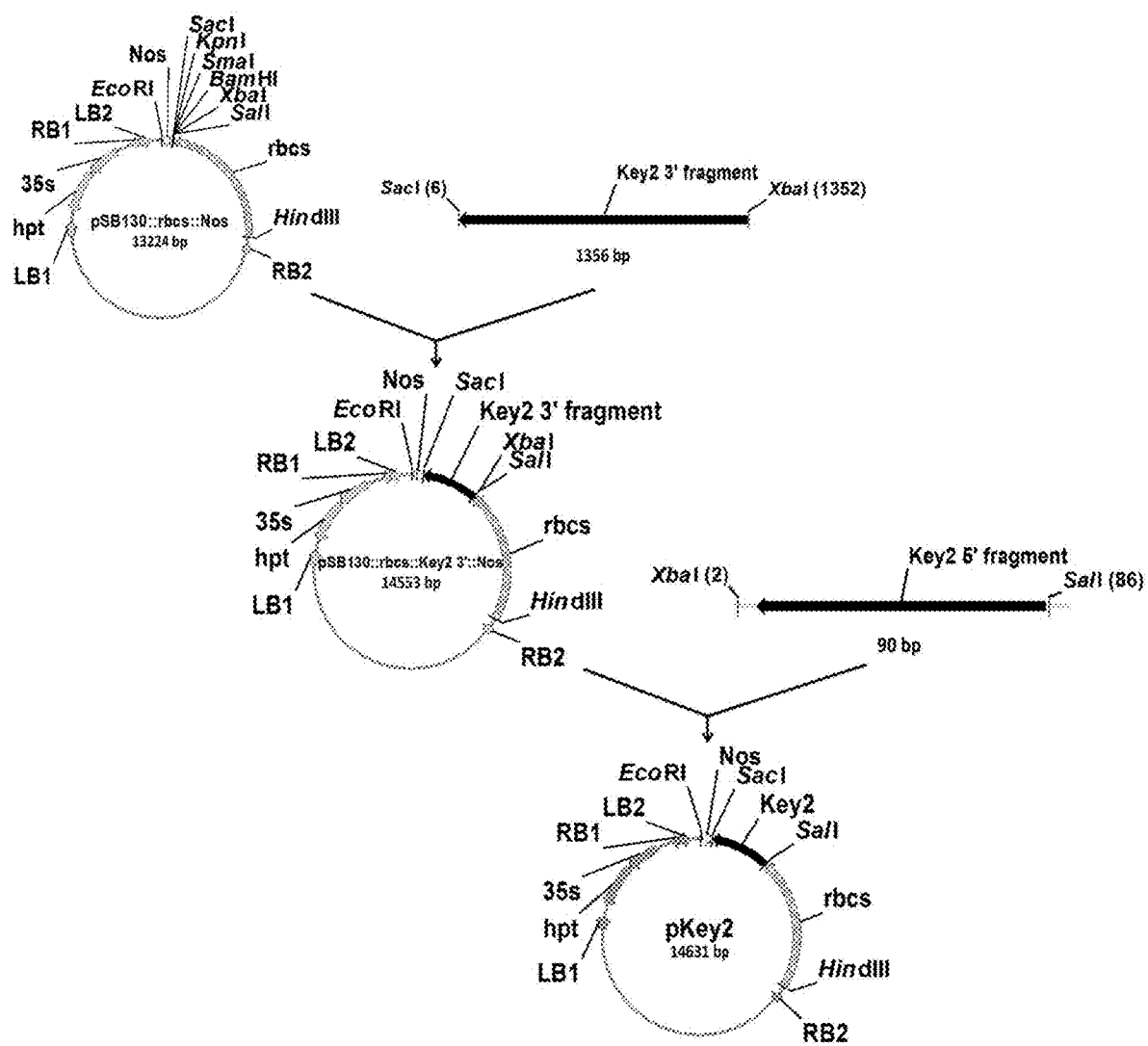
FIG. 4B shows: the third step of obtaining a Key2 3' fragment by amplifying with the specific primers introduced with SacI and XbaI recognition sites and ligating it into the corresponding multiple cloning site of pSB130; and the last step of obtaining a Key2 5' fragment by amplifying with the specific primers introduced with SalI and XbaI recognition sites and ligating it into the corresponding multiple cloning site of pSB30 to construct a pKey2 expression vector.
Figure 5A:
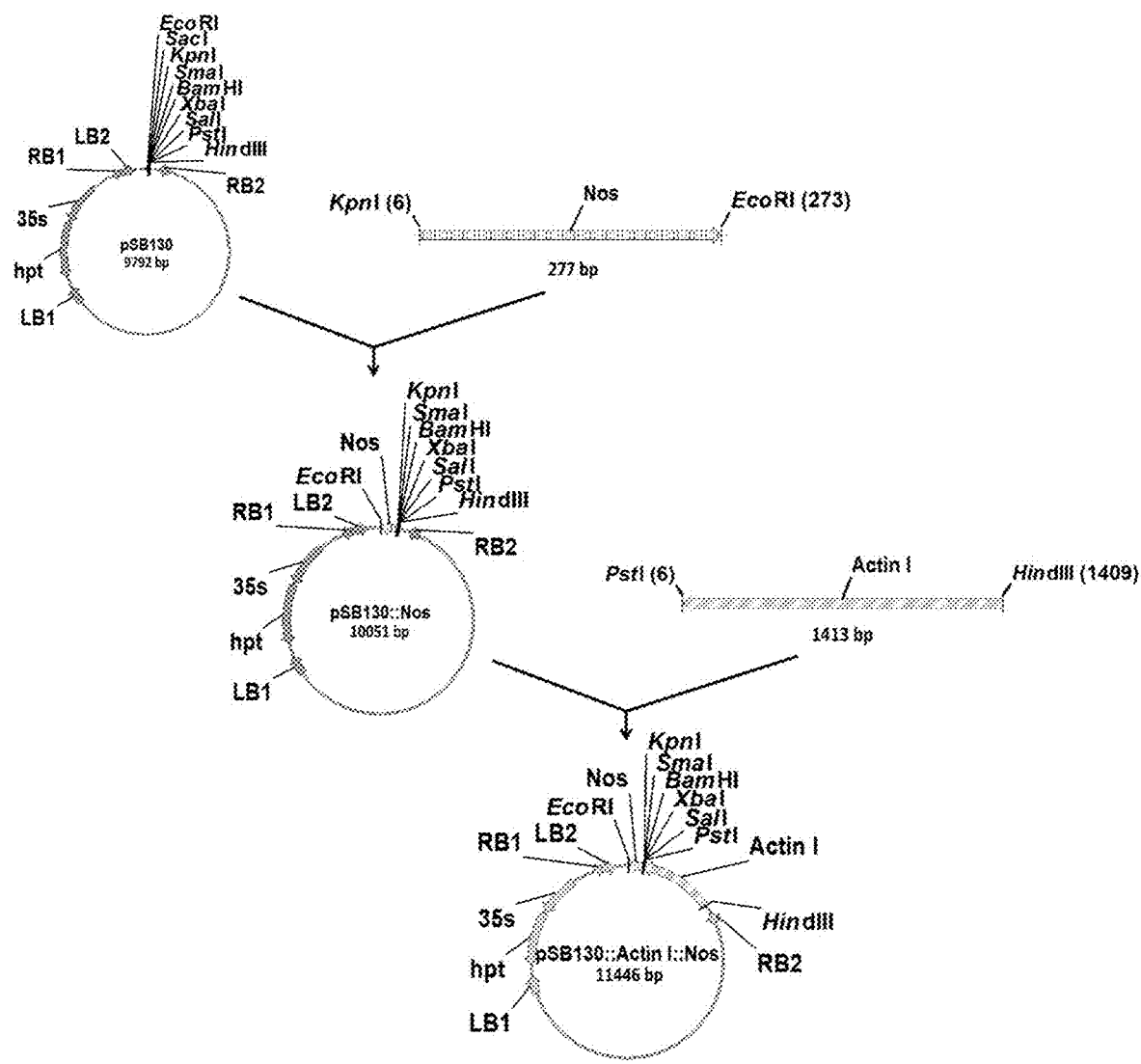
FIG. 5A shows: the first step of obtaining the Nos fragment by enzymatic cleavage of the pLY1 with KpnI and EcoRI and ligating it into the corresponding multiple cloning site of pSB130; and the second step of obtaining the ActinI fragment by amplifying with the specific primers introduced with PstI and HindIII recognition sites and ligating it into the corresponding multiple cloning site of pSB130. Figure SB shows: the third step of obtaining a Lock2 fragment by amplifying with the specific primers introduced with SaiI and PstI recognition sites and ligating it into the corresponding multiple cloning site of pSB130; and the last step of obtaining the eYFP fragment by enzymatic cleavage of the pLY1 with KpnI and SaiI and ligating it into the corresponding multiple cloning site of pSB130 to construct a pLY2 expression vector.
Figure 5B:
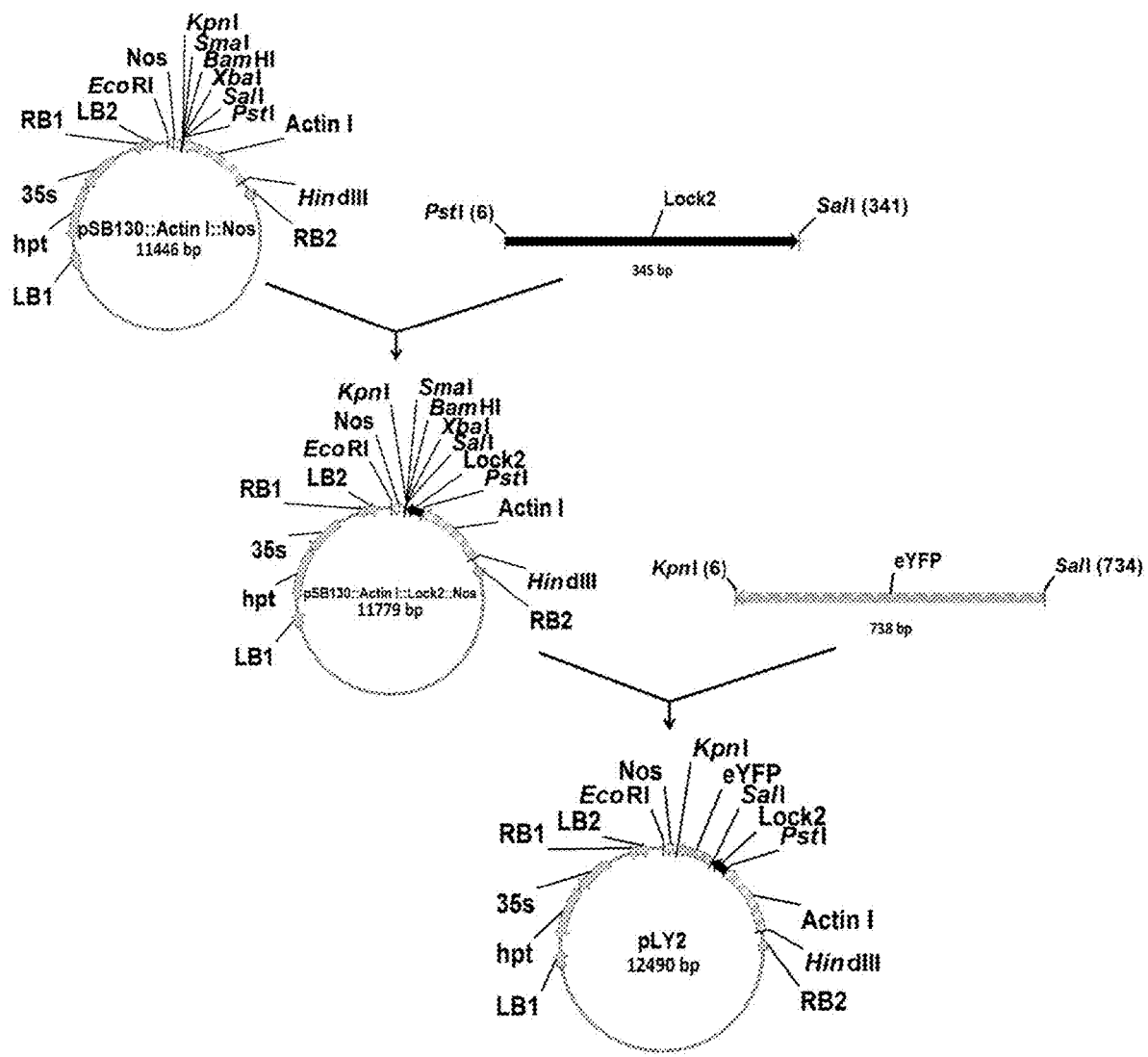

Based on the first set of expression vectors as successfully constructed, a second set of expression vectors were constructed, wherein some functional fragments were obtained from the first set of expression vectors by the enzymatic cleavage, and the other functional fragments were amplified by the specific primers (Table 1) and high-fidelity PCR amplification technology, and then ligated into the pSB130 plasmid vector according to the designed arrangement (FIG. 1), thereby obtaining the corresponding key gene expression vector pSB130::rbcS::Key2::NosT (abbreviated as pKey2) and the lock element expression vector pSB130::ActinI::Lock2::eYFP::NosT (abbreviated as pLY2). The specific construction processes of the two expression vectors are shown in FIG. 4 and FIG. 5, respectively.

3. Construction of the Applied Expression Vectors for Insect Resistance

Figure 6A:
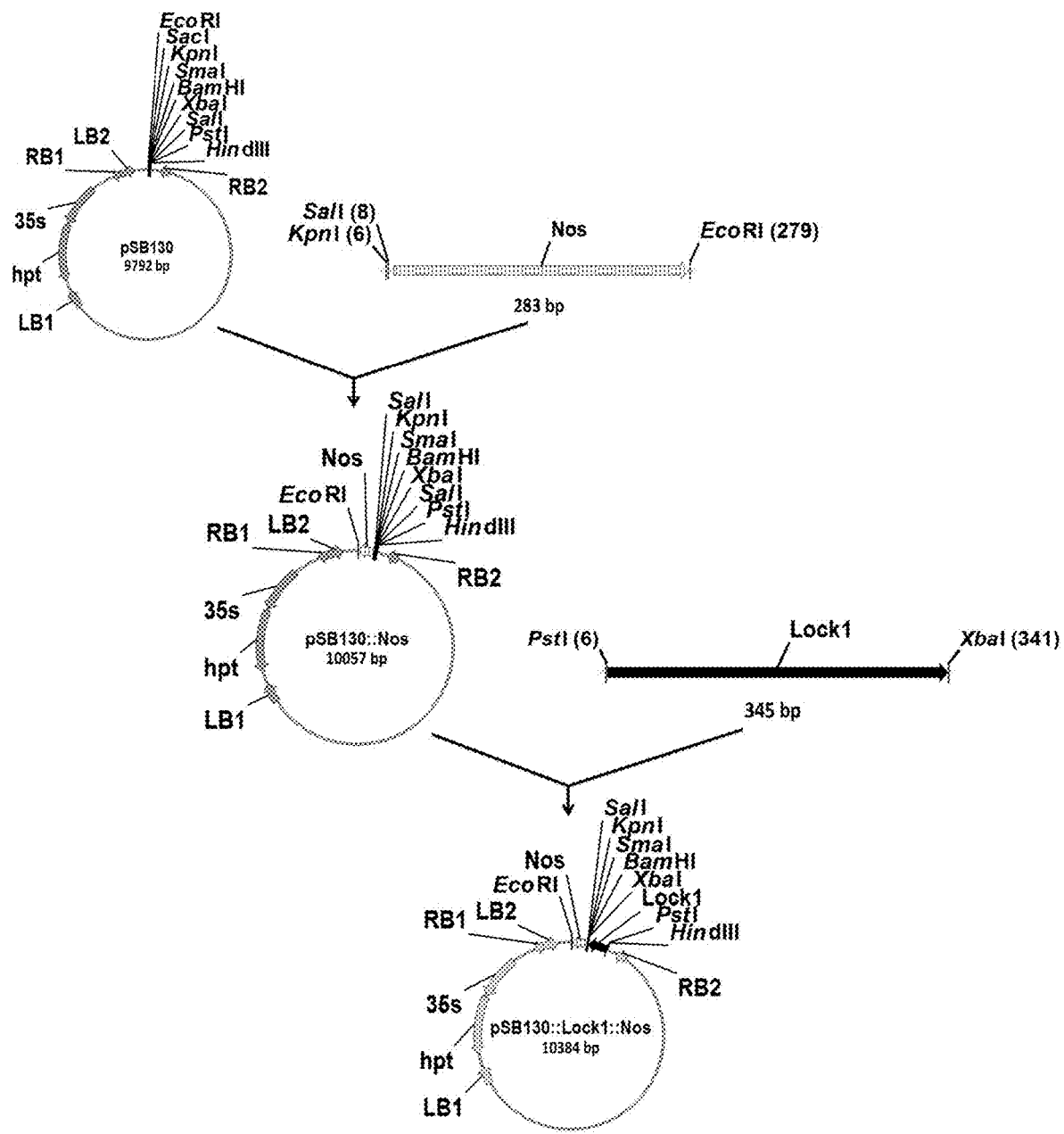
FIG. 6A shows: the first step of obtaining the Nos fragment by amplifying with the specific primers introduced with KpnI/SalI and EcoRI recognition sites and ligating it into the corresponding multiple cloning site of pSB130; and the second step of obtaining the Lock fragment by amplifying with the specific primers introduced with PsiI and XbaI recognition sites and ligating it into the corresponding multiple cloning site of pSB130.
Figure 6B:
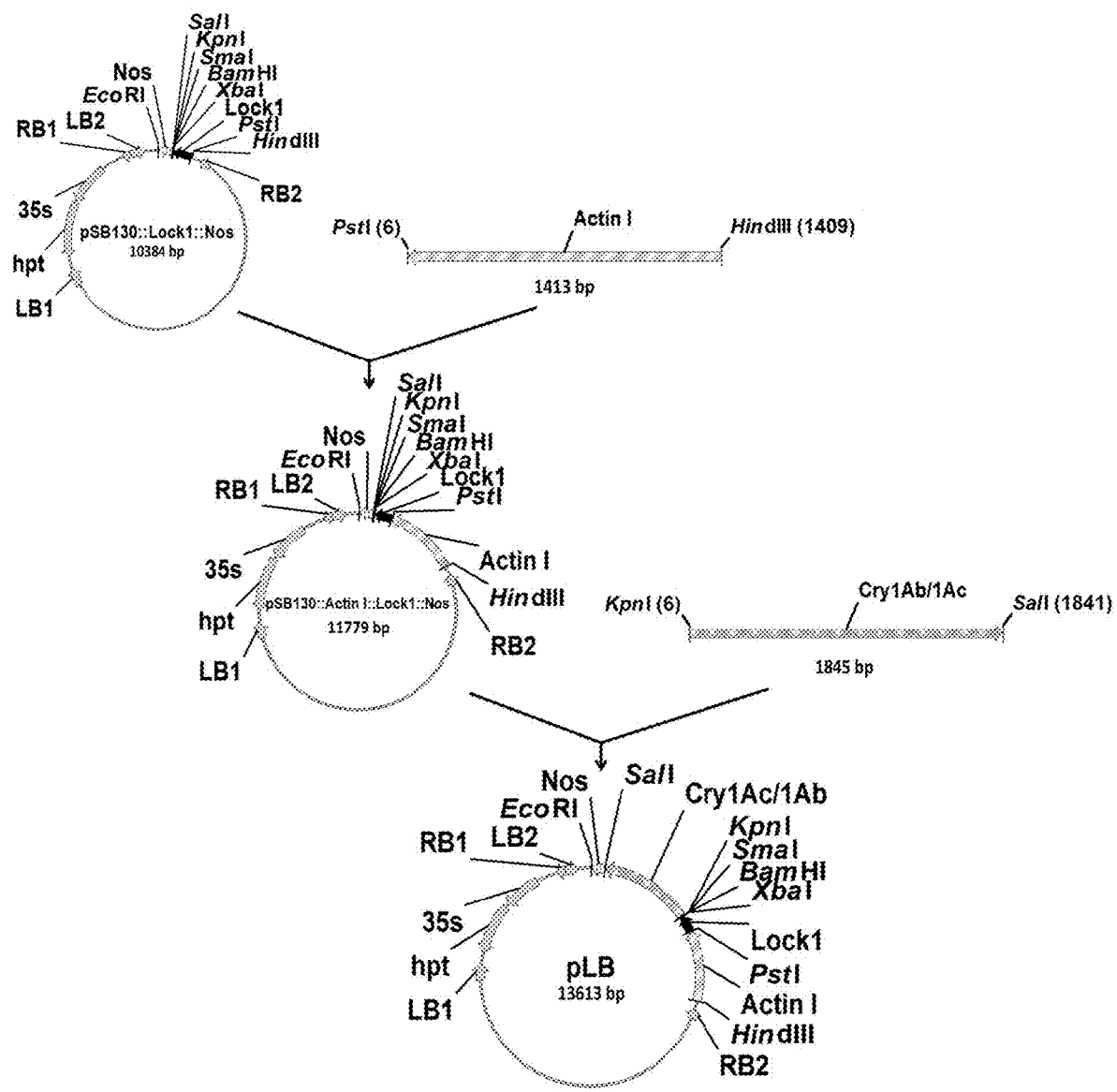
FIG. 6B shows: the third step of obtaining the ActinI fragment by amplifying with the specific primers introduced with HindIII and PsiI recognition sites and ligating it into the corresponding multiple cloning site of pSB130; and the last step of obtaining a cry1Ab/1Ac fragment by amplifying with the specific primers introduced with KpnI and SalI recognition sites and ligating it into the corresponding multiple cloning site of pSB130 to construct a pLB expression vector.

Since the validating and applied expression vectors are identical in the portion of key gene, and differ only in the fragment of target gene to which the lock element is attached, the construction of the set of the applied expression vectors is mainly performed for the lock element and the fragment of target gene. At the time of construction, on the one hand, some functional fragments common to the validating expression vectors are obtained by enzymatic cleavage, and on the other hand, the lock element in the first set of expression vectors and two insect-resistant gene functional fragments to be ligated are selected in the examples of the present invention and obtained by the specific primers (Table 1) and high-fidelity PCR amplification technology respectively, then these functional fragments are ligated into the pSB130 plasmid vector (FIG. 1) according to the designed arrangement, thereby obtaining the corresponding applied lock element expression vector pSB130::ActinI::LB1::NosT (abbreviated as pLB1). The specific construction process of the expression vector is shown in FIG. 6.

The pSB130 plasmid vector used in the examples of the present invention comprises two "T-DNA" regions, wherein one "T-DNA" region is used to carry a lock element linking to a target gene, or a key gene expression cassette, and the other is used to carry a hygromycin resistant marker gene Hpt expression cassette. The purpose of constructing the double T-DNA expression vector is to focus on future practical applications, because the transformation of the double T-DNA plasmid vector into rice can enable the possibility of the independent integration of the target gene and the marker gene in the receipt genome in order to facilitate the segregation and knock out of the marker gene by self-crossing in subsequent segregation generations.

TABLE 1

Primers, amplified functional fragments and their DNA sequences for construction of the lock element and key gene expression vectors

| Primers | Amplified functional fragment | DNA sequence |
|---|---|---|
| pKey1 | | |
| pKey1-4F | HindIII--RbcS-SalI | GATCAAGCTTCACTTAAATTTTGGTGACAGGAATGTAGTTTTCTG (SEQ ID NO: 19) |
| PKey1-4R | | GTACGTCGACCTCTGCAGCTCACCAAGCTCTCTCCTTCTTTGCTC (SEQ ID NO: 20) |
| pKey1-3F | SalI--Key 1 5'--SmaI | TCGAATGGCGGCGGTTAGGAGAAGAGAACGAGATGTGGTTGAAGAGAATGGAGTTACGACGACGACGGTGAAACGAAGGAAG (SEQ ID NO: 21) |
| pKey1-3R | | CTTCCTTCGTTTCACCGTCGTCGTCGTAACTCCATTCTCTTCAACCACATCTCGTTCTCTTCTCCTAACCGCCGCCAT (SEQ ID NO: 22) |
| pKey1-2F | XbaI-Sma I--Key1 | GATCTCTAGAGTACCCCGGGATGTCCAATTTACTGACCGTACACCAAAATTTGCCTGCATT (SEQ ID NO: 23) |
| PKey1-2R | 3'--KpnI | GTACGGTACCCTAATCGCCATCTTCCAGCAGGCGCACCATTGCCC (SEQ ID NO: 24) |
| pKey1-1F | KpnI--Nos-- | GATCGGTACCGCTAGCTCGAATTTCCCCGATCGTTCAAACATTTG (SEQ ID NO: 25) |
| pKey1-IR | EcoRI | GTACGAATTCGACACCGCGCGCGATAATTTATCCTAGTTTGCGCG (SEQ ID NO: 26) |
| pLY1 | | |
| pLY1-3F | HindIII--Actin-- | GATCAAGCTTGTCGAGGTCATTCATATGCTTGAGAAGAGAGTCGG (SEQ ID NO: 27) |
| pLY1-3R | PstI | GTACCTGCAGTCTACCTACAAAAAAGCTCCGCACGAGGCTGCATT (SEQ ID NO: 28) |
| pLY1-2F | PstI-Lock1--XbaI | GATCCTGCAGATAACTTCGTATAGCATACATTATACGAAGTTATGCTAGCTCGAATTTCCCCGATCGTTCAAACATTTG (SEQ ID NO: 29) |
| pLY1-2R | | GTACTCTAGAATAACTTCGTATAATGTATGCTATACGAAGTTATGACACCGCGCGCGATAATTTATCCTAGTTTGCGCG (SEQ ID NO: 30) |
| pLY1-4F | XbaI--eYFP-- | GATCTCTAGAATGGTGAGCAAGGGCGAGGAGCTGTTCACCGGGGT (SEQ ID NO: 31) |
| pLY1-4R | KpnI | GTACGGTACCTCAAGATCTCTTGTACAGCTCGTCCATGCCGAGAG (SEQ ID NO: 32) |
| pLY1-1F | KpnI--Nos-- | GATCGGTACCGCTAGCTCGAATTTCCCCGATCGTTCAAACATTTG (SEQ ID NO: 25) |
| pLY1-1R | EcoRI | GTACGAATTCGACACCGCGCGCGATAATTTATCCTAGTTTGCGCG (SEQ ID NO: 26) |
| pKey2 | | |
| pKey2-2F | XbaI-Key2 5'--SalI | CGAGATCTGAAGGAAGCAAAGTGGCAGCA (SEQ ID NO: 33) |
| pKey2-2R | | ACGCGTCGACTACCGCCGCCAATCCTCTT (SEQ ID NO: 34) |
| pKey2-3F | SacI-Key2 | CGAGCTCAATATACGCAGATAAAT (SEQ ID NO: 35) |
| p.Key2-3R | 3'--XbaI | CGAGATCTTACCGTAGGTATTTA (SEQ ID NO: 36) |
| pKey2-1F | EcoRI--Nos-- | GGCCTTAAGGGCTAGATCATTGTAT (SEQ ID NO: 37) |
| pKey2-1R | SacI | CGAGCTCCTTAAAGGGGCTAGCAA (SEQ ID NO: 38) |

TABLE 1-continued

Primers, amplified functional fragments and their DNA sequences for
construction of the lock element and key gene expression vectors

| Primers | Amplified functional fragment | DNA sequence |
|---|---|---|
| pLY2 | | |
| pLY2-1F | Pst--Lock2--SaI | AACTGCAGTCTTCAAGGATATGAAAGATCTCITATCCTTGAAGGGCTAGATCATTGTATCT (SEQ ID NO: 39) |
| pLY2-1R | | CGCAGCTGGAAGTTCCTATTCTCTAGAAAGTATAGGAACTTCGAATTTCCCCGATCGTTC (SEQ ID NO: 40) |
| pLY1-2F | SalI--eYFP-- | GATCGTCGACATGGTGAGCAAGGGCGAGGAGCTGTTCACCGGGGT (SEQ ID NO: 31) |
| pLY1-2R | KpnI | GTACGGTACCTCAAGATCTCTTGTACAGCTCGTCCATGCCGAGAG (SEQ ID NO: 32) |
| pLB | | |
| pLB-1F | HindIII--Actin-- | GATCAAGCTTGTCGAGGTCATTCATATGCTTGAGAAGAGAGTCGG (SEQ ID NO: 27) |
| pLB-1R | PstI | GTACCTGCAGTCTACCTACAAAAAAGCTCCGCACGAGGCTGCATT (SEQ ID NO: 28) |
| pLB-2F | PstI--Lock1--XbaI | GATCCTGCAGATAACTTCGTATAGCATACATTATACGAAGTTATGCTAGCTCGAATTTCCCCGATCGTTCAAACATTTG (SEQ ID NO: 29) |
| pLB-2R | | GTACTCTAGAATAACTTCGTATAATGTATGCTATACGAAGTTATGACACCGCGCGCGATAATTTATCCTAGTTTGCGCG (SEQ ID NO: 30) |
| pLB-3F | KpnI--cryIAb/Ac--SalI | GATCGGTACCATGGACAACAACTGCAGGCCATACAACTGCTTGAGTAACC (SEQ ID NO: 41) |
| pLB-3R | | GTACGTCGACTTATTCAGCCTCGAGTGTTGCAGTAACTGGAATGA (SEQ ID NO: 42) |
| pLB-4F | KpnI-SalI-- | GATCGGTACCGTACGTCGACGCTAGCTCGAATTTCCCCGATCGTTCAAACATTTG (SEQ ID NO: 43) |
| pLB-4R | Nos--EcoRI | GTACGAATTCGACACCGCGCGCGATAATTTATCCTAGTTTGCGCG (SEQ ID NO: 26) |

Example 2: Verification of the Functions of Switching Off/on the Expression of the Exogenous Target Gene A two-step transformation method is used for verifying the functions of switching off/on the expression of the exogenous target gene. In the first step, the two lock elements pLY1 and pLY2 in the validating expression vector prepared in Example 1 were introduced into rice embryogenic callus for persistent expression using Agrobacterium-mediated method (Liu et al., 1998). Thereafter, after several consecutive rounds (3-5 rounds, 12-14 days/round) of antibiotic screening, the resistant callus is subject to pre-differentiation (7-9 days) and differentiation culture until green spots are formed (7-9 days). In the second step, the two key genes pKey1 and pKey2 in the validating expression vectors were bombarded into the differentiated positive callus with green spots and the undifferentiated positive callus without green spots for the transient expression by the gene gun-mediated method (Tu et al., 2000). After 24-36 h, the luminescence of the yellow fluorescent protein was observed under the confocal microscopy. If the designed gene combination has complete switch functions, then the undifferentiated positive callus without green dots transformed by pKey1 and pKey2 does not fluoresce at all, and the differentiated positive callus with green dots transformed by them can fluoresce. The detailed test steps are described as follows:

1. Receipt Material

The variety used as a receipt for genetic transformation of the above validating lock elements pLY1 and pLY2 is japonica Nipponbare. This variety is the model variety of rice genetic transformation, and its mature embryo callus is easy to be induced and has high genetic transformation efficiency.

2. Medium and Composition Used in the Rice Transformation and Growth 2.1. Induction/subculture medium (per liter): 4.1 g/L N6 (Chu et al., 1975) basal salt components+N6 organic components (Table 2)+2 mg/L 2,4-dichlorphenoxy acetic acid (2,4-D)+2.0 g/L hydrolyzed casein+30 g/L sucrose+3 g/L agar, pH 5.9.

2.2. Transfection medium (per liter): AA basal medium (Table 3) (Toriyama & Hinata, 1985)+200 μM acetosyringone, pH 5.9.

2.3. Co-cultivation medium (per liter): CC basal medium (Table 4) (Hiei et al, 1994)+200 μM acetosyringone, pH 5.9.

2.4. Bacteriostatic medium (per liter): induction/subculture medium+500 mg/L cephalosporin, pH 5.9.

2.5. Screening medium (per liter): induction/subculture medium+50 mg/L hygromycin+500 mg/L cephalosporin, pH 5.9.

2.6. Regeneration medium (per liter): 4.1 g/L N6 basal salt components+N6 organic components (Table 2)+2.0 g/L hydrolyzed casein+30 g/L sucrose+6 g/L agar+2 mg/L Kinetin+1 mg/L α-naphthylacetic acid, pH 5.9.

2.7. Rice rooting medium (per liter): 2.05 g/L N6 basal salt components+½ N6 organic components (Table 2)+1.0 g/L hydrolyzed casein+15 g/L sucrose+3 g/L agar, pH 5.9.

TABLE 2

N6 basal salt components (Shanghai Shenggong) and organic components

| Basal salt components | Component concentration (mg/L) |
|---|---|
| Major elements | |
| $KNO_3$ | 2830 |
| $(NH4)_2SO_4$ | 463 |
| $KH_2PO_4$ | 400 |
| $MgSO_4 \cdot 7H_2O$ | 185 |
| $CaCl_2 \cdot 2H_2O$ | 166 |
| Trace elements | |
| $FeSO_4 \cdot 7H_2O$ | 27.85 |
| $Na_2EDTA$ | 37.25 |
| $MnSO_4 \cdot H_2O$ | 4.4 |
| $ZnSO_4 \cdot 7H_2O$ | 1.5 |
| $H_3BO_3$ | 1.6 |
| KI | 0.8 |
| Organic components | |
| Inositol | 100 |
| Glycine | 2.0 |
| Niacin | 0.5 |
| Pyridoxine | 0.5 |
| Thiamine | 1.0 |

TABLE 3

Formula of AA medium

| Stock liquor | Basal medium components | Concentration of the components in the stock liquor (g/L) | the amount of stock liquor added/liter |
|---|---|---|---|
| | Major element components | | |
| I | KCl | 58.8 | take 50 mL |
| | $MgSO_4 \cdot 7H_2O$ | 7.4 | to 1 L |
| | $CaCl_2 \cdot 2H_2O$ | 8.8 | |
| | $KH_2PO_4$ | 3.4 | |
| | Trace element components | | |
| II | $MnSO_4 \cdot H_2O$ | 1.69 | takel 10 mL |
| | $ZnSO_4 \cdot 7H_2O$ | 0.86 | to 1 L |
| | $H_3BO_3$ | 0.62 | |
| | KI | 0.083 | |
| | $CuSO_4 \cdot 5H_2O$ | 0.0025 | |
| | $CoCl_2 \cdot 6H_2O$ | 0.0025 | |
| | $Na_2MoO_4 \cdot 2H_2O$ | 0.025 | |
| | Organic components | | |
| III | Inositol | 10.0 | take 10 mL |
| | Arginine | 22.8 | to 1 L |
| | VB5 | 0.05 | |
| | Aspartic acid | 26.6 | |
| | VB1 | 0.01 | |
| | VB6 | 0.05 | |
| | Glycine | 7.5 | |
| | Glutamine | 87.7 | |

AA basal + sucrose 30 g/L + glucose 10 g/L + hydrolyzed casein 0.5 g/L + 2,4-D 2 mg/L pH 5.9

TABLE 4

Formula of CC medium

| Stock liquor | Basal medium components | Concentration of the components in the stock liquor (g/L) | the amount of stock liquor added/liter |
|---|---|---|---|
| | Major element components | | |
| I | $NH_4NO_3$ | 12.80 | take 50 mL |
| | $KNO_3$ | 24.24 | to 1 L |
| | $MgSO_4 \cdot 7H_2O$ | 4.94 | |
| | $KH_2PO_4$ | 2.72 | |
| | $CaCl_2 \cdot 2H_2O$ | 11.76 | |
| | Trace element components | | |
| II | $MnSO_4 \cdot H_2O$ | 1.116 | takel 10 mL |
| | $ZnSO_4 \cdot 7H_2O$ | 0.576 | to 1 L |
| | $H_3BO_3$ | 0.310 | |
| | KI | 0.084 | |
| | $CuSO_4 \cdot 5H_2O$ | 0.0025 | |
| | $CoCl_2 \cdot 6H_2O$ | 0.0028 | |
| | $Na_2MoO_4 \cdot 2H_2O$ | 0.024 | |
| | Organic components | | |
| III | Inositol | 9.00 | take 10 mL |
| | VB5 | 0.60 | to 1 L |
| | VB1 | 0.85 | |
| | VB6 | 0.10 | |
| | Glycine | 0.2 | |
| | 100X Fe-salt | | |
| IV | $FeSO_4 \cdot 7H_2O$ | 2.785 | take 10 mL |
| | $Na_2$-EDTA | 3.725 | to 1 L |

CC basal + sucrose 20 g/L + mannitol 36.43 g/L + hydrolyzed casein 50 mg/L + 2,4-D 2.0 mg/L + glucose 10.0 g/L + agar 3.0 g/L, pH 5.9

3. Transformation of the Lock Element

As described above, the genetic transformation of the validating lock element expression vectors pLY1 and pLY2 was carried out using the *Agrobacterium*-mediated method. The *Agrobacterium* strain used is EHA105 (BioVector NTCC Inc.), and the recipient cell used was Nipponbare mature embryo-induced embryogenic callus. The specific steps of *Agrobacterium* transformation are as follows.

3.1 Induction of Rice Embryogenic Callus

Several mature Nipponbare seeds were taken and shelled. The full-grained, good embryo unrefined rice were placed into a pre-autoclaved beaker, soaked in 70% alcohol for 1 min under continuous shaking to remove the surface impurities; then soaked and sterilized with 20% sodium hypochlorite for 20 min (while shaking on a shaker if required); then rinsed with sterile distilled water for 4 to 5 times to dilute and remove the sodium hypochlorite remaining on the surface of the unrefined rice. The aseptically treated unrefined rice were inoculated on MS callus induction and subculture medium containing 2.0 mg/L 2,4-D (Table 2), and cultured at 28° C. in dark for about 2 weeks until a suitable size of nascent callus was produced at the scutellum of mature embryos. Thereafter, the nascent callus was cut and transferred to fresh callus induction and subculture medium, subcultured under the same conditions, subcultured every 2 weeks until the embryogenic callus with the thick cytoplasm, the bright yellow color, the hard texture and the granular cell mass was formed.

3.2 Genetic Transformation and Shake Culture of *Agrobacterium* Strain EHA105

0.5 μL the expression vector plasmid was added into a 1.5 mL centrifuge tube containing 60 μL electrocompetent *Agrobacterium* EHA105, mixed uniformly with the pipette and transferred into the electrode cuvette. After the electroporation, 1 mL LB liquid medium was quickly added, mixed uniformly with the pipette and then transferred to the previous 1.5 mL centrifuge tube and shaken for 1 h at 28° C. in a shaker. After the recovery of the strain, 100 μL strain solution was pipetted and uniformly plated onto the surface of LB solid screening (containing 50 mg/L kanamycin, 25 mg/L rifampicin) medium (Shanghai Shenggong), and cultured at 28° C. for 2 days. After verification of the positive colonies by PCR, the positive clones were cultured by shaking, and the resulting strain solutions were stored at 50% glycerol concentration and −80° C. for future use.

3.3 *Agrobacterium* Transfection and Subscreening of the Rice Callus

The *Agrobacterium* transfection was carried out according to the procedure reported by Yang et al., (2011). The specific procedure is as follows: the *Agrobacterium* solution stored at −80° C. was thawed, and 200 μL of the solution was uniformly plated onto the surface of the LB solid medium containing 25 mg/l rifampicin and 50 mg/L kanamycin and cultured at 28° C. overnight. The single colonies were picked and expanded with LB liquid medium. Thereafter, 200-300 μL of the fresh strain solution was removed and inoculated into 20 mL of the LB liquid culture containing 25 mg/L rifampicin and 50 mg/L kanamycin, and cultured under shaking (220 rpm) at 28° C. for 16-18 h. A sufficient amount of the strain solution was centrifuged at 4000 rpm for 15 min, and the supernatant of the LB medium was discarded. The *Agrobacterium* was resuspended by adding 20 mL 0.1 M $MgSO_4$ solution (slightly pipetted with a pipette), and centrifuged at 4000 rpm for 10-15 min. The $MgSO_4$ supernatant containing antibiotics was discarded. The *Agrobacterium* was resuspended by further adding 5 mL AA transfection medium containing 200 μM Acetosyringone (AS) (Table 3), and an appropriate amount of AA-AS transfection medium was added, so that the $OD_{600}$ value of the strain solution was finally adjusted to be between 0.8 and 1.0. After the concentration adjusting, the strain solution was dispensed in sterile 50 mL centrifuge tubes (20-25 mL/tube), until the future use.

Before the *Agrobacterium* transfection, the embryogenic callus was firstly pre-cultured for about 7 days, and then transferred from the subculture dish to an empty culture dish covered with a sterile filter paper, and air-dried on the ultra-clean workbench for about 10-15 minutes, during which, the callus was fully dried by slowly tumbling it with a sterilized spoon. After drying, it was transferred to a centrifuge tube containing the strain solution, and gently shaken at room temperature for 40 min, and the centrifuge tube was settled on the superclean workbench for 10 min. The strain solution was discarded, and the embryogenic callus was placed on the sterile filter paper and dried for about 15 min, then it was transferred to the CC co-cultivation medium (Table 4) containing AS (200 μM) with the surface covered with a sterile filter paper, and cultured in dark at 28° C. for 50-55 h. The embryogenic callus without the significant growth of the *Agrobacterium* or contaminated *Agrobacterium* on the surface was transferred onto the N6 bacteriostatic medium containing 2.0 mg/L 2,4-D, 500 mg/L Cefortaxim, and was bacteriostatic cultured in dark at 28° C. for 3-4 d. After the bacteriostatic culture, the callus was then transferred to the screening medium containing 500 mg/L cephalosporin and 50 mg/L Hygromycin, and cultured in dark at 28° C. The callus in the good growth state was picked for subculture every half month and the concentration of cephalosporin in the culture was adjusted according to the degree of contamination. In general, the concentration can be considered to be halved in the third or fourth round subculture. Such subculture was continued until a resistant callus with the rapid growth, large amount, and vivid color was obtained (4-6 rounds of screening and subculture).

3.4 the Differentiation Culture of the Resistant Callus

The resistant callus obtained in the above step was transferred to N6 regeneration medium, and was pre-differentiated in the dark chamber at 28° C. for one week, then transferred onto a fresh N6 regeneration medium, and cultured in a light chamber for differentiation at 25° C. until green dots were formed (requiring about two weeks).

4. Key Gene Transformation

Using the callus with the green dots formed in the above step as a receptor, the validating key gene expression vectors pKey1 and pKey2 prepared according to Example 1 were introduced into the differentiated callus with green dots and the undifferentiated callus without green dots by using the gene gun-mediated method described in Tu et al. (2000) for transient expression. After 24 to 36 h of the recovery culture, the fluorescence signal of the yellow fluorescent protein was observed under a confocal microscope and photographed and stored.

5. Experimental Results

Figure 7:
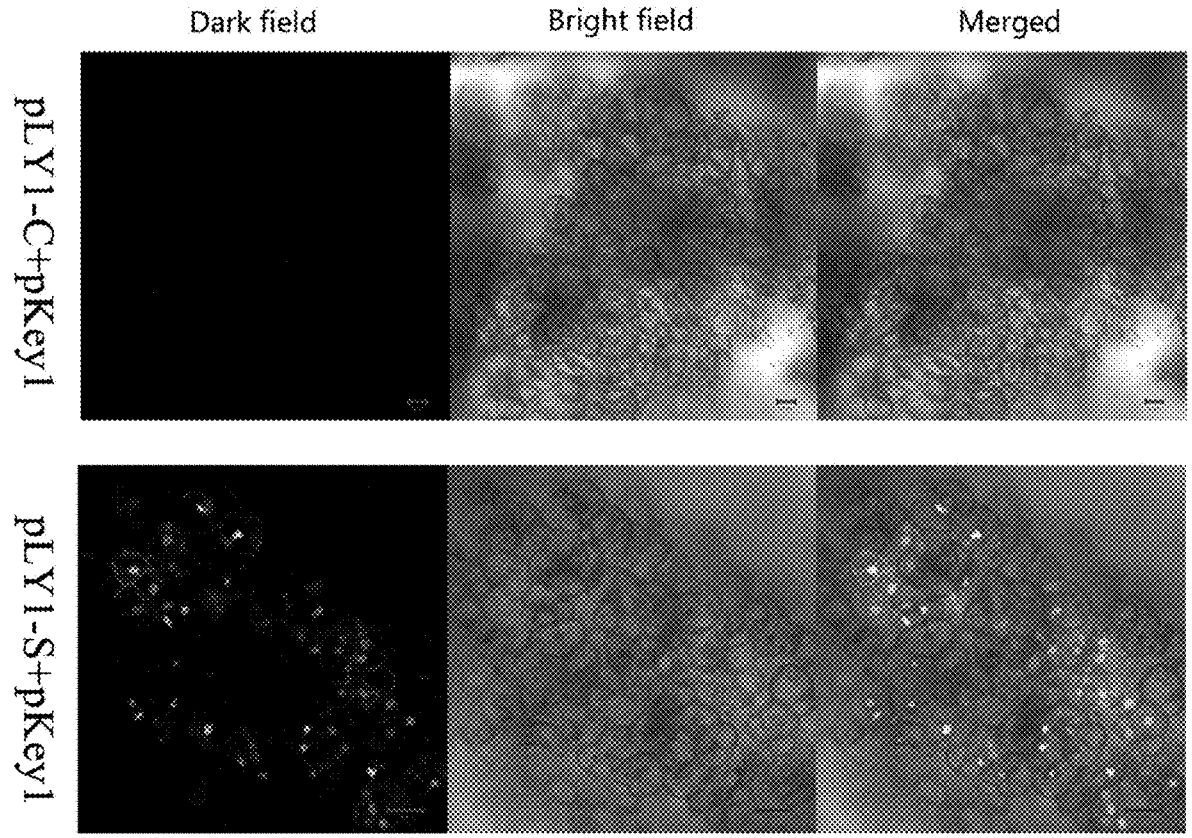
FIG. 7: a graphical representation of the functional verification of a set of lock element and key gene according to one embodiment of the present invention, wherein pLY1-C+pKey1 is the observation results under the confocal microscopy of the undifferentiated pLY1 positive callus without green dots after the re-transformation and transient expression of the key gene pKey1, wherein no fluorescence signal is observed under the dark field condition; and pLY1-S+pKey1 is the observation results under the confocal microscopy of the differentiated pLY1 positive callus with green dots after the re-transformation and transient expression of the key gene pKey1, wherein the fluorescence signal is observed under the dark field condition. In the figure, the line segment=20 µM.
Figure 8:
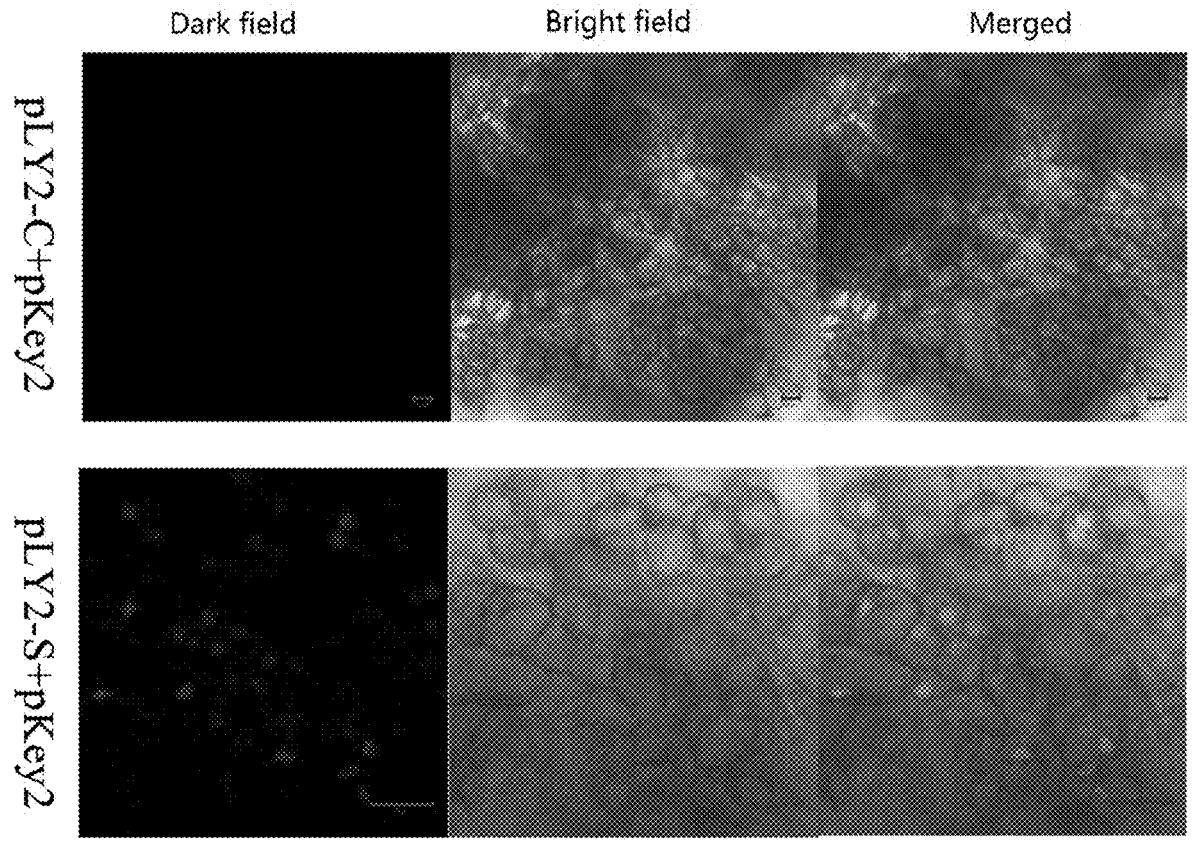
FIG. 8: a graphical representation of the functional verification of a set of lock element and key gene according to another embodiment of the present invention, wherein pLY2C+pKey2 is the observation results under the confocal microscopy of the undifferentiated pLY2 positive callus without green dots after the re-transformation and transient expression of the key gene pKey2, wherein no fluorescence signal is observed under the dark field condition; and pLY2-S+pKey2 is the observation results under the confocal microscopy of the differentiated pLY2 positive callus with green dots after the re-transformation and transient expression of the key gene pKey2, wherein the fluorescence signal is observed under the dark field condition. In the figure, the line segment=20 µM.

The test results are shown in FIGS. 7 and 8. As can be seen from the figures, under the confocal microscope, there is no fluorescence signal observed for the undifferentiated (without green spots) pLY1 and pLY2 positive callus upon retransformation and transient expression of the key gene expression vectors pKey1 and pKey2, while the fluorescence signal can be observed only in the differentiated (having green spots) pLY1 and pLY2 positive callus upon retransformation and transient expression of the key gene expression vectors pKey1 and pKey2. These test results thus confirm that both sets of gene combination as designed can properly and effectively switching off/on the gene expression.

Example 3: Construction of the Applied Lock Element and Key Gene Transformation Lines and Production of the Heterozygous Hybrid The genetic transformation of the applied lock element and key gene was carried out using the *Agrobacterium*-mediated method. Excepting using of the applied lock element expression vector pLB1 and the key gene expression vector pKey1 prepared according to Example 1, the selection of the receipt material, the various media used, the genetic transformation of the vector and the pre-differentiation and differentiation cultures of the positive resistant callus were all identical to the corresponding test procedures described in Example 2 until the positive resistant callus was differentiated into green seedlings. After washing away the medium on the root system, the resulting green seedlings were transferred into the Yoshida medium (Table 5) for the intermediate culture, either directly (for the plants having roots and buds differentiated at the same time) or after fully rooting in the N6 rooting medium (for the plants having the buds differentiated firstly). After the growth state was good and stable, it was transplanted to the greenhouse until it was mature.

TABLE 5

The formula of the Yoshida nutrient solution (Yoshida, 1976)

| Stock liquor | Components | Concentration of the components in the stock liquor (g/10 L) | the amount of stock liquor added/4 liters |
|---|---|---|---|
| A | NH$_4$NO$_3$ | 914.0 | 5 |
| B | NaH$_2$PO$_4$ · 2H$_2$O | 403.0 | 5 |
| C | K$_2$SO$_4$ | 714.0 | 5 |
| D | CaCl$_2$ | 886.0 | 5 |
|   | MgSO$_4$ · 7H$_2$O | 3240.0 | |
|   | MnCl$_2$ · 4H$_2$O | 15.0 | |
|   | (NH$_4$)$_6$Mo$_7$O$_{24}$ · 4H$_2$O | 0.74 | |
|   | H$_3$BO$_3$ | 9.34 | |
| E | ZnSO$_4$ · 7H$_2$O | 0.35 | 5 |
|   | CuSO$_4$ · 5H$_2$O | 0.31 | |
|   | FeCl$_3$ · 6H$_2$O | 77.0 | |
|   | Citric acid (monohydrate) | 119.0 | |
|   | pH | 5.0 | |

After the genetic transformation of the above steps, 42 pKey1 independent transformants and 59 pLB1 independent transformants were obtained. Thereafter, the selections of the homozygous lines were carried out on each of the two groups of the independent transformants, and the production of the heterozygous hybrids between the two groups of the independent transformants and the insect resistance identification were performed. The details are as follows.

Example 4: Molecular Analysis of the Applied Lock Element and Key Gene Transformation Lines 1. DNA Extraction
1.1 DNA Mini-Extraction A fresh leaf (length of 2-3 cm) was removed from the transgenic plants obtained according to Example 3, placed in a mortar, added 500 μL of 1.5×CTAB extraction solution, and ground to homogenate. The homogenate was transferred to a 1.5 mL centrifuge tube, incubated in a 56° C. water bath for 20 min, then add 500 μL chloroform:isopentanol (24:1), and mixed thoroughly (upside down for several times), centrifuged at room temperature for 5 min (14,000 r/min). 300 ul of the supernatant was added to 600 μL anhydrous ethanol (precooled at −20° C.), mixed uniformly and placed at −20° C. for more than 30 min, and centrifuged at room temperature for 5 min (14,000 r/min). The supernatant was discarded and the DNA pellet was washed with 75% ethanol. Thereafter, the ethanol was discarded, the DNA pellet was air-dried at room temperature, and finally dissolved in 200 μL of sterile water for use.

1.2 DNA Maxi-Extraction 3-5 adult rice leaves (3-5 g) were removed, added liquid nitrogen and rapidly ground to powder form, transferred to a pre-cooled 50 mL centrifuge tube, immediately added 15-20 mL preheated boiling 1.5×CTAB, shaken uniformly and placed in a 56° C. water bath for 30 min. Then one volume of an extraction solvent (chloroform:isopentanol at 24:1) was added, spun gently for 30 min until the solution is separated into three layers, with the upper, middle and lower lays being yellow, green and black respectively. It was centrifuged at 4000 rpm for 20 minutes at room temperature (temperature>18° C.), the supernatant was removed and added 1/10 volume of 56° C. preheated 10×CTAB, and shaken uniformly. Again, one volume of the extraction solvent (chloroform:isopentanol at 24:1) was added and spun gently for 30 min. It was centrifuged at 4000 rpm for 20 min at room temperature (temperature>18° C.), then the supernatant was discard with a 5 mL pipette tip and added one volume of 1×CTAB. After spin, flocculent DNA formed was picked up with the tip and transferred into the bottom of a 1.5 mL centrifuge tube, which was placed upside down and dried for 10 min on absorbent paper. Then 10 μL RNase and 0.5 ml sterilized 1 M NaCl were added and dissolved at room temperature or in a 56° C. water bath. The dissolved DNA was added to a 2 volumes (−20° C.) of −20° C. pre-cooled 95% ethanol. The flocculent DNA formed was precipitated by spin, and placed into a 1.5 mL centrifuge tube with a pipette tip, added 1.5 mL of 75% ethanol to wash the DNA, then the ethanol was discarded, added ultrapure water and stored at 4° C. for use.

2. Detection of the Positive Transgenic Plants and Identification of the Homozygous Lines The detection of the positive transgenic plants and identification of the homozygous lines were performed using PCR techniques. Since the Hpt marker gene and the lock element or key gene were co-transformed by double T-DNA, the identification of the TO generation positive transformation line was based on the target gene only. Therefore, after the detection, only the plants positive for the target gene were cultivated to mature, and the non-positive plants were all discarded to reduce the workload of the subsequent generations.

The primers used for amplifying anti-hygromycin gene are: Hpt-F, 5'-GCTGTTATGCGGCCATTGTC-3' (SEQ ID NO: 9) and Hpt-R, 5'-GACGTCTGTCGAGAAGTTTC-3' (SEQ ID NO: 10). The PCR reaction system (25 μL system) is: 1 ul of sample DNA template to be tested, 2.5 μL of 10×PCR buffer, 2 μL of 10 mM dNTP, 0.25 μL of 20 uM primer, 0.5 μL of 2 U/μL Taq polymerase, and ddH$_2$O, total 25 μL. The PCR reaction procedure is: denaturation at 94° C. for 3 min; followed by 35 cycles of denaturation at 94° C. for 30 sec, annealing at 55° C. for 30 sec, extension at 72° C. for 40 sec; followed by extension at 72° C. for 5 min and then hold at 10° C. The amplified products were identified by 1% agarose gel electrophoresis, photographed and stored.

The primers used for amplifying Bt gene are: BtF, 5'-GGCCATACAACTGCTTGAGT-3' (SEQ ID NO: 11); BtR, 5'-GCGTTTCCCATAGTTCCATA-3' (SEQ ID NO:12), and the amplified fragment was 1 Kb in length. The PCR reaction procedure is: denaturation at 94° C. for 3 min; followed by 35 cycles of denaturation at 94° C. for 30 sec, annealing at 55° C. for 30 sec, extension at 72° C. for 1 min; followed by extension at 72° C. for 5 min and then hold at 10° C. The amplified products were identified by 1% agarose gel electrophoresis, photographed and stored. The PCR reaction system is shown in table 6.

The primers used for amplifying the key gene are: KeyF, 5'-AACGAGTGATGAGGTTCGCA-3' (SEQ ID NO:13); KeyR, 5'-ACCCGGCAAAACAGGTAGTT-3' (SEQ ID NO:14), and the amplified fragment was 672 bp in length. The PCR reaction procedure is: denaturation at 94° C. for 3 min; followed by 35 cycles of denaturation at 94° C. for 30 sec, annealing at 55° C. for 30 sec, extension at 72° C. for 1 min; followed by extension at 72° C. for 7 min and then hold at 4° C. The amplified products were identified by 1% agarose gel electrophoresis, photographed and stored. The PCR reaction system is shown in table 6.

TABLE 6

| Ingredients | PCR reaction system | | |
| --- | --- | --- | --- |
| | Working solution | Stock solution | μl/tube |
| PCR buffer (+Mg$^{2+}$) | 1 X | 10 X | 2.5 |
| dNTP | 0.2 mmol/L | 2.5 mmol/L | 2 |
| Forward primer (BtF or KeyF or HptF) | 0.2 μmol/L | 5 μmol/L | 1 |
| Reverse primer (BtR or KeyR or HptR) | 0.2 μmol/L | 5 μmol/L | 1 |
| Tag polymerase | 0.625U | 5U/μL | 0.125 |
| Template DNA | 50ng | 50ng/μL | 1 |
| ddH$_2$O | | | 17.375 |
| Total | | | 25 |

Thus, 21 pKey1- and 22 pLB-positive transformation lines were identified from 41 pKey1 and 50 pLB independent transformed lines of Nipponbare, respectively.

3. Detection of Transgenic Copy Number

The detection of transgenic copy number was performed using Southern hybridization techniques. First, the total rice DNA was digested with restriction endonuclease HindIII overnight at 37° C. (8-12 h). The digested DNA was separated by 0.8% (w/v) agarose gel electrophoresis (40V, 12 h). Thereafter, the electrophoretically separated DNA blot was transferred to a nylon membrane (GE Healthcare, UK). The preparation of the hybridization probes and Southern hybridization and hybridization signal detection were carried out according to the instructions provided by Roche DIG-High Prime DNA Labeling and Detection Starter Kit II (Switzerland), wherein the primers for preparing the hybridization probes are respectively:

```
pKey1:
                                            (SEQ ID NO: 15)
Key-1U20,      5'-ATGTCCAATTTACTGACCGT-3',
and (SEQ ID NO: 16)
Key-800L20,    5'-GCTTCAAAAATCCCTTCCAG-3';

pLB:
                                            (SEQ ID NO: 17)
Bt-577U24,     5'-AGGCTGATTGGAAACTACACCGAC-3',
and (SEQ ID NO: 18)
Bt-1161L24,    5'-ACAGCGGATGGCAAGTTAGAAGAG-3'.
```

Figure 9A:
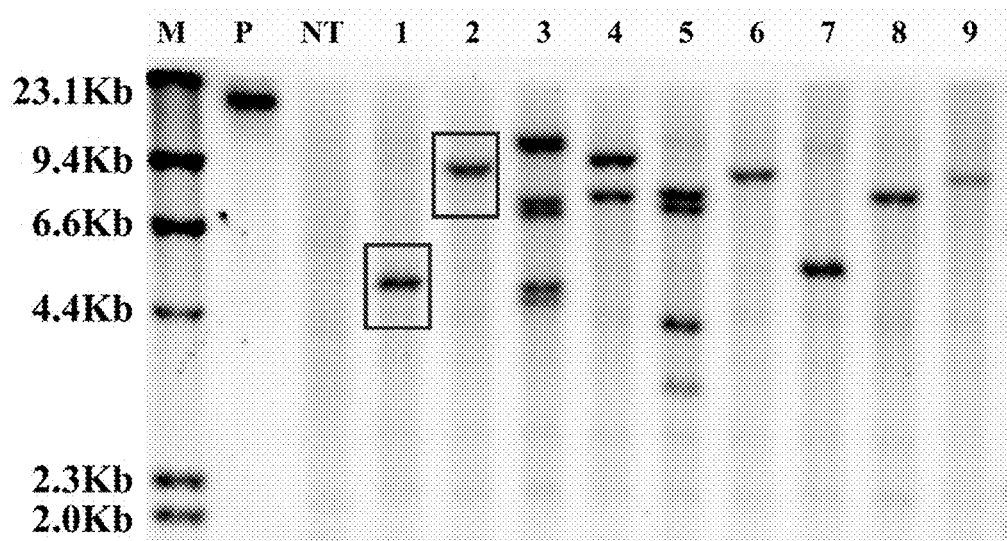
FIG. 9A is the copy number analysis of 9 samples of the Nipponbare line with pKey1 positive transformation, and the results show that 6 samples are single copied.
Figure 9B:
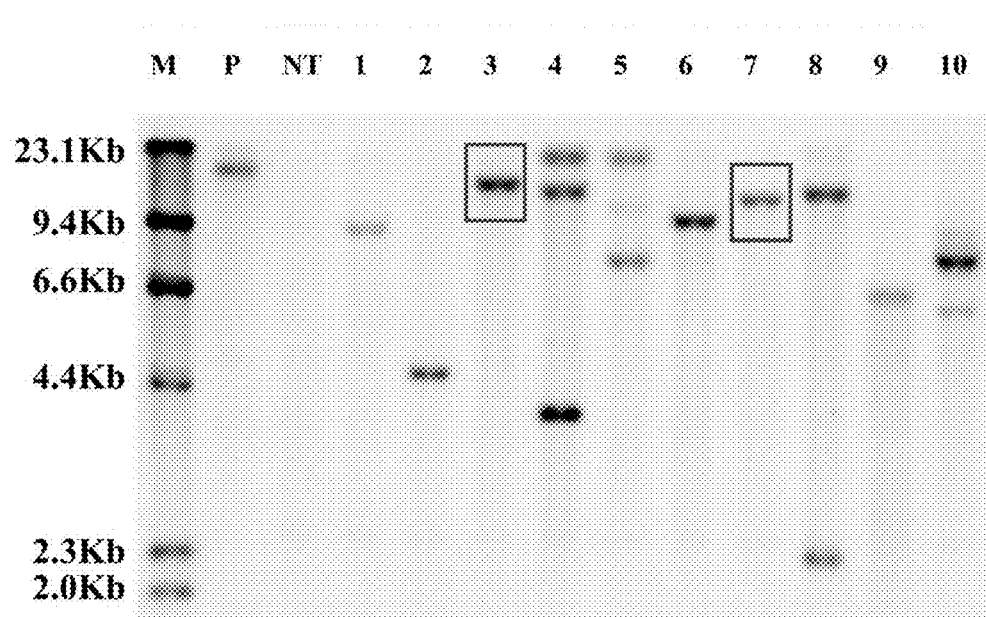
FIG. 9B is the copy number analysis of 10 samples of Nipponbare lines with pLB positive transformation, and the results show that 6 samples are single copied. According to the important agronomic traits such as seed setting rate, plant height and growth stage and other yield traits, two single-copied transformation lines (shown with the red box in the figure) were selected from pKey1 and pLB independent transformants (abbreviated as KEY and LB, respectively) and used as parents for the subsequent production of the LB/KEY and KEY/LB heterozygous hybrid. The selected material number is directly marked above the rectangular box. In the figure: M is DNA Molecular weight Marker II (DIG-labeled), P is a plasmid positive control, and N is a non-transgenic wild type Nipponbare negative control.

The copy number analysis results of the pKey1- and pLB-positive transformation lines of Nipponbare are shown in FIG. 9. As can be seen from FIG. 9, among 9 pKey1 positive Nipponbare transformation lines detected (FIG. 9A), 6 lines are single copied, and among 10 pLB positive transformation lines detected (FIG. 9B), 6 lines are single copied.

Figure 10:
FIG. 10: the homozygosity analysis and the PCR detection results of one of $T_2$ generation plants of the Nipponbare lines with pLB positive single copy transformation. In the Figure: M-DL2000 represents DL2000 DNA Marker; "+" represents a positive plasmid control, "−" represents a non-transgenic negative control; and 1-24 represents 24 independent individual plants in one of $T_2$ generation of Nipponbare lines with pLB positive single copy transformation.

4. PCR Amplification Detection and Screening of Single Copy Transgenic Homozygous Lines The PCR amplification detection and screening of single copy transgenic homozygous lines were performed in T$_2$ generation lines. T$_2$ generation seeds and plants were obtained after self-crossing the KEY1 and LB single copy transformation lines for two generations, respectively. Thereafter, the homozygous lines respectively carrying KEY1 and LB were screened out by PCR amplification detection. FIG. 10 shows the PCR detection results of one of T$_2$ generation homozygous lines of the Nipponbare pLB single copy transformation line. As shown in FIG. 10, 24 individual plants of the T$_2$ generation line show positive LB gene amplified fragments, indicating that the T$_2$ generation line is an LB transgenic homozygous line. The PCR amplification detections of other pLB and pKey1 transgenic homozygous lines were also performed in this way (data not shown).

Example 5: Determination of Bt Protein Content in the Stalk and Leaf and Identification of Insect Resistance of the Heterozygous Hybrid Prepared with the Applied Lock Element and Key Gene 1. Material Planting The Nipponbare pKey1 single-copy transgenic homozygous lines KEY1 and KEY2, which were screened by the PCR amplification detection described in Example 4 and were excellent in seed setting rate and other agronomic traits, were straight-crossed and back-crossed with the pLB single-copy transgenic homozygous lines LB3 and LB7, respectively. As a result, six hybrids were obtained totally.

In 2014, all tested materials (10 lines total), including wild-type Nipponbare negative control, 1 KEY (KEY1) and 2 LB (LB3 and LB7) transformation parental lines and six hybrids straight- and back-crossed by the above pKey1 single-copy transgenic homozygous line with pLB single-copy transgenic homozygous line were sown on June 25. 15 days later, 6 KEY/LB and LB/KEY straight- and back-crossed hybrid young seedlings were positively detected for positivity using the Bt Cry1Ab/1Ac transgenic rapid test strip (item number: AA0232, Youlong, Shanghai) according to the steps described in the product instruction. The hybrid young seedlings detected positive, together with the wild type negative control and the seedlings of the parent materials, were transplanted to the mud pool with the transgenic special isolation net, with at 1 row/section and 10 lines/row on July 28. The plant spacing was 20 cm and the row spacing was 40 cm. The experiment was repeated 3 times. Two rows of non-transgenic rice plants were planted around the entire test area as protection lines. No pesticides were applied during the whole growth period, and water and fertilizer managements were the same as the local field.

In 2015, the test materials were the same as those in 2014. All the tested materials were sown on May 25, and 15 days later, were detected by Bt Cry1Ab/1Ac transgenic rapid test strips (item number: AA0232, Youlong, Shanghai). The hybrid young seedlings confirmed as positive, together with the wild type control and the seedlings of the parent materials, were transplanted to the mud pool with the transgenic special isolation net, at 2 row/section and 12 lines/row on June 25. The plant spacing was 20 cm, and the row spacing was either 40 cm (wide spacing) or 15 cm (narrow spacing). The experiment was repeated 3 times. The rest of the cultivation managements were the same as those in 2014.

2. Determination of Bt Protein Content in Stalks and Leaves (1). ELISA Kit and Rice Samples The Bt protein contents in the stalks and leaves of Nipponbare KEY/LB and LB/KEY straight- and back-crossed hybrids were detected using an enzyme-linked immunosorbent assay (ELISA) kit from EnviroLogix™ Inc., Portland, USA. Rice stalk and leaf samples were sampled in three stages: tillering stage, heading stage and filling stage.

(2). Preparation of Working Solutions and Samples for Bt Protein Content Determination The determination working solution includes the extraction solution/dilution solution and the elution solution. The elution solution is prepared by adding the phosphate in the kit to 1 L double distilled water and then stirring to dissolve completely. The extraction solution/dilution solution is prepared by adding 200 μL of the elution solution into 1 mL of Tween-20, and stirring to dissolve completely. Both working solutions are stored at 4° C. and preheated to room temperature before use.

3 replicates were set for each heterozygous hybrid with 1 plant per replicate. The removed fresh samples were ground into powder with liquid nitrogen, about 20 mg powder was taken for each material, added the extraction/dilution solution in a ratio of 20 mg/500 μL and shaken fully to extract protein sample. The homogenate was placed into a 1.5 mL centrifuge tube and allowed to stand on ice for 30 min, then the supernatant was pipetted, centrifuged at 4000 rpm for 3 min at 4° C., and the supernatant was discarded. After dilution with the extraction/dilution solution at certain dilution factors, the Bt Protein concentration was determined and the dilution of the negative control was unnecessary. The dilution factors for the stalk and leaf samples at various stages are shown in Table 7.

TABLE 7

Dilution factor of the Bt protein sample

| Bt protein | Stages | leaf | stalk |
| --- | --- | --- | --- |
| Cry1Ab/1Ac | tillering stage | 200 | 50 |
|  | heading stage | 200 | 50 |
|  | filling stage | 200 | 50 |

3. ELISA Reaction and Protein Content Calculation

The ELISA reaction process was carried out according to the instructions of the kit. The specific steps were as follows:

(1) 50 μL of enzyme-conjugated Cry1Ab/1Ac antibody was added to each well of the plate (96 wells);

(2) Cry1Ab/1Ac standard samples at different concentration gradients (1, 0.5, 0.25, 0.1 ppb), 50 μL blank sample (extraction/dilution solution) and the sample to be tested were added into the well of the above 96-well plate with 1 sample/well. Two technical replicates were set for one sample, and then the 96-well plate was sealed with sealant and shaken at low speed (200 rpm) for 1-2 h;

(3) The supernatant was discarded, each well of a 96-well plate was added with 300 μL of the elution solution, shaken gently for 1 min. The elution solution was discarded and the plate was placed upside down on the absorbent paper to drain off the residual liquid;

(4) Step 3 was repeated for 4 times;

(5) Each well of a 96-well plate was added 100 μL of the substrate, and the wells corresponding to the samples containing Bt protein would appear blue, and each well was sealed and protected from light, and shaken at low speed (200 rpm) for about 30 min;

(6) Each well of a 96-well plate was added with 100 μL of the reaction stop solution, the blue color became yellow color, and the absorbance value was immediately read.

The absorbance value was determined using a microplate reader (Synergy H1, USA) reading at a wavelength of 450 nm. A standard curve is plotted with the concentration and absorbance of the standard samples. The concentration of the test sample was read from the standard curve, and the protein content in the rice tissue was calculated based on the dilution factor. The protein content was calculated by the following formula: Bt protein content (μg/g fresh weight) =test sample concentration (ng/mL)×dilution factor×sample loading volume (μL)/tissue fresh weight (mg). Differences in protein concentration among the different hybrid combinations, different stages, and tissues were compared using multiple t-tests of the grouping data.

Figure 11:
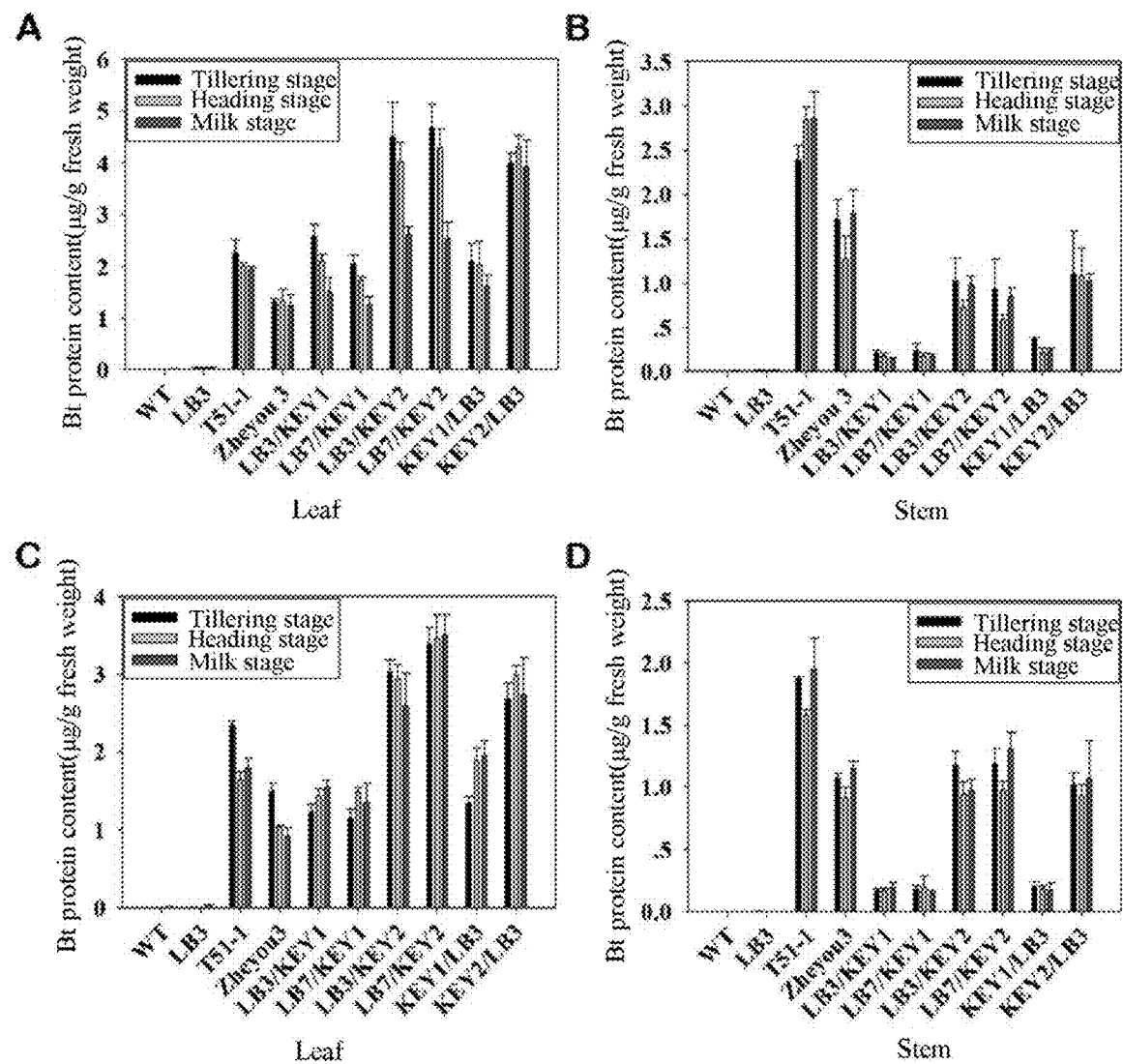
FIG. 11: ELISA quantitative analysis results of Bt protein contents in stalk and leaf tissues at the tillering, heading and filling stages of six straight- and back-crossed hybrids of 2 Nipponbare pKey1 single copy transformation lines and 2 Nipponbare pLB single copy transformation lines, wherein: KEY1, KEY2 and LB3, LB7 are single copy homozygous parents screened from pKey1 and pLB transformants; LB3/KEY1, LB7/KEY1, LB3/KEY2, LB7/KEY2, KEY1/LB3, and KEY2/LB3 are the heterozygous hybrids crossed by the above single copy homozygous parents. T51-1 and Zheyou 3 are positive controls.

The results of the two-year analysis are shown in FIG. 11. In the three growth stages, the Bt protein contents in the leaves of the six straight- and back-crossed hybrids are consistent with or higher than those in the positive control T51-1 and its two-hybrid rice Zheyou 3 (FIGS. 11A and 11C). The Bt protein contents in the stalks of 3 heterozygous hybrids LB3/KEY2, LB7/KEY2 and KEY2/LB3 are consistent with that in Zheyou 3 positive control. The Bt protein contents in the stalks of the other 3 heterozygous hybrids LB3/KEY1, LB7/KEY1 and KEY1/LB3 are all lower than those in the above two positive controls (FIGS. 11B and 11D).

4. Evaluation of the Insect Resistance in the Field

The evaluation of the resistance of KEY/LB and LB/KEY straight- and back-crossed hybrids to *Chilo suppressalis* in the field was carried out using the natural insect inoculation method and the artificial insect inoculation method. The natural insect inoculation method was carried out 5-7 days after the peak of *Chilo suppressalis* outbreak. The indicators include the number of dead hearts and the number of white spikes. The artificial insect inoculations were carried out for two times at the highest tillering stage and one week before the heading. The eggs were purchased from Jiangxi Shennong Technology Co. Ltd., and the purchased eggs were placed in a glass test tube with a length of 12 cm and a diameter of 2.0 cm with a wet cotton ball at the bottom (one egg mass/tube), the tube was sealed with a cotton plug and tied up with a black cloth on the outside of the tube mount. Egg hatching was carried out at a temperature of 26-28° C. and a humidity of 80% under 16 hours light/8 hours dark condition. The hatched first instar larvae were inoculated together with the test tube to the base of the rice bundle within 6 hours after hatching. The specific procedure is as follows: the black cloth was opened and the cotton plug was removed, the base of the test tube was inserted into the soil of the rice field by making the tube mouth close to the rice straw, so that the larva can climb from the test tube to the rice straw for infestation. The inoculated amount of insects was one egg mass (about 80 first instar larvae)/plant. Two weeks later, the number of dead hearts or the number of white spikes caused by *Chilo suppressalis* was determined, and meanwhile, the total number of tillers or the total number of effective spikes of the test plants were determined.

The insect resistance of LB/KEY and KEY/LB straight- and back-crossed hybrids to *Cnaphalocrocis medinalis* in the field was evaluated by the natural insect inoculation method. The number of the damaged leaves and the degree of the damage to leaves per plant caused by *Cnaphalocrocis medinalis* were determined 5-7 days after the occurrence of the infestation peak.

The statistical analysis of the resistance evaluation indexes of LB/KEY and KEY/LB straight- and back-crossed hybrids to *Chilo suppressalis* and *Cnaphalocrocis medinalis* was carried out with SPSS22.0 (SPSS, Chicago, USA) software. The significance of the difference of the *Chilo suppressalis* harm rate between the hybrids and the wild type Nipponbare and the parental control with the lock element and the Bt gene was done by Dunnett's t test.

The results of the natural insect inoculation identification in the field in 2014 demonstrate that six straight- and back-crossed hybrids are highly resistant to *Cnaphalocrocis medinalis*. *The number of the damaged tillers per plant and the number of the damaged leaves per plant of the wild type Nipponbare and the parental lines carrying the lock element and Bt gene reach 54.81-65.27% and 9.17-14.60%, respec-* tively, while the two indicators of the six straight- and back-crossed hybrids are only 0.00-1.33% and 0.00-0.13% (Table 8). The difference therebetween reaches an extremely significant level of P=0.01. In addition, the four heterozygous hybrids LB3/KEY2, LB7/KEY2, KEY1/LB3 and KEY2/LB3 were also well resistant to the naturally inoculated *Chilo suppressalis*. Compared with the *Chilo suppressalis* damage rate of 6.96-8.02% in the wild type Nipponbare and the parental lines with lock element and Bt gene (Table 8), the *Chilo suppressalis* damage rates in these heterozygous hybrids are only within 0.00-0.63%. The difference therebetween also reaches an extremely significant level of P=0.01.

The results of the natural insect inoculation identification in the field in 2015 are essentially the same as those in 2014. Six straight- and back-crossed hybrids all exhibit the good field resistance to *Cnaphalocrocis medinalis* and *Chilo suppressalis*. The difference between the hybrids and the wild type Nipponbare and the parental lines with lock element and Bt gene also reach an extremely significant level of P=0.01 (Table 8).

As for the artificially insect inoculation identifications, in 2014, two hybrids with low Bt protein content in the stem and leaf tissues, LB3/KEY1 and LB7/KEY1, were selected as the materials to be tested, and the wild type Nipponbare and two parents with the lock element and Bt gene, LB3 and LB7, were used as the insect-sensitive controls. The results show that the *Chilo suppressalis* damage rates in the four control lines were more than 23%, while those in the two heterozygous hybrids were less than 8% (Table 9), thus showing the good resistance to *Chilo suppressalis*.

Figure 12:
FIG. 12: the resistance of the lock element and key gene heterozygous hybrid LB3/KEY2 (left panel) and wild-type Nipponbare control (right panel) to the artificially inoculated first instar larvae of *Chilo suppressalis* (1 egg mass, about 80 worms per egg mass) under field condition. In the figure, it can be seen that a high ratio of white spikes appear on the wild type control, and almost no white spikes appear on the transgenic heterozygous hybrids.
Figure 13A:
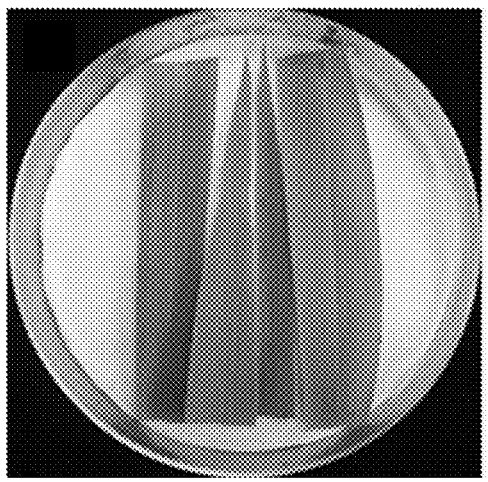
FIG. 13: the resistance of the isolated leaves of the lock element and key gene LB3/KEY2 heterozygous hybrids to the indoor artificially inoculated first instar larvae of *Chilo* suppressalis. In the figure, A: positive control TT51-1; B: wild type Minghui 63 control; C: LB3/KEY2 heterozygous hybrid; D: wild type Nipponbare negative control; E: Nipponbare KEY2 parent transformation line; and F: Nipponbare LB3 parent transformation line. The picture shows that the resistance of transgenic heterozygous hybrid LB3/KEY2 to Chilo suppressalis is consistent with that of the positive control T51-1.
Figure 13B:
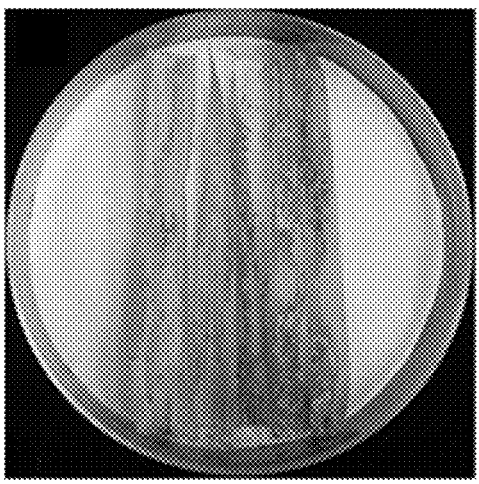
Figure 13C:
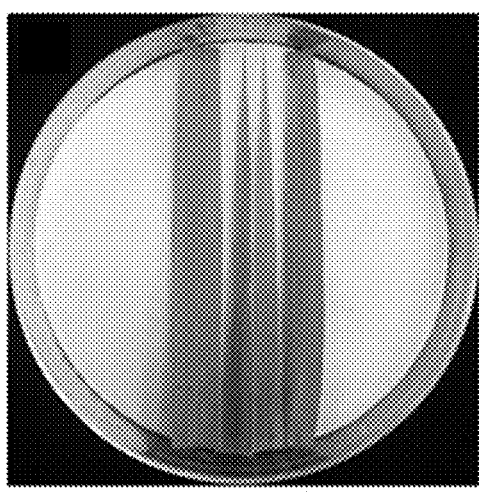
Figure 13D:
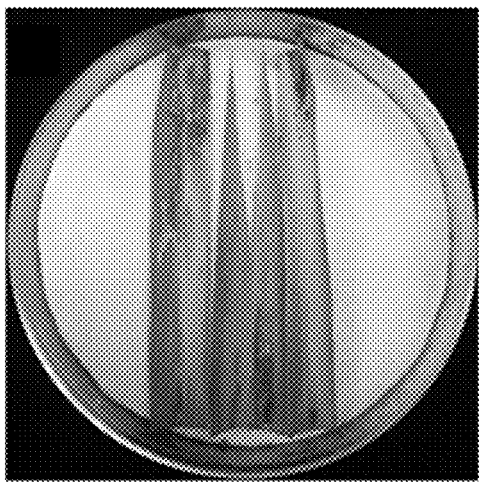
Figure 13E:
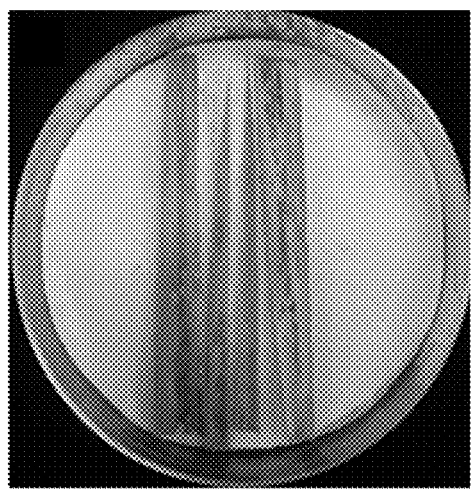
Figure 13F:
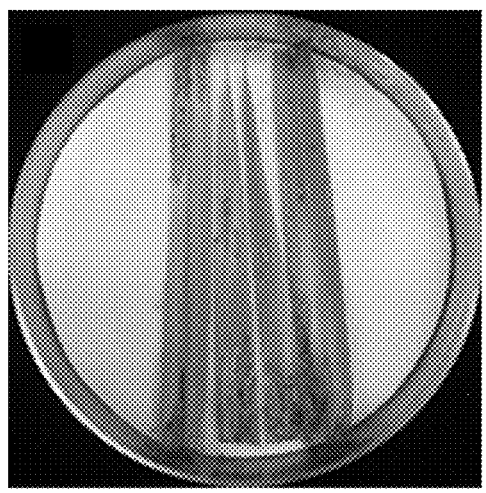

In 2015, the artificial insect inoculation in the field was repeated with one heterozygous hybrid LB3/KEY2 with relatively high Bt protein content in the stalk. The results show that the damage of *Chilo suppressalis* to the heterozygous hybrid is extremely low and the average damage rate of the tillers or spikes of the rice is only 0.78%, which is significantly lower than 56.26% of the wild-type Nipponbare negative control (Table 9 and FIG. 12).

TABLE 9 the resistance of LB3/KEY2 hybrid combinations to *Chilo suppressalis* artificially inoculated at the tillering stage and 7 days before heading under the field conditions

| Identification year | Plant | replicate | The number of the individual tested | The mean tillering number | *Chilo suppressalis* damage rate (%) |
|---|---|---|---|---|---|
| 2014 | Nip-WT | 1 | 10 | 13.5 | 36.30 ± 25.75 |
|  |  | 2 | 10 | 14.5 | 28.97 ± 13.72 |
|  |  | 3 | 10 | 14.3 | 25.17 ± 10.27 |
|  |  | mean | 10 | 14.1 | 30.15 ± 5.65 |
|  | KEY1 | 1 | 10 | 12.3 | 34.96 ± 31.66 |
|  |  | 2 | 10 | 11.4 | 21.93 ± 18.03 |
|  |  | 3 | 10 | 11.7 | 32.48 ± 15.03 |
|  |  | mean | 10 | 11.8 | 29.79 ± 6.92 |
|  | LB3 | 1 | 10 | 11.6 | 30.17 ± 12.76 |
|  |  | 2 | 10 | 12.9 | 30.23 ± 23.94 |
|  |  | 3 | 10 | 12.5 | 28.00 ± 10.99 |
|  |  | mean | 10 | 12.3 | 29.47 ± 1.27 |
|  | LB7 | 1 | 10 | 14.3 | 24.48 ± 7.79 |
|  |  | 2 | 10 | 15.0 | 23.33 ± 7.10 |
|  |  | 3 | 10 | 14.2 | 23.94 ± 8.79 |
|  |  | mean | 10 | 14.5 | 23.92 ± 0.57* |
|  | LB3/ KEY1 | 1 | 10 | 10.7 | 11.21 ± 10.79 |
|  |  | 2 | 10 | 10.3 | 4.85 ± 6.10 |
|  |  | 3 | 10 | 10.3 | 4.85 ± 7.25 |
|  |  | mean | 10 | 10.4 | 6.97 ± 3.67** |
|  | LB7/ KEY1 | 1 | 10 | 10.90 | 10.09 ± 15.53 |
|  |  | 2 | 10 | 10.30 | 5.83 ± 9.31 |
|  |  | 3 | 10 | 10.00 | 7.00 ± 9.98 |
|  |  | mean | 10 | 10.40 | 7.64 ± 2.20** |
| 2015 | Nip-WT | 1 | 24 | 12.5 | 59.47 ± 20.64 |
|  |  | 2 | 24 | 11.9 | 48.77 ± 23.34 |
|  |  | 3 | 24 | 13.6 | 60.55 ± 19.14 |
|  |  | mean | 24 | 12.7 | 56.26 ± 6.51 |
|  | LB3/ KEY2 | 1 | 24 | 12.8 | 0.32 ± 1.46 |
|  |  | 2 | 24 | 13.3 | 0.63 ± 2.55 |
|  |  | 3 | 24 | 11.9 | 1.40 ± 3.70 |
|  |  | mean | 24 | 12.7 | 0.78 ± 0.56** |

*represents that the difference from the control reaches P < 0.05 significant level, and
**represents that the difference from the control reaches P < 0.01 extremely significant level.

TABLE 8 the resistance of six LB/KEY and KEY/LB hybrid combinations, three KEY and LB parents, and wild-type Nipponbare control to *Chilo suppressalis* and *Cnaphalocrocis medinalis* under the field conditions[a]

|  | 2014 | | | 2015 | | |
|---|---|---|---|---|---|---|
|  | *Chilo suppressalis* | *Cnaphalocrocis medinalis* damage rate (%) | | *Chilo suppressalis* | *Cnaphalocrocis medinalis* damage rate (%) | |
| Lines | damage rate (%) | damaged tiller per plant | damage leaves per plant | damage rate (%) | damaged tiller per plant | damage leaves per plant |
| WT[b] | 7.59 ± 0.69[c] | 63.82 ± 10.70 | 12.47 ± 1.20 | 7.22 ± 1.00 | 59.76 ± 6.14 | 12.17 ± 0.57 |
| KEY2 | 6.96 ± 0.79 | 54.81 ± 0.93* | 9.17 ± 0.91** | 7.46 ± 1.39 | 56.71 ± 7.69 | 10.70 ± 0.61** |
| LB3 | 8.02 ± 0.77 | 65.27 ± 8.19 | 12.47 ± 1.20 | 6.73 ± 0.56 | 62.33 ± 2.09 | 11.67 ± 0.42 |
| LB7 | 7.39 ± 0.47 | 58.36 ± 3.59 | 14.60 ± 0.62** | 7.02 ± 0.41 | 61.49 ± 1.29 | 13.37 ± 0.67** |
| LB3/KEY1 | ND | 0.65 ± 1.12** | 0.13 ± 0.23** | 0.28 ± 0.48** | 0.00 ± 0.00** | 0.00 ± 0.00** |
| LB7/KEY1 | ND | 1.33 ± 2.31** | 0.13 ± 0.23** | 0.00 ± 0.00** | 0.25 ± 0.44** | 0.03 ± 0.06** |
| LB3/KEY2 | 0.00 ± 0.00** | 0.31 ± 0.53** | 0.03 ± 0.06** | 0.00 ± 0.00** | 0.26 ± 0.45** | 0.00 ± 0.00** |
| LB7/KEY2 | 0.00 ± 0.00** | 0.00 ± 0.00** | 0.00 ± 0.00** | 0.00 ± 0.00** | 0.00 ± 0.00** | 0.00 ± 0.00** |
| KEY1/LB3 | 0.63 ± 0.55** | 0.63 ± 0.55** | 0.07 ± 0.06** | 0.00 ± 0.00** | 0.26 ± 0.45** | 0.07 ± 0.12** |
| KEY2/LB3 | 0.00 ± 0.00** | 0.00 ± 0.00** | 0.00 ± 0.00** | 0.00 ± 0.00** | 0.00 ± 0.00** | 0.00 ± 0.00** |

[a]The data of each line are based on three replicates and 10 individual plants are randomly surveyed per replicate for each line.
[b]WT is wild-type Nipponbare control, and the identification data of all other 9 lines to be tested are compared with the wild type control. The data are analyzed by Dunnett t test of SPSS 22.0 software package.
[c]Values represent average ± mean standard deviation.
ND. represents no data.
**represents a very significant difference P < 0.01.

3. Indoor Insect Resistance Evaluation

The indoor insect resistance evaluation was carried out on *Chilo suppressalis*. The eggs were also purchased from Jiangxi Shennong Technology Co. Ltd., and the egg hatching method was the same as described the above. The method used for the insect resistance evaluation includes the isolated stalk insect inoculation method and the isolated leaf insect inoculation method.

The isolated stalk insect inoculation method is as follows: the rice stalk after the jointing is removed and cut into 12 cm long stalk segments with the joints and leaf sheaths. Two stalk segments of the same plant and 20 first instar larvae of *Chilo suppressalis* are placed in each insect tube. The insect tube is sealed with a cotton plug, placed at 25-27° C. and 80% relative humidity, and the larval mortality is counted after 6 days.

The isolated leaf insect inoculation method is as follows: the blade leaves and the penultimate leaves at the booting stage are removed and cut into 8 cm long leaf segments, and placed in a culture dish with filter paper moistened with 2 mL of distilled water. 4 leaf segments and 15 first instar larvae of *Chilo suppressalis* are placed in each culture dish. The culture dishes are wrapped with PARAFILM four times to prevent larvae from escaping out. Thereafter, they are housed at room temperature (25° C.), and the mortality of the larvae is counted after 6 days.

Each insect tube or culture dish is counted as 1 replicate, with 3 replicates per sample. The resistance of different LB/Key1 and Key1/LB transformed heterologous hybrids to *Chilo suppressalis* was compared using t test of the grouped stalk and leaf data. The results demonstrate that under the indoor artificial inoculation conditions, the insect resistance performances of the isolated leaves and stalks of LB3/KEY2 heterologous hybrids to *Chilo suppressalis* are also excellent (FIGS. 13 and 14). The mortality of the *Chilo suppressalis* larvae fed with the isolated leaves is 100%, and the mortality of the *Chilo suppressalis* larvae fed with the isolated stalks is also more than 95%, while the mortality of the *Chilo suppressalis* larvae fed with the isolated control leaves and stalks is no more than 20% (Table 10).

2. Preparation of Working Solutions and Samples for Cry1Ab/1Ac Protein Content Determination The determination working solution includes the extraction solution/dilution solution and the elution solution. The elution solution is prepared by adding the phosphate in the kit to 1 L double distilled water and then stirring to dissolve completely. The extraction solution/dilution solution is prepared by adding 200 μL of the elution solution into 1 mL of Tween-20, and stirring to dissolve completely. Both working solutions are stored at 4° C. and preheated to room temperature before use.

Each hybrid combination consisted of 3 replicates with 1 plant/replicate and 50 seeds/plant. The harvested seeds were hulled and prepared into unrefined rice for use. Then, some unrefined rice were polished into refined rice using a polishing machine, and 50 unrefined rice and 50 refined rice were selected and ground into flours, and about 20 mg of flours were taken from each material, and the extraction/dilution solutions were added in a ratio of 20 mg/500 μL to extract the protein samples under intense shaking. The resulting homogenate was placed in a 1.5 mL centrifuge tube, allowed to stand on ice for 30 min, and centrifuged at 4000 rpm for 3 min at 4° C., and the supernatant was pipetted for use. Thereafter, the protein samples extracted from the refined rice and unrefined rice of the positive control T51-1 and its two-line hybrid rice Zheyou 3 were diluted 50 times with the extracting/diluting solution, and then the Bt protein concentrations were measured. The dilutions of the samples of the heterozygous hybrid and negative control were unnecessary.

3. ELISA Reaction and Protein Content Calculation

The ELISA reaction process was carried out according to the instructions of the kit, and the specific steps were the same as described for the Bt protein content determination in the aforementioned stalk and leaf tissues.

4. Determination of Cry1Ab/1Ac Protein Contents in the Refined Rice Endosperms and the Unrefined Rice Flours of 6 Heterozygous Hybrids The results of repeated measurements in 2014 and 2015 showed that the Cry1Ab/1Ac protein contents of the refined

TABLE 10

Resistance of the leaves and stalks of the LB3/KEY2 heterozygous hybrids to artificially inoculated *Chilo suppressalis*

| | The mortality of the *Chilo suppressalis* larvae (%) | | | | | | | |
|---|---|---|---|---|---|---|---|---|
| | Leaves | | | | Stalks | | | |
| Lines | Replicate I | Replicate II | Replicate III | Mean | Replicate I | Replicate II | Replicate III | Mean |
| LB3/KEY2 | 100.0 | 100.0 | 100.0 | 100.0 ± 0.0 | 100.0 | 95.0 | 95.0 | 96.7 ± 2.9 |
| Nip-WT | 6.7 | 13.3 | 6.6 | 8.8 ± 3.8 | 20.0 | 10.0 | 0.0 | 10.0 ± 10.0 |

Example 6: Determination of Cry1Ab/1Ac Protein Content in the Endosperm of the Heterologous Hybrids with Applied Lock Element/Key Gene In order to verify whether the gene combination has the function of preventing the target gene in an endosperm-specific manner, the Cry1Ab/1Ac protein contents in the endosperms of the six lock element/key gene heterozygous hybrids described in Example 5 were further determined.

1. ELISA Kit and Rice Samples

The Cry1Ab/1Ac protein content in the endosperm of Nipponbare pKey1/pLB heterologous hybrid was also determined using the enzyme-linked immunosorbent assay (ELISA) kit from EnronoLogix™ Inc. (Portland. USA). The rice is detected at the filling period.

rice endosperm of 6 heterozygous hybrids were not significant different compared with the detection values of the wild type Nipponbare negative control and the LB3 parental line carrying the lock element and Bt gene. Their measured values were all less than 1 ng/g flour, which was extremely significantly lower than the average measured value of the positive control T51-1 (338.45 ng/g flour) and its two-line hybrid rice Zheyou 3 (184.75 ng/g flour) in the two years (Table 11). This result therefore confirms that the "gene combination" as designed in the present invention does completely switch off the expression of the exogenous target gene in the rice endosperm.

The Cry1Ab/1Ac protein content determined in unrefined rice of some heterozygous hybrid reached 1-3 ng/g flour, significantly higher than the detection value of the unrefined rice of the wild type Nipponbare negative control (less than 1 ng/g flour) (Table 11). This might be related with the fact that the pericarp in the unrefined rice (composed of several parts such as peel, seed coat, perisperm and aleurone layer) contains the chloroplast at the beginning of the development. However, during the milling, the pericarp of the unrefined rice was milled as a bran layer, and therefore, a very small amount of Cry1Ab/1Ac protein accumulated therein was also removed.

TABLE 11

ELISA quantitative analysis of the Cry1Ab/1Ac protein contents in the unrefined rice and refined rice of the parental KEY and LB lines, hybrid LB/KEY and KEY/LB lines, positive control T51-1 and Zheyou 3 and wild-type negative control Nipponbare

| | Cry1Ab/1Ac protein content (ng/g)[a] | | | |
|---|---|---|---|---|
| | 2014 | | 2015 | |
| Lines | Refined rice | Unrefined rice | Refined rice | Unrefined rice |
| WT[b] | 0.42 ± 0.08[c] | 0.71 ± 0.11 | 0.21 ± 0.07 | 0.24 ± 0.11 |
| LB3 | 0.67 ± 0.37 | 1.36 ± 0.59* | 0.22 ± 0.08 | 1.81 ± 0.48** |
| LB3/KEY1 | 0.44 ± 0.06 | 1.07 ± 0.13 | 0.23 ± 0.08 | 0.33 ± 0.03 |
| LB7/KEY1 | 0.44 ± 0.04 | 0.86 ± 0.09 | 0.17 ± 0.05 | 0.61 ± 0.25 |
| LB3/KEY2 | 0.80 ± 0.20 | 2.09 ± 0.15** | 0.25 ± 0.02 | 1.19 ± 0.49* |
| LB7/KEY2 | 0.64 ± 0.10 | 2.52 ± 0.06** | 0.28 ± 0.12 | 1.06 ± 0.27 |
| KEY1/LB3 | 0.29 ± 0.05 | 1.04 ± 0.01 | 0.14 ± 0.08 | 0.20 ± 0.05 |
| KEY2/LB3 | 0.60 ± 0.13 | 1.98 ± 0.17** | 0.25 ± 0.08 | 1.50 ± 0.58** |
| T51-1 | 371.67 ± 30.85** | 879.36 ± 67.71** | 305.23 ± 27.44** | 1040.33 ± 60.38** |
| Zheyou 3 | 157.32 ± 27.2** | 400.53 ± 34.79** | 212.17 ± 47.27** | 578.69 ± 1.10** |

[a]represents that the data in the table are measured from 50 grains/test material/grain sampled randomly (repeated three times in total);
[b]WT is the wild-type Nipponbare positive control, and the measurement data of all other lines are compared. The data are analyzed by Dunnett t test of SPSS 22.0 software package.
[c]Values represent average ± mean standard deviation.
*represents that the difference from the wild-type Nipponbare negative control reaches $P < 0.05$ significant level.
**represents that the difference from the wild-type Nipponbare negative control reaches $P < 0.01$ extremely significant level.

Sequence Listing and Annotations

The present invention provides the nucleotide sequence and the putative amino acid sequence thereof of the exogenous target gene Bt, gene lock Lock1/Lock2 and gene key Key1/Key2 for constructing a "gene combination", wherein the Bt gene cry1Ab/1Ac is artificially synthesized and kindly provided by the Academician Yunliu FAN of the Academy of Agricultural Sciences; the lock element Lock1/Lock2 and the key gene Key1/Key2 were artificially synthesized. The respective sequences listed in the sequence listing are as follows.

| SEQ ID NO: | Annotations |
|---|---|
| 1 | Bt gene coding sequence; 1833 bp in total, wherein the composition ratio of bases A, T, G and C is 476: 479: 401: 477 |
| 2 | putative Bt protein sequence; 610 amino acid residues in total, wherein the first 489 amino acid residues are from cry1Ab, and the last 121 amino acid residues are from cry1Ac |
| 3 | DNA sequence of key gene Key1; 1116 bp in total, wherein the composition ratio of bases A, C, G and T is 287: 248: 319: 262 |
| 4 | putative KEY1 protein sequence; 371 amino acid residues in total |
| 5 | lock element (Lock1); 333 bp in total, the sequence does not encode protein, and is only the regulatory sequence |
| 6 | DNA sequence of key gene Key2: 1428 bp in total, wherein the composition ratio of bases A, C, G and T is 495: 255: 293: 385 |
| 7 | putative KEY2 protein sequence; 475 amino acid residues in total |
| 8 | selectable lock element (Lock2), 333 bp in total |
| 9 | hygromycin-resistant gene primer Hpt-F |
| 10 | hygromycin-resistant gene primer Hpt-R |
| 11 | Bt gene PCR amplification primer BtF |
| 12 | Bt gene PCR amplification primer BtR |
| 13 | Key gene PCR amplification primer KeyF |
| 14 | Key gene PCR amplification primer KeyR |
| 15 | pKey1 SOUTHERN hybridization probe preparation primer Key1-1U20 |
| 16 | pKey1 SOUTHERN hybridization probe preparation primer Key1-800L20 |

| SEQ ID NO: | Annotations |
|---|---|
| 17 | pLB1 SOUTHERN hybridization probe preparation primer Bt-577U24 |
| 18 | pLB1 SOUTHERN hybridization probe preparation primer Bt-1161L24 |
| 19-43 | Primers used for the expression vector (see Table 1) |

REFERENCES

1. Bock R., 2001, Transgenic plastids in basic research and plant biotechnology. J. Mol. BioL., 312:425-438.
2. Cai M., Wei J., Li X. H., Xu C. G., Wang S. P. 2007, A rice promoter containing both novel positive and negative cis-elements for regulation of green tissue-specific gene expression in transgenic plants. Plant Biotechnol J, 5:664-674.
3. Chu C., Wang C., Sun C., Hsu C., Yin K., Chu C., Bi F., 1975, Establishment of an efficient medium for anther culture of rice through comparative experiments on the nitrogen sources. Sci Sin., 18:659-668.
4. Daniell H., 2002, Molecular strategies for gene containment in transgenic crops, Nat. Biotechnol., 20(6):581-586.
5. Hiei Y., Ohta S., Komati T., 1994, Efficient transformation of rice (*Oryza saliva* L.) mediated by *Agrobacterium* and sequence analysis of the boundaries of T-DNA. Plant J., 6:271-282.
6. James, Clive, 2014. Global Status of Commercialized Biotech/GM Crops: 2014. ISAAA Brief No. 49. ISAAA: Ithaca, N.Y.
7. Jang I. C., Nahm B. H., Kim J. K., 1999, Subcellular targeting of green fluorescent protein to plastids in transgenic rice plants provides a high-level expression system. Mol Breeding, 5:453-461.
8. Kyozuka J., McElroy D., Hayakawa T., Xie Y. Wlu R., Shimamoto K., 1993, Light-regulated and cell-specific expression of tomato rbcS-gusA and rice rbcS-gusA fusion genes in transgenic rice. Plant Physiol, 102:991-1000.
9. Liu Q. Q., Zhang J. L., Wang Z. Y., Hong M. M., Gu M. H., 1998, A highly efficient transformation system mediated by *Agrobacterium tumefaciens* in rice. Acta Phytophysiol. Sin., 24:259-271.
10. Luo K., Duan H., Zhao D., Zheng X., Deng W., Chen Y., Neal Stewart Jr. C., McAvoy R., Jiang X., Wu Y., He A., Pei Y., Li Y., 2007, "GM-gene-deletor": fused loxP-FRT recognition sequences dramatically improve the efficiency of FLP or CRE recombinase on transgene excision from pollen and seeds of tobacco plants. Plant Biotech J., 5(2):263-274.
11. Nomura M., Katayama K., Nishimura A., IshidaY., Ohm S., Komari T., Miyao T. M., Tajima S., Matsuoka M., 2000, The promoter of rbcS in a C3 plant (rice) directs organ-specific, light-dependent expression in a C4 plant (maize), but does not confer bundle sheath cell-specific expression. Plant Mol Biol, 44:99-106.
12. Oliver M., Quisenberry J. E., Trolinder N. L. G., 1998, Control of plant gene expression. United States Patent, US005723765A
13. Paoletti M. G., Pimentel D., 1996, Genetic engineering in agriculture and the environment. Bioscience, 46(9): 665-673.
14. Thilmony R., Guttman M., Thomson J. G., Bleeh A. E., 2009, THE LP2 leueine-rich repeat receptor kinase gene promoter directs organ-specific, light-responsive expression in transgenic rice. Plant Biotechnol J., 7:867-882.
15. Toriyama K., Hinata, K., 1985, Cell suspension and protoplast culture in rice. Plant Sci., 41:179-183.
16. Tu J., Zhang G., Datta K., Xu C, He Y., Zhang Q., Khush G. S., Datta S. K., 2000, Field performance of transgenic elite commercial hybrid rice expressing *Bacillus thuringiensis* S-endotoxin. Nature Biotech, 18:1101-1104.
17. Yanagisawa S., Izui K., 1989, Maize Phosphoenol pyruvate Carboxylase Involved in C4 Photosynthesis: Nucleotide Sequence Analysis of the 5' Flanking Region of the Gene. J. Biochem., 106:982-987.
18. Yang R., Tang Q., Wang H., Zhang X., Pan G., Wang H., Tu J., 2011, Analyses of two rice (*Oryza sativa* L.) cyclin-dependent kinase inhibitors and effects of transgenic expression of OsiICK6 on plant growth and development. Annals of Botany. 107:1087-1101.
19. Ye R. J., Zhou F., Lin Y. J., 2012. Two novel positive eis-regulatory elements involved in green tissue-specific promoter activity in rice (*Oryza sativa* L ssp.). Plant Cell Rep, 31:1159-1172.
20. Yoshida S., Forno D. A., Cock J. H., Gomez K. A., 1976, Routine procedures for growing rice plants in culture solution. In Laboratory Manual for Physiological Studies of Rice pp. 61-66. Philippines, IRRI, Manila.
21. Zhao D., Lv L., He A., Luo K., Duan H., Zheng X., Deng W., Chen Y., An X., He M., 2008. The gene-deletor technology: principle and potential application in genetically engineered agriculture, Molecular Plant Breeding, 2008, 6(3): 413-418.

The invention is not limited to the scope of the specific embodiments described herein. In fact, various modifications of the invention in addition to those described herein will be apparent to those skilled in the art reading the above description. These modifications should fall within the scope of the appended claims.

It should also be understood that all base sizes or amino acid sizes given for nucleic acids or polypeptides, and all molecular weight or molecular mass values are approximate and are provided for illustration.

The invention claimed is:

1. A method for controlling the expression of an exogenous target gene in a plant, the method comprising introducing a first expression vector and a second expression vector into a recipient plant,
wherein the first expression vector comprises a lock polynucleotide and the exogenous target gene operably linked thereto, wherein the lock polynucleotide comprises SEQ ID NO: 5 and blocks the expression of the exogenous target gene, and
wherein the second expression vector comprises a key polynucleotide and a tissue-specific promoter operably linked thereto, wherein the key polynucleotide comprises SEQ ID NO: 3 and switches on the expression of the exogenous target gene blocked by the lock polynucleotide.

2. The method of claim 1, wherein the first expression vector further comprises a constitutive promoter operably linked to the lock polynucleotide, wherein the lock polynucleotide is located between the constitutive promoter and the exogenous target gene, and
wherein the constitutive promoter is selected from the group consisting of the cauliflower mosaic virus 35S promoter, the nopaline synthase gene promoter from the T-DNA region of the *Agrobacterium tumefaciens* Ti plasmid, the rice actin promoter Actin I, and the maize ubiquitin (Ubi) gene promoter.

3. The method of claim 1, wherein the tissue-specific promoter is selected from the group consisting of the rice green tissue-specific promoter ribulose-1,5-bisphosphate carboxylase small subunit (rbcS) promoter, the maize phosphoenolpyruvate carboxylase (PEPC) promoter, the rice green tissue-specific expression DX1 promoter, the rice photosystem II 10 kDa polypeptide D540 promoter, the rice leucine-rich repeat-like receptor protein kinase (LP2) promoter, and the maize chloroplast C4 Pdk promoter; preferably, the tissue-specific promoter is the rbcS promoter.

4. The method of claim 1, wherein the exogenous target gene is an insect resistance gene or a herbicide resistance gene,
wherein the insect resistance gene is selected from the group consisting of the cry1Ab, cry1Ac, cry1Ab/1Ac, cry1C, co/2A, and Vip3 like insect resistance genes from *Bacillus thuringiensis*; the anf and sep genes from *Serratia entomophila*; the cmb gene of *Clostridium bifermentans*; the mtx gene from *Bacillus sphaericus*; the insecticidal protein gene from *Xenorhabdus nematophilus*; the tca and tcb genes from *Photorhabdus luminescens*; and the prl gene from *Metarhizium anisopliae*, and
wherein the herbicide resistance gene is selected from the group consisting of the EPSP synthase gene for glyphosate resistance, the *Salmonella typhimurium* EPSP mutant gene aroA, the bar gene for glufosinate resistance, the ALS mutant gene Ilv G for imidazolone resistance, the AccL-s2 gene for sethoxydim resistance, the bxn gene for bromoxynil resistance, and the csrl gene for chlorsulfuron resistance.

5. The method of claim 1, wherein the plant is selected from the group consisting of rice, wheat, barley, oat, maize, millet, sorghum, pearl barley, sweet potato, potato, lotus seed, soybean, and peanut; preferably, the plant is rice.

6. A method of breeding a transgenic plant, the method comprising:
crossing a first parent plant comprising a first expression vector with a second parent plant comprising a second expression vector, thereby obtaining the transgenic plant comprising the first expression vector and the second expression vector; or
introducing and integrating the first expression vector and the second expression vector into the genome of the same plant, thereby obtaining the transgenic plant,
wherein the first expression vector comprises a lock polynucleotide and an exogenous target gene operably linked thereto, wherein the lock polynucleotide comprises SEQ ID NO: 5 and blocks the expression of the exogenous target gene, and
wherein the second expression vector comprises a key polynucleotide and a tissue-specific promoter operably linked thereto, wherein the key polynucleotide comprises SEQ ID NO: 3 and switches on the expression of the exogenous target gene blocked by the lock polynucleotide.

7. The method of claim 6, wherein the method further comprises, prior to the crossing step, introducing and integrating the first expression vector into the genome of the first parent plant, and introducing and integrating the second expression vector into the genome of the second parent plant.

8. The method of claim 6, wherein the first expression vector further comprises a constitutive promoter operably linked to the lock polynucleotide, wherein the lock polynucleotide is located between the constitutive promoter and the exogenous target gene.

9. The method of claim 8, wherein the constitutive promoter is selected from the group consisting of the cauliflower mosaic virus 35S promoter, the nopaline synthase gene promoter from the T-DNA region of the *Agrobacterium tumefaciens* Ti plasmid, the rice actin promoter Actin I, the maize ubiquitin (Ubi) gene promoter; preferably, the constitutive promoter is the rice actin promoter Actin I.

10. The method of claim 6, wherein the tissue-specific promoter is selected from the group consisting of the rice green tissue-specific promoter ribulose-1,5-bisphosphate carboxylase small subunit (rbcS) promoter, the maize phosphoenolpyruvate carboxylase (PEPC) promoter, the rice green tissue-specific expression DX1 promoter, the rice photosystem II 10 kDa polypeptide D540 promoter, the rice leucine-rich repeat-like receptor protein kinase (LP2) promoter, and the maize chloroplast C4 Pdk promoter; preferably, the tissue-specific promoter is the rbcS promoter.

11. The method of claim 6, wherein the exogenous target gene is an insect resistance gene or a herbicide resistance gene, wherein the insect resistance gene is selected from the group consisting of the cry1Ab, cry1Ac, cry1Ab/1Ac, cry1C, cry2A, and Vip3 like insect resistance genes from *Bacillus thuringiensis*; the anf and sep genes from *Serratia entomophila*; the cmb gene of *Clostridium bifermentans*; the mtx gene from *Bacillus sphaericus*; the insecticidal protein gene from *Xenorhabdus nematophilus*; the tca and tcb genes from *Photorhabdus luminescens*; and the prl gene from *Metarhizium anisopliae*, and wherein the herbicide resistance gene is selected from the group consisting of the EPSP synthase gene for glyphosate resistance, the *Salmonella typhimurium* EPSP mutant gene aroA, the bar gene for glufosinate resistance, the ALS mutant gene Ilv G for imidazolone resistance, the AccL-s2 gene for sethoxydim resistance, the bxn gene for bromoxynil resistance, and the csrl gene for chlorsulfuron resistance.

12. The method of claim 6, wherein the plant is selected from the group consisting of rice, wheat, barley, oat, maize, millet, sorghum, pearl barley, sweet potato, potato, lotus seed, soybean, and peanut; preferably, the plant is rice.

13. A first expression vector and a second expression vector for controlling expression of an exogenous target gene in a plant, the first expression vector comprising a lock polynucleotide and the exogenous target gene operably linked thereto, wherein the lock polynucleotide comprises SEQ ID NO: 5 and blocks the expression of the exogenous target gene, and the second expression vector comprising a key polynucleotide and a tissue-specific promoter operably linked thereto, wherein the key polynucleotide comprises SEQ ID NO: 3 and switches on the expression of the exogenous target gene blocked by the lock polynucleotide.

14. The first expression vector and the second expression vector of claim 13, wherein the first expression vector further comprises a constitutive promoter operably linked to the lock polynucleotide, wherein the lock polynucleotide is located between the constitutive promoter and the exogenous target gene.

15. The first expression vector and the second expression vector of claim 14, wherein the constitutive promoter is selected from the group consisting of the cauliflower mosaic virus 35S promoter, the nopaline synthase gene promoter from the T-DNA region of the *Agrobacterium tumefaciens* Ti plasmid, the rice actin promoter Actin I, and the maize ubiquitin (Ubi) gene promoter.

16. The first expression vector and the second expression vector of claim 14, wherein the constitutive promoter is the rice actin promoter Actin I.

17. The first expression vector and the second expression vector of claim 13, wherein the tissue-specific promoter is selected from the group consisting of the rice green tissue-specific promoter ribulose-1,5-bisphosphate carboxylase small subunit (rbcS) promoter, the maize phosphoenolpyruvate carboxylase (PEPC) promoter, the rice green tissue-specific expression DX1 promoter, the rice photosystem II 10 kDa polypeptide D540 promoter, the rice leucine-rich repeat-like receptor protein kinase (LP2) promoter, and the maize chloroplast C4 Pdk promoter.

18. The first expression vector and the second expression vector of claim 13, wherein the tissue-specific promoter is the rbcS promoter.

19. The first expression vector and the second expression vector of claim 13, wherein the exogenous target gene is an insect resistance gene or a herbicide resistance gene, wherein the insect resistance gene is selected from the group consisting of the cry1Ab, cry1Ac, cry1Ab/1Ac, cry1C, cry2A, and Vip3 like insect resistance genes from *Bacillus thuringiensis*; the anf and sep genes from *Serratia entomophila*; the cmb gene of *Clostridium bifermentans*; the mtx gene from *Bacillus sphaericus*; the insecticidal protein gene from *Xenorhabdus nematophilus*; the tca and tcb genes from *Photorhabdus luminescens*; and the prl gene from *Metarhizium anisopliae*, and wherein the herbicide resistance gene is selected from the group consisting of the EPSP synthase gene for glyphosate resistance, the *Salmonella typhimurium* EPSP mutant gene aroA, the bar gene for glufosinate resistance, the ALS mutant gene Ilv G for imidazolone resistance, the AccL-52 gene for sethoxydim resistance, the bxn gene for bromoxynil resistance, and the csrl gene for chlorsulfuron resistance.

20. The first expression vector and the second expression vector of claim 13, wherein the plant is selected from the group consisting of rice, wheat, barley, oat, maize, millet, sorghum, pearl barley, sweet potato, potato, lotus seed, soybean, and peanut.

21. The first expression vector and the second expression vector of claim 13, wherein the plant is rice.

22. A transgenic rice plant comprising a first expression vector and a second expression vector, the first expression vector comprising a lock polynucleotide, a rice actin promoter Actin I, and an exogenous target gene, wherein the lock polynucleotide comprises SEQ ID NO: 5 and is located between the rice actin promoter Actin I and the exogenous target gene, and the second expression vector comprising a key polynucleotide and a rice green tissue-specific promoter ribulose-1,5-bisphosphate carboxylase small subunit (rbcS) promoter operably linked thereto, wherein the key polynucleotide comprises SEQ ID NO: 3, and wherein the exogenous target gene is Bt gene cry1Ab/1Ac.

23. The transgenic rice plant of claim 22, wherein the transgenic rice plant comprises Bt protein expressed in leaves and stems, with less expression of Cry1Ab/1Ac protein in endosperm than in leaves and stems, or no expression of Cry1Ab/1Ac protein in endosperm.

24. The transgenic rice plant of claim 23, wherein the amount of Cry1Ab/1Ac protein is less than 1 ng/g in refined rice endosperm of the transgenic rice plant.

* * * * *

SEQUENCE LISTING

```
<160> NUMBER OF SEQ ID NOS: 43

<210> SEQ ID NO 1
<211> LENGTH: 1833
<212> TYPE: DNA
<213> ORGANISM: Bacillus thuringi -continued

<400> SEQUENCE: 1

```
atggacaaca actgcaggcc atacaactgc ttgagtaacc cagaagttga agtacttggt     60
ggagaacgca ttgaaaccgg ttacactccc atcgacatct ccttgtcctt gacacagttt    120
ctgctcagcg agttcgtgcc aggtgctggg ttcgttctcg gactagttga catcatctgg    180
ggtatctttg gtccatctca atgggatgca ttcctggtgc aaattgagca gttgatcaac    240
cagaggatcg aagagttcgc caggaaccag gccatctcta ggttggaagg attgagcaat    300
ctctaccaaa tctatgcaga gagcttcaga gagtgggaag ccgatcctac taacccagct    360
ctccgcgagg aaatgcgtat tcaattcaac gacatgaaca gcgccttgac cacagctatc    420
ccattgttcg cagtccagaa ctaccaagtt cctctcttgt ccgtgtacgt tcaagcagct    480
aatcttcacc tcagcgtgct tcgagacgtt agcgtgtttg ggcaaaggtg gggattcgat    540
gctgcaacca tcaatagccg ttacaacgac cttactaggc tgattggaaa ctacaccgac    600
cacgctgttc gttggtacaa cactggcttg gagcgtgtct ggggtcctga ttctagagat    660
tggattagat acaaccagtt caggagagaa ttgaccctca cagttttgga cattgtgtct    720
ctcttcccga actatgactc cagaacctac cctatccgta cagtgtccca acttaccaga    780
gaaatctata ctaacccagt tcttgagaac ttcgacggta gcttccgtgg ttctgcccaa    840
ggtatcgaag gctccatcag gagcccacac ttgatggaca tcttgaacag cataactatc    900
tacaccgatg atcacagagg agagtattac tggtctggac accagatcat ggcctctcca    960
gttggattca gcgggcccga attcaccttt cctctctatg gaactatggg aaacgccgct   1020
ccacaacaac gtatcgttgc tcaactaggt cagggtgtct acagaacctt gtcttccacc   1080
ttgtacagaa gacccttcaa tatcggtatc aacaaccagc aactttccgt tcttgacgga   1140
acagagttcg ccgatggaac ctcttctaac ttgccatccg ctgtttacag aaagagcgga   1200
accgttgatt ccttggacga aatcccacca cagaacaaca atgtgccacc caggcaagga   1260
ttctcccaca ggttgagcca cgtgtccatg ttccgttccg gattcagcaa cagttccgtg   1320
agcatcatca gggctcctat gttctcttgg atacaccgta gtgctgagtt caacaacatc   1380
atcgcatccg atagtattac tcaaatccct gcagtgaagg gaaactttct cttcaacggt   1440
tctgtcattt caggaccagg attcactggt ggagacctcg ttagactcaa cagcagtgga   1500
aataacattc agaatagagg gtatattgaa gttccaattc acttcccatc cacatctacc   1560
agatatagag ttcgtgtgag gtatgcttct gtgaccccta ttcacctcaa cgttaattgg   1620
ggtaattcat ccatcttctc caatacagtt ccagctacag ctacctcctt ggataatctc   1680
caatccagcg atttcggtta ctttgaaagt gccaatgctt ttacatcttc actcggtaac   1740
atcgtgggtg ttagaaactt tagtgggact gcaggagtga ttatcgacag attcgagttc   1800
attccagtta ctgcaacact cgaggctgaa taa                                1833
```

<210> SEQ ID NO 2
<211> LENGTH: 610
<212> TYPE: PRT
<213> ORGANISM: artificial sequence
<220> FEATURE:
<223> OTHER INFORMATION: Bt fusion protein

<400> SEQUENCE: 2

```
Met Asp Asn Asn Cys Arg Pro Tyr Asn Cys Leu Ser Asn Pro Glu Val
1               5                   10                  15

Glu Val Leu Gly Gly Glu Arg Ile Glu Thr Gly Tyr Thr Pro Ile Asp

```
                20                  25                  30
Ile Ser Leu Ser Leu Thr Gln Phe Leu Leu Ser Glu Phe Val Pro Gly
            35                  40                  45

Ala Gly Phe Val Leu Gly Leu Val Asp Ile Ile Trp Gly Ile Phe Gly
        50                  55                  60

Pro Ser Gln Trp Asp Ala Phe Leu Val Gln Ile Glu Gln Leu Ile Asn
65                  70                  75                  80

Gln Arg Ile Glu Glu Phe Ala Arg Asn Asp Ala Ile Ser Arg Leu Glu
                85                  90                  95

Gly Leu Ser Asn Leu Tyr Gln Ile Tyr Ala Glu Ser Phe Arg Glu Trp
            100                 105                 110

Glu Ala Asp Pro Thr Asn Pro Ala Leu Arg Glu Glu Met Arg Ile Gln
        115                 120                 125

Phe Asn Asp Met Asn Ser Ala Leu Thr Thr Ala Ile Pro Leu Phe Ala
            130                 135                 140

Val Gln Asn Tyr Gln Val Pro Leu Leu Ser Val Tyr Val Gln Ala Ala
145                 150                 155                 160

Asn Leu His Leu Ser Val Leu Arg Asp Val Ser Val Phe Gly Gln Arg
                165                 170                 175

Trp Gly Phe Asp Ala Ala Thr Ile Asn Ser Arg Tyr Asn Asp Leu Thr
            180                 185                 190

Arg Leu Ile Gly Asn Tyr Thr Asp His Ala Val Arg Trp Tyr Asn Thr
        195                 200                 205

Gly Leu Glu Arg Val Trp Gly Pro Asp Ser Arg Asp Trp Ile Arg Tyr
            210                 215                 220

Asn Gln Phe Arg Arg Glu Leu Thr Leu Thr Val Leu Asp Ile Val Ser
225                 230                 235                 240

Leu Phe Pro Asn Tyr Asp Ser Arg Thr Tyr Pro Ile Arg Thr Val Ser
                245                 250                 255

Gln Leu Thr Arg Glu Ile Tyr Thr Asn Pro Val Leu Glu Asn Phe Asp
            260                 265                 270

Gly Ser Phe Arg Gly Ser Ala Gln Gly Ile Glu Gly Ser Ile Arg Ser
        275                 280                 285

Pro His Leu Met Asp Ile Leu Asn Ser Ile Thr Ile Tyr Thr Asp Asp
        290                 295                 300

His Arg Gly Glu Tyr Tyr Trp Ser Gly His Gln Ile Met Ala Ser Pro
305                 310                 315                 320

Val Gly Phe Ser Gly Pro Glu Phe Thr Phe Pro Leu Tyr Gly Thr Met
                325                 330                 335

Gly Asn Ala Ala Pro Gln Gln Arg Ile Val Ala Gln Leu Gly Gln Gly
            340                 345                 350

Val Tyr Arg Thr Leu Ser Ser Thr Leu Tyr Arg Arg Pro Phe Asn Ile
        355                 360                 365

Gly Ile Asn Asn Gln Gln Leu Ser Val Leu Asp Gly Thr Glu Phe Ala
        370                 375                 380

Asp Gly Thr Ser Ser Asn Leu Pro Ser Ala Val Tyr Arg Lys Ser Gly
385                 390                 395                 400

Thr Val Asp Ser Leu Asp Glu Ile Pro Pro Gln Asn Asn Asn Val Pro
                405                 410                 415

Pro Arg Gln Gly Phe Ser His Arg Leu Ser His Val Ser Met Phe Arg
            420                 425                 430

Ser Gly Phe Ser Asn Ser Ser Val Ser Ile Ile Arg Ala Pro Met Phe
        435                 440                 445
```

```
Ser Trp Ile His Arg Ser Ala Glu Phe Asn Asn Ile Ile Ala Ser Asp
    450                 455                 460

Ser Ile Thr Gln Ile Pro Ala Val Arg Gly Asn Phe Leu Phe Asn Gly
465                 470                 475                 480

Ser Val Ile Ser Gly Pro Gly Phe Thr Gly Gly Asp Leu Val Arg Leu
                485                 490                 495

Asn Ser Ser Gly Asn Asn Ile Gln Asn Arg Gly Tyr Ile Glu Val Pro
                500                 505                 510

Ile Asn Phe Pro Ser Thr Ser Thr Arg Tyr Arg Val Arg Val Arg Tyr
        515                 520                 525

Ala Ser Val Thr Pro Ile His Leu Asn Val Asn Trp Gly Asn Ser Ser
    530                 535                 540

Ile Phe Ser Asn Thr Val Pro Ala Thr Ala Thr Ser Leu Asp Asn Leu
545                 550                 555                 560

Gln Ser Ser Asp Phe Gly Tyr Phe Glu Ser Ala Asn Ala Phe Thr Ser
                565                 570                 575

Ser Leu Gly Asn Ile Val Gly Val Arg Asn Phe Ser Gly Thr Ala Gly
                580                 585                 590

Val Ile Ile Asp Arg Phe Glu Phe Ile Pro Val Thr Ala Thr Leu Glu
            595                 600                 605

Ala Glu
    610

<210> SEQ ID NO 3
<211> LENGTH: 1116
<212> TYPE: DNA
<213> ORGANISM: artificial sequence
<220> FEATURE:
<223> OTHER INFORMATION: key1 gene

<400> SEQUENCE: 3
atggcggcgg ttaggagaag agaacgagat gtggttgaag agaatggagt tacgacgacg      60
acggtgaaac gaaggaagcc cgggatgtcc aatttactga ccgtacacca aaatttgcct     120
gcattaccgg tcgatgcaac gagtgatgag gttcgcaaga acctgatgga catgttcagg     180
gatcgccagg cgtttttctga gcatacctgg aaaatgcttc tgtccgtttg ccggtcgtgg    240
gcggcatggt gcaagttgaa taccggaaaa tggtttcccg cagaacctga agatgttcgc    300
gattatcttc tatatcttca ggcgcgcggt ctggcagtaa aaactatcca gcaacatttg    360
ggccagctaa acatgcttca tcgtcggtcc gggctgccac gaccaagtga cagcaatgct    420
gtttcactgg ttatgcggcg gatccgaaaa gaaaacgttg atgccggtga acgtgcaaaa    480
caggctctag cgttcgaacg cactgatttc gaccaggttc gttcactcat ggaaaatagc    540
gatcgctgcc aggatatacg taatctggca tttctgggga ttgcttataa caccctgtta    600
cgtatagccg aaattgccag gatcagggtt aaagatatct cacgtactga cggtgggaga    660
atgttaatcc atattggcag aacgaaaacg ctggttagca ccgcaggtgt agagaaggca    720
cttagcctgg gggtaactaa actggtcgag cgatggattt ccgtctctgg tgtagctgat    780
gatccgaata actacctgtt tgccgggtc agaaaaaatg tgttgccgc gccatctgcc     840 accagccagc tatcaactcg cgccctggaa gggatttttg aagcaactca tcgattgatt    900
tacggcgcta aggatgactc tggtcagaga tacctggcct ggtctggaca cagtgcccgt    960
gtcggagccg cgcgagatat ggcccgcgct ggagtttcaa taccgagat catgcaagct   1020 ggtggctgga ccaatgtaaa tattgtcatg aactatatcc gtaacctgga tagtgaaaca   1080
```
ggggcaatgg tgcgcctgct ggaagatggc gattag                                1116

<210> SEQ ID NO 4
<211> LENGTH: 371
<212> TYPE: PRT
<213> ORGANISM: artificial sequence
<220> FEATURE:
<223> OTHER INFORMATION: putative KEY1 protein

<400> SEQUENCE: 4

Met Ala Ala Val Arg Arg Glu Arg Asp Val Val Glu Glu Asn Gly
1               5                   10                  15

Val Thr Thr Thr Val Lys Arg Arg Lys Pro Gly Met Ser Asn Leu
            20                  25                  30

Leu Thr Val His Gln Asn Leu Pro Ala Leu Pro Val Asp Ala Thr Ser
        35                  40                  45

Asp Glu Val Arg Lys Asn Leu Met Asp Met Phe Arg Asp Arg Gln Ala
    50                  55                  60

Phe Ser Glu His Thr Trp Lys Met Leu Leu Ser Val Cys Arg Ser Trp
65                  70                  75                  80

Ala Ala Trp Cys Lys Leu Asn Asn Arg Lys Trp Phe Pro Ala Glu Pro
                85                  90                  95

Glu Asp Val Arg Asp Tyr Leu Leu Tyr Leu Gln Ala Arg Gly Leu Ala
            100                 105                 110

Val Lys Thr Ile Gln Gln His Leu Gly Gln Leu Asn Met Leu His Arg
        115                 120                 125

Arg Ser Gly Leu Pro Arg Pro Ser Asp Ser Asn Ala Val Ser Leu Val
    130                 135                 140

Met Arg Arg Ile Arg Lys Glu Asn Val Asp Ala Gly Glu Arg Ala Lys
145                 150                 155                 160

Gln Ala Leu Ala Phe Glu Arg Thr Asp Phe Asp Gln Val Arg Ser Leu
                165                 170                 175

Met Glu Asn Ser Asp Arg Cys Gln Asp Ile Arg Asn Leu Ala Phe Leu
            180                 185                 190

Gly Ile Ala Tyr Asn Thr Leu Leu Arg Ile Ala Glu Ile Ala Arg Ile
        195                 200                 205

Arg Val Lys Asp Ile Ser Arg Thr Asp Gly Gly Arg Met Leu Ile His
    210                 215                 220

Ile Gly Arg Thr Lys Thr Leu Val Ser Thr Ala Gly Val Glu Lys Ala
225                 230                 235                 240

Leu Ser Leu Gly Val Thr Lys Leu Val Glu Arg Trp Ile Ser Val Ser
                245                 250                 255

Gly Val Ala Asp Asp Pro Asn Asn Tyr Leu Phe Cys Arg Val Arg Lys
            260                 265                 270

Asn Gly Val Ala Ala Pro Ser Ala Thr Ser Gln Leu Ser Thr Arg Ala
        275                 280                 285

Leu Glu Gly Ile Phe Glu Ala Thr His Arg Leu Ile Tyr Gly Ala Lys
    290                 295                 300

Asp Asp Ser Gly Gln Arg Tyr Leu Ala Trp Ser Gly His Ser Ala Arg
305                 310                 315                 320

Val Gly Ala Ala Arg Asp Met Ala Arg Ala Gly Val Ser Ile Pro Glu
                325                 330                 335

Ile Met Gln Ala Gly Gly Trp Thr Asn Val Asn Ile Val Met Asn Tyr
            340                 345                 350

```
Ile Arg Asn Leu Asp Ser Glu Thr Gly Ala Met Val Arg Leu Leu Glu
            355                 360                 365

Asp Gly Asp
    370

<210> SEQ ID NO 5
<211> LENGTH: 333
<212> TYPE: DNA
<213> ORGANISM: artificial sequence
<220> FEATURE:
<223> OTHER INFORMATION: lock1 element

<400> SEQUENCE: 5
ataacttcgt atagcataca ttatacgaag ttatgaattt ccccgatcgt tcaaacattt      60
ggcaataaag tttcttaaga ttgaatcctg ttgccggtct tgcgatgatt atcatataat     120
ttctgttgaa ttacgttaag catgtaataa ttaacatgta atgcatgacg ttatttatga     180
gatgggtttt tatgattaga gtcccgcaat tatacattta atacgcgata gaaaacaaaa     240
tatagcgcgc aaactaggat aaattatcgc gcgcggtgtc atctatgtta ctagatcgga     300
taacttcgta tagcatacat tatacgaagt tat                                  333

<210> SEQ ID NO 6
<211> LENGTH: 1428
<212> TYPE: DNA
<213> ORGANISM: artificial sequence
<220> FEATURE:
<223> OTHER INFORMATION: key2 gene

<400> SEQUENCE: 6
atggcggcgg ttaggagaag agaacgagat gtggttgaag agaatggagt tacgacgacg      60
acggtgaaac gaaggaagtc tagaatggca tccataaatc gccccatagt tttcttcaca     120
gtttgcttgt tcctcttgtg cgatggctcc ctagccatgc cacaatttgg tatattatgt     180
aaaacaccac ctaaggtgct tgttcgtcag tttgtggaaa ggtttgaaag accttcaggt     240
gagaaaatag cattatgtgc tgctgaacta acctatttat gttggatgat tacacataac     300
ggaacagcaa tcaagagagc cacattcatg agctataata ctatcataag caattcgctg     360
agtttcgata ttgtcaataa atcactccag tttaaataca agacgcaaaa agcaacaatt     420
ctggaagcct cattaaagaa attgattcct gcttgggaat ttacaattat tccttactat     480
ggacaaaaac atcaatctga tatcactgat attgtaagta gtttgcaatt acagttcgaa     540
tcatcggaag aagcagataa gggaaatagc cacagtaaaa aaatgcttaa agcacttcta     600
agtgagggtg aaagcatctg ggagatcact gagaaaatac taaattcgtt tgagtatact     660
tcgagattta caaaaacaaa aactttatac caattcctct tcctagctac tttcatcaat     720
tgtggaagat tcagcgatat taagaacgtt gatccgaaat catttaaatt agtccaaaat     780
aagtatctgg gagtaataat ccagtgttta gtgacagaga caaagacaag cgttagtagg     840
cacatatact tctttagcgc aagggggtagg atcgatccac ttgtatattt ggatgaattt     900
ttgaggaatt ctgaaccagt cctaaaacga gtaaatagga ccggcaattc ttcaagcaat     960
aaacaggaat accaattatt aaaagataac ttagtcagat cgtacaataa agcttttgaag    1020 aaaaatgcgc ttattcaat ctttgctata aaaaatggcc caaaatctca cattggaaga     1080
catttgatga cctcatttct ttcaatgaag ggcctaacgg agttgactaa tgttgtggga     1140
aattggagcg ataagcgtgc ttctgccgtg gccaggacaa cgtatactca tcagataaca     1200
gcaatacctg atcactactt cgcactagtt tctcggtact atgcatatga tccaatatca     1260
```

-continued

```
aaggaaatga tagcattgaa ggatgagact aatccaattg aggagtggca gcatatagaa    1320
cagctaaagg gtagtgctga aggaagcata cgatacccg  catggaatgg gataatatca    1380
caggaggtac tagactacct ttcatcctac ataaatagac gcatataa                 1428
```

<210> SEQ ID NO 7
<211> LENGTH: 475
<212> TYPE: PRT
<213> ORGANISM: artificial sequence
<220> FEATURE:
<223> OTHER INFORMATION: putative KEY2 protein

<400> SEQUENCE: 7

```
Met Ala Ala Val Arg Arg Glu Arg Asp Val Val Glu Glu Asn Gly
1               5                  10                  15

Val Thr Thr Thr Val Lys Arg Arg Lys Ser Arg Met Ala Ser Ile
            20                  25                  30

Asn Arg Pro Ile Val Phe Phe Thr Val Cys Leu Phe Leu Cys Asp
        35                  40                  45

Gly Ser Leu Ala Met Pro Gln Phe Gly Ile Leu Cys Lys Thr Pro Pro
    50                  55                  60

Lys Val Leu Val Arg Gln Phe Val Glu Arg Phe Glu Arg Pro Ser Gly
65                  70                  75                  80

Glu Lys Ile Ala Leu Cys Ala Ala Glu Leu Thr Tyr Leu Cys Trp Met
                85                  90                  95

Ile Thr His Asn Gly Thr Ala Ile Lys Arg Ala Thr Phe Met Ser Tyr
            100                 105                 110

Asn Thr Ile Ile Ser Asn Ser Leu Ser Phe Asp Ile Val Asn Lys Ser
        115                 120                 125

Leu Gln Phe Lys Tyr Lys Thr Gln Lys Ala Thr Ile Leu Glu Ala Ser
    130                 135                 140

Leu Lys Lys Leu Ile Pro Ala Trp Glu Phe Thr Ile Ile Pro Tyr Tyr
145                 150                 155                 160

Gly Gln Lys His Gln Ser Asp Ile Thr Asp Ile Val Ser Ser Leu Gln
                165                 170                 175

Leu Gln Phe Glu Ser Ser Glu Glu Ala Asp Lys Gly Asn Ser His Ser
            180                 185                 190

Lys Lys Met Leu Lys Ala Leu Leu Ser Glu Gly Glu Ser Ile Trp Glu
        195                 200                 205

Ile Thr Glu Lys Ile Leu Asn Ser Phe Glu Tyr Thr Ser Arg Phe Thr
    210                 215                 220

Lys Thr Lys Thr Leu Tyr Gln Phe Leu Phe Leu Ala Thr Phe Ile Asn
225                 230                 235                 240

Cys Gly Arg Phe Ser Asp Ile Lys Asn Val Asp Pro Lys Ser Phe Lys
                245                 250                 255

Leu Val Gln Asn Lys Tyr Leu Gly Val Ile Ile Gln Cys Leu Val Thr
            260                 265                 270

Glu Thr Lys Thr Ser Val Ser Arg His Ile Tyr Phe Phe Ser Ala Arg
        275                 280                 285

Gly Arg Ile Asp Pro Leu Val Tyr Leu Asp Glu Phe Leu Arg Asn Ser
    290                 295                 300

Glu Pro Val Leu Lys Arg Val Asn Arg Thr Gly Asn Ser Ser Ser Asn
305                 310                 315                 320

Lys Gln Glu Tyr Gln Leu Leu Lys Asp Asn Leu Val Arg Ser Tyr Asn
                325                 330                 335
```

```
Lys Ala Leu Lys Lys Asn Ala Pro Tyr Ser Ile Phe Ala Ile Lys Asn
                340                 345                 350

Gly Pro Lys Ser His Ile Gly Arg His Leu Met Thr Ser Phe Leu Ser
            355                 360                 365

Met Lys Gly Leu Thr Glu Leu Thr Asn Val Val Gly Asn Trp Ser Asp
370                 375                 380

Lys Arg Ala Ser Ala Val Ala Arg Thr Thr Tyr Thr His Gln Ile Thr
385                 390                 395                 400

Ala Ile Pro Asp His Tyr Phe Ala Leu Val Ser Arg Tyr Tyr Ala Tyr
                405                 410                 415

Asp Pro Ile Ser Lys Glu Met Ile Ala Leu Lys Asp Glu Thr Asn Pro
            420                 425                 430

Ile Glu Glu Trp Gln His Ile Glu Gln Leu Lys Gly Ser Ala Glu Gly
        435                 440                 445

Ser Ile Arg Tyr Pro Ala Trp Asn Gly Ile Ile Ser Gln Glu Val Leu
    450                 455                 460

Asp Tyr Leu Ser Ser Tyr Ile Asn Arg Arg Ile
465                 470                 475
```

<210> SEQ ID NO 8
<211> LENGTH: 333
<212> TYPE: DNA
<213> ORGANISM: artificial sequence
<220> FEATURE:
<223> OTHER INFORMATION: LOCK2 element

<400> SEQUENCE: 8

```
gaagttccta ttctctagaa agtataggaa cttcgaattt ccccgatcgt tcaaacattt      60
ggcaataaag tttcttaaga ttgaatcctg ttgccggtct tgcgatgatt atcatataat     120
ttctgttgaa ttacgttaag catgtaataa ttaacatgta atgcatgacg ttatttatga     180
gatgggtttt tatgattaga gtcccgcaat tatacattta atacgcgata gaaaacaaaa     240
tatagcgcgc aaactaggat aaattatcgc gcgcggtgtc atctatgtta ctagatcggg     300
aagttcctat tctctagaaa gtataggaac ttc                                  333
```

<210> SEQ ID NO 9
<211> LENGTH: 20
<212> TYPE: DNA
<213> ORGANISM: artificial sequence
<220> FEATURE:
<223> OTHER INFORMATION: primer

<400> SEQUENCE: 9

```
gctgttatgc ggccattgtc                                                  20
```

<210> SEQ ID NO 10
<211> LENGTH: 20
<212> TYPE: DNA
<213> ORGANISM: artificial sequence
<220> FEATURE:
<223> OTHER INFORMATION: primer

<400> SEQUENCE: 10

```
gacgtctgtc gagaagtttc                                                  20
```

<210> SEQ ID NO 11
<211> LENGTH: 20
<212> TYPE: DNA
<213> ORGANISM: artificial sequence

```
<220> FEATURE:
<223> OTHER INFORMATION: primer

<400> SEQUENCE: 11
ggccatacaa ctgcttgagt                                               20

<210> SEQ ID NO 12
<211> LENGTH: 20
<212> TYPE: DNA
<213> ORGANISM: artificial sequence
<220> FEATURE:
<223> OTHER INFORMATION: primer

<400> SEQUENCE: 12
gcgtttccca tagttccata                                               20

<210> SEQ ID NO 13
<211> LENGTH: 20
<212> TYPE: DNA
<213> ORGANISM: artificial sequence
<220> FEATURE:
<223> OTHER INFORMATION: primer

<400> SEQUENCE: 13
aacgagtgat gaggttcgca                                               20

<210> SEQ ID NO 14
<211> LENGTH: 20
<212> TYPE: DNA
<213> ORGANISM: artificial sequence
<220> FEATURE:
<223> OTHER INFORMATION: primer

<400> SEQUENCE: 14
acccggcaaa acaggtagtt                                               20

<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
atgtccaatt tactgaccgt                                               20

<210> SEQ ID NO 16
<211> LENGTH: 20
<212> TYPE: DNA
<213> ORGANISM: artificial sequence
<220> FEATURE:
<223> OTHER INFORMATION: primer

<400> SEQUENCE: 16
gcttcaaaaa tcccttccag                                               20

<210> SEQ ID NO 17
<211> LENGTH: 24
<212> TYPE: DNA
<213> ORGANISM: artificial sequence
<220> FEATURE:
<223> OTHER INFORMATION: primer

<400> SEQUENCE: 17
aggctgattg gaaactacac cgac                                          24
```

<210> SEQ ID NO 18
<211> LENGTH: 24
<212> TYPE: DNA
<213> ORGANISM: artificial sequence
<220> FEATURE:
<223> OTHER INFORMATION: primer

<400> SEQUENCE: 18
acagcggatg gcaagttaga agag                                              24

<210> SEQ ID NO 19
<211> LENGTH: 45
<212> TYPE: DNA
<213> ORGANISM: artificial sequence
<220> FEATURE:
<223> OTHER INFORMATION: primer

<400> SEQUENCE: 19
gatcaagctt cacttaaatt ttggtgacag gaatgtagtt ttctg                       45

<210> SEQ ID NO 20
<211> LENGTH: 45
<212> TYPE: DNA
<213> ORGANISM: artificial sequence
<220> FEATURE:
<223> OTHER INFORMATION: primer

<400> SEQUENCE: 20
gtacgtcgac ctctgcagct caccaagctc tctccttctt tgctc                       45

<210> SEQ ID NO 21
<211> LENGTH: 82
<212> TYPE: DNA
<213> ORGANISM: artificial sequence
<220> FEATURE:
<223> OTHER INFORMATION: primer

<400> SEQUENCE: 21
tcgaatggcg gcggttagga agagaacg agatgtggtt gaagagaatg gagttacgac         60
gacgacggtg aaacgaagga ag                                                82

<210> SEQ ID NO 22
<211> LENGTH: 78
<212> TYPE: DNA
<213> ORGANISM: artificial sequence
<220> FEATURE:
<223> OTHER INFORMATION: primer

<400> SEQUENCE: 22
cttccttcgt ttcaccgtcg tcgtcgtaac tccattctct tcaaccacat ctcgttctct       60
tctcctaacc gccgccat                                                     78

<210> SEQ ID NO 23
<211> LENGTH: 61
<212> TYPE: DNA
<213> ORGANISM: artificial sequence
<220> FEATURE:
<223> OTHER INFORMATION: primer

<400> SEQUENCE: 23
gatctctaga gtaccccggg atgtccaatt tactgaccgt acaccaaaat ttgcctgcat       60
t                                                                       61

```
<210> SEQ ID NO 24
<211> LENGTH: 45
<212> TYPE: DNA
<213> ORGANISM: artificial sequence
<220> FEATURE:
<223> OTHER INFORMATION: primer

<400> SEQUENCE: 24
gtacggtacc ctaatcgcca tcttccagca ggcgcaccat tgccc            45

<210> SEQ ID NO 25
<211> LENGTH: 45
<212> TYPE: DNA
<213> ORGANISM: artificial sequence
<220> FEATURE:
<223> OTHER INFORMATION: primer

<400> SEQUENCE: 25
gatcggtacc gctagctcga atttccccga tcgttcaaac atttg            45

<210> SEQ ID NO 26
<211> LENGTH: 45
<212> TYPE: DNA
<213> ORGANISM: artificial sequence
<220> FEATURE:
<223> OTHER INFORMATION: primer

<400> SEQUENCE: 26
gtacgaattc gacaccgcgc gcgataattt atcctagttt gcgcg            45

<210> SEQ ID NO 27
<211> LENGTH: 45
<212> TYPE: DNA
<213> ORGANISM: artificial sequence
<220> FEATURE:
<223> OTHER INFORMATION: primer

<400> SEQUENCE: 27
gatcaagctt gtcgaggtca ttcatatgct tgagaagaga gtcgg            45

<210> SEQ ID NO 28
<211> LENGTH: 45
<212> TYPE: DNA
<213> ORGANISM: artificial sequence
<220> FEATURE:
<223> OTHER INFORMATION: primer

<400> SEQUENCE: 28
gtacctgcag tctacctaca aaaagctcc gcacgaggct gcatt             45

<210> SEQ ID NO 29
<211> LENGTH: 79
<212> TYPE: DNA
<213> ORGANISM: artificial sequence
<220> FEATURE:
<223> OTHER INFORMATION: primer

<400> SEQUENCE: 29
gatcctgcag ataacttcgt atagcataca ttatacgaag ttatgctagc tcgaatttcc    60
ccgatcgttc aaacatttg                                                79

<210> SEQ ID NO 30
<211> LENGTH: 79
<212> TYPE: DNA
<213> ORGANISM: artificial sequence
<220> FEATURE:
```

<223> OTHER INFORMATION: primer

<400> SEQUENCE: 30
gtactctaga ataacttcgt ataatgtatg ctatacgaag ttatgacacc gcgcgcgata    60
atttatccta gtttgcgcg    79

<210> SEQ ID NO 31
<211> LENGTH: 45
<212> TYPE: DNA
<213> ORGANISM: artificial sequence
<220> FEATURE:
<223> OTHER INFORMATION: primer

<400> SEQUENCE: 31
gatctctaga atggtgagca agggcgagga gctgttcacc ggggt    45

<210> SEQ ID NO 32
<211> LENGTH: 45
<212> TYPE: DNA
<213> ORGANISM: artificial sequence
<220> FEATURE:
<223> OTHER INFORMATION: primer

<400> SEQUENCE: 32
gtacggtacc tcaagatctc ttgtacagct cgtccatgcc gagag    45

<210> SEQ ID NO 33
<211> LENGTH: 29
<212> TYPE: DNA
<213> ORGANISM: artificial sequence
<220> FEATURE:
<223> OTHER INFORMATION: primer

<400> SEQUENCE: 33
cgagatctga aggaagcaaa gtggcagca    29

<210> SEQ ID NO 34
<211> LENGTH: 29
<212> TYPE: DNA
<213> ORGANISM: artificial sequence
<220> FEATURE:
<223> OTHER INFORMATION: primer

<400> SEQUENCE: 34
acgcgtcgac taccgccgcc aatcctctt    29

<210> SEQ ID NO 35
<211> LENGTH: 24
<212> TYPE: DNA
<213> ORGANISM: artificial sequence
<220> FEATURE:
<223> OTHER INFORMATION: primer

<400> SEQUENCE: 35
cgagctcaat atacgcagat aaat    24

<210> SEQ ID NO 36
<211> LENGTH: 23
<212> TYPE: DNA
<213> ORGANISM: artificial sequence
<220> FEATURE:
<223> OTHER INFORMATION: primer

<400> SEQUENCE: 36
cgagatctta ccgtaggtat tta    23

<210> SEQ ID NO 37
<211> LENGTH: 25
<212> TYPE: DNA
<213> ORGANISM: artificial sequence
<220> FEATURE:
<223> OTHER INFORMATION: primer

<400> SEQUENCE: 37
ggccttaagg gctagatcat tgtat                                          25

<210> SEQ ID NO 38
<211> LENGTH: 24
<212> TYPE: DNA
<213> ORGANISM: artificial sequence
<220> FEATURE:
<223> OTHER INFORMATION: primer

<400> SEQUENCE: 38
cgagctcctt aaaggggcta gcaa                                           24

<210> SEQ ID NO 39
<211> LENGTH: 61
<212> TYPE: DNA
<213> ORGANISM: artificial sequence
<220> FEATURE:
<223> OTHER INFORMATION: primer

<400> SEQUENCE: 39
aactgcagtc ttcaaggata tgaaagatct cttatccttg aagggctaga tcattgtatc    60
t                                                                    61

<210> SEQ ID NO 40
<211> LENGTH: 60
<212> TYPE: DNA
<213> ORGANISM: artificial sequence
<220> FEATURE:
<223> OTHER INFORMATION: primer

<400> SEQUENCE: 40
cgagatctga agttcctatt ctctagaaag tataggaact tcgaatttcc ccgatcgttc    60

<210> SEQ ID NO 41
<211> LENGTH: 50
<212> TYPE: DNA
<213> ORGANISM: artificial sequence
<220> FEATURE:
<223> OTHER INFORMATION: primer

<400> SEQUENCE: 41
gatcggtacc atggacaaca actgcaggcc atacaactgc ttgagtaacc                50

<210> SEQ ID NO 42
<211> LENGTH: 45
<212> TYPE: DNA
<213> ORGANISM: artificial sequence
<220> FEATURE:
<223> OTHER INFORMATION: primer

<400> SEQUENCE: 42
gtacgtcgac ttattcagcc tcgagtgttg cagtaactgg aatga                    45

<210> SEQ ID NO 43
<211> LENGTH: 55
<212> TYPE: DNA

```
<213> ORGANISM: artificial sequence
<220> FEATURE:
<223> OTHER INFORMATION: primer

<400> SEQUENCE: 43
gatcggtacc gtacgtcgac gctagctcga atttccccga tcgttcaaac atttg        55
```